(12) United States Patent
Lee et al.

(10) Patent No.: US 10,519,449 B2
(45) Date of Patent: Dec. 31, 2019

(54) TREATMENT OF ANGIOGENESIS-ASSOCIATED DISEASES USING RNA COMPLEXES THAT TARGET ANGPT2 AND PDGFB

(71) Applicant: OliX Pharmaceuticals, Inc., Seoul (KR)

(72) Inventors: Dong Ki Lee, Seoul (KR); Sun Woo Hong, Seoul (KR); Tae Yeon Lee, Seoul (KR); Sae-Lo-Oom Lee, Seoul (KR); Hanna Lee, Seoul (KR); Dayeon Yu, Seoul (KR); Ji Eom, Seoul (KR)

(73) Assignee: OliX Pharmaceuticals, Inc., Seoul (KR)

( * ) Notice: Subject to any disclaimer, the term of this patent is extended or adjusted under 35 U.S.C. 154(b) by 0 days.

(21) Appl. No.: 15/422,122

(22) Filed: Feb. 1, 2017

(65) Prior Publication Data

US 2017/0218374 A1 Aug. 3, 2017

Related U.S. Application Data

(60) Provisional application No. 62/290,330, filed on Feb. 2, 2016.

(51) Int. Cl.
| | | |
|---|---|---|
| *C12N 15/113* | (2010.01) | |
| *A61K 31/713* | (2006.01) | |
| *A61K 45/06* | (2006.01) | |

(52) U.S. Cl.
CPC ........ *C12N 15/1136* (2013.01); *A61K 31/713* (2013.01); *A61K 45/06* (2013.01); *C12N 2310/11* (2013.01); *C12N 2310/14* (2013.01); *C12N 2310/315* (2013.01); *C12N 2310/321* (2013.01); *C12N 2310/3515* (2013.01); *C12N 2320/31* (2013.01)

(58) Field of Classification Search
None
See application file for complete search history.

(56) References Cited

U.S. PATENT DOCUMENTS

| | | |
|---|---|---|
| 5,837,258 A | 11/1998 | Grotendorst |
| 7,078,196 B2 | 7/2006 | Tuschl et al. |
| 7,691,997 B2 | 4/2010 | Khvorova et al. |
| 7,700,541 B2 | 4/2010 | Tanaka et al. |
| 8,410,260 B2 | 4/2013 | Collin-Djangone et al. |
| 8,614,309 B2 | 12/2013 | Feinstein et al. |
| 8,802,733 B2 | 8/2014 | Ganesan et al. |
| 8,822,428 B2 | 9/2014 | Collin-Djangone et al. |
| 8,980,273 B1 | 3/2015 | Clube |
| 9,637,742 B2 | 5/2017 | Lee |
| 10,059,949 B2 | 8/2018 | Lee et al. |
| 10,064,801 B2 | 9/2018 | Hong et al. |
| 10,125,362 B2 | 11/2018 | Hong |
| 10,214,744 B2 | 2/2019 | Lee |
| 10,358,648 B2 | 7/2019 | Lee et al. |
| 2004/0138163 A1 | 7/2004 | McSwiggen et al. |
| 2004/0180351 A1 | 9/2004 | Giese et al. |
| 2004/0266707 A1 | 12/2004 | Leake et al. |
| 2005/0119202 A1 | 6/2005 | Kreutzer et al. |
| 2005/0282188 A1 | 12/2005 | Haeberli et al. |
| 2006/0069050 A1 | 3/2006 | Rana |
| 2006/0094032 A1 | 5/2006 | Fougerolles et al. |
| 2006/0105976 A1 | 5/2006 | Soutschek et al. |
| 2006/0134787 A1 | 6/2006 | Zamore et al. |
| 2006/0142228 A1 | 6/2006 | Ford et al. |
| 2006/0160123 A1 | 7/2006 | Quay |
| 2007/0218495 A1 | 9/2007 | Birmingham et al. |
| 2007/0275914 A1 | 11/2007 | Manoharan et al. |
| 2008/0125386 A1 | 5/2008 | Rana et al. |
| 2008/0188430 A1 | 8/2008 | Usman et al. |
| 2009/0004668 A1 | 1/2009 | Chen et al. |
| 2009/0012022 A1 | 1/2009 | Milner et al. |
| 2009/0130751 A1 | 5/2009 | Davidson et al. |
| 2009/0191625 A1 | 7/2009 | Khvorova et al. |
| 2009/0208564 A1 | 8/2009 | Li et al. |
| 2010/0197023 A1 | 8/2010 | Leake et al. |
| 2010/0254945 A1 | 10/2010 | Ge et al. |
| 2010/0291681 A1 | 11/2010 | Khvorova et al. |
| 2011/0028534 A1 | 2/2011 | Shepard et al. |
| 2011/0054160 A1 | 3/2011 | Manoharan |
| 2011/0237647 A1 | 9/2011 | Shirasawa et al. |
| 2011/0237648 A1 | 9/2011 | Khvorova et al. |
| 2011/0251258 A1 | 10/2011 | Samarsky et al. |

(Continued)

FOREIGN PATENT DOCUMENTS

| | | |
|---|---|---|
| CN | 102719432 | 10/2012 |
| EP | 2631291 | 8/2013 |

(Continued)

OTHER PUBLICATIONS

Lee, et al. (2010) Gene Silencing: Theory, Techniques and Applications, Chapter XVI "Asymmetric RNA Duplexes as Next Generation RNAi Inducers". ISBN: 978-1-61728-276-8 . (Year: 2010).*
Costa et al., (2012) "PDGF-B-mediated downregulation of miR-21: new insights into PDGF signaling in glioblastoma", Human Molecular Genetics, vol. 21 No. 23, pp. 5118-5130. (Year: 2012).*
Chang et al., "Asymmetric Shorter-Duplex siRNA Structures Trigger Efficient Gene Silencing with Reduced Nonspecific Effects," Mol Ther, 17(4): 725-735 (2009).
Huang et al., "Targeting the ANGPT-TIE2 Pathway in Malignancy," Nat Rev Cancer, 10: 575-585 (2010).
International Search Report and Written Opinion for International Application No. PCT/IB2017/000167 dated May 25, 2017.

(Continued)

*Primary Examiner* — Jennifer Pitrak McDonald
(74) *Attorney, Agent, or Firm* — Morgan, Lewis & Bockius LLP

(57) ABSTRACT

In certain aspects, provided herein are RNA complexes (e.g., asymmetric RNA complexes, such as asiRNAs or cell penetrating asiRNAs) that inhibit ANGPT2 and/or PDGFB expression and are therefore useful for treating angiogenesis-associated diseases, such as cancer, AMD, and DME.

12 Claims, 20 Drawing Sheets

Specification includes a Sequence Listing.

(56) References Cited

U.S. PATENT DOCUMENTS

| | | |
|---|---|---|
| 2011/0263680 A1 | 10/2011 | Khvorova et al. |
| 2011/0269816 A1 | 11/2011 | Kaspar et al. |
| 2012/0016011 A1 | 1/2012 | Pickering et al. |
| 2012/0238017 A1 | 9/2012 | Lee et al. |
| 2013/0011922 A1* | 1/2013 | Quay .................... C12N 15/111 435/366 |
| 2013/0035368 A1 | 2/2013 | Avkin-Nachum et al. |
| 2013/0115613 A1 | 5/2013 | Madiraiu et al. |
| 2013/0123342 A1 | 5/2013 | Brown |
| 2013/0131142 A1 | 5/2013 | Libertine et al. |
| 2013/0190387 A1 | 7/2013 | Feinstein |
| 2013/0273657 A1 | 10/2013 | Lee |
| 2013/0317080 A1 | 11/2013 | Rajeev et al. |
| 2014/0094501 A1 | 4/2014 | Puri et al. |
| 2014/0227266 A1 | 8/2014 | Lee et al. |
| 2014/0249304 A1 | 9/2014 | Lee et al. |
| 2014/0328903 A1* | 11/2014 | Santel .................... C12N 15/111 424/450 |
| 2014/0350068 A1 | 11/2014 | Feinstein et al. |
| 2015/0111948 A1 | 4/2015 | Hong |
| 2015/0184163 A1 | 7/2015 | Wilson et al. |
| 2016/0017056 A1* | 1/2016 | Clube .................... C07K 14/705 424/158.1 |
| 2016/0122764 A1 | 5/2016 | Chae et al. |
| 2016/0319278 A1 | 11/2016 | Khvorova et al. |
| 2017/0298358 A1 | 10/2017 | Lee et al. |
| 2017/0369882 A1 | 12/2017 | Khvorova et al. |

FOREIGN PATENT DOCUMENTS

| | | |
|---|---|---|
| KR | 101207561 | 12/2012 |
| WO | WO0244321 | 6/2002 |
| WO | WO02055693 | 7/2002 |
| WO | WO2005062937 | 7/2005 |
| WO | WO2005079533 | 9/2005 |
| WO | WO2007002470 | 2/2007 |
| WO | WO2007128477 | 11/2007 |
| WO | 2008109372 | 9/2008 |
| WO | WO2008109377 | 9/2008 |
| WO | WO2009020344 | 2/2009 |
| WO | WO2009029688 | 3/2009 |
| WO | WO2009029690 | 3/2009 |
| WO | WO2009078685 | 6/2009 |
| WO | WO2009105260 | 8/2009 |
| WO | WO2010033247 | 3/2010 |
| WO | WO2010090762 | 8/2010 |
| WO | WO201119887 | 9/2011 |
| WO | WO2012078536 | 6/2012 |
| WO | WO2014043291 | 3/2014 |
| WO | WO2015015498 | 2/2015 |
| WO | WO2015171641 | 11/2015 |
| WO | WO2017017523 | 2/2017 |
| WO | WO2017085550 | 5/2017 |
| WO | WO2017134525 | 8/2017 |
| WO | WO2017134526 | 8/2017 |
| WO | WO2017178883 | 8/2017 |
| WO | WO2018004284 | 1/2018 |
| WO | WO2018146557 | 8/2018 |

OTHER PUBLICATIONS

Kelly et al., "Cell Type-Specific Regulation of Angiogenic Growth Factor Gene Expression and Induction of Angiogenesis in Nonischemic Tissue by a Constitutively Active Form of Hypoxia-inducible Factor 1," Circ Res, 93: 1074-1081 (2003).

Yamagishi et al.,"Pigment epithelium-derived factor (PEDF) promotes growth of pericytes through autocrine production of platelet-derived growth factor-B," Microvascular Research 69 (2005) 128-134.

Jiang et al., "PDGF-B Sustain Self-renewal and Tumorigenicity of Experimental Glioma-Derived Cancer-Initiating Cells by Preventing Oligodendrocyte Differentiation," Neoplasia (2011) 13(6): 492-503.

Joshi, et al., "siRNA: novel therapeutics from functional genomics", Biotechnology and enetic Engineering Reviews (2014) vol. 30, No. 1, pp. 1-30.

Costa et al., "Supplemental Table S3", Human Molecular Genetics, (2012) 21(23):5118-5130.

Ambati et al., "Mechanisms of Age-Related Macular Degeneration," Neuron, 75: 26-39 (2012).

Bolcato-Bellemin et al., "Sticky overhangs enhance siRNA-mediated gene silencing," PNAS, vol. 104, No. 41, pp. 16050-16055 (2007).

Bramsen et al; "Improved silencing properties using small internally segmented interfering RNAs," Nucleic Acids Research, (2007), pp. 5886-5897, vol. 35.

Bushati et al., "MicroRNAs in Neurodegeneration," Current Opin Neurobiol, 18: 292-296 (2008).

Caplen et al., "Specific inhibition of gene expression by small double-stranded RNAs in invertebrate and vertebrate systems," Proc. Natl. Acad. Sci. USA, (2001), pp. 9742-9747, vol. 98, No. 17.

Chang et al., "Structural diversity repertoire of gene silencing small interfering RNAs," Nucleic acid therapeutics, (2011), 21(3), 125-131.

Chang et al., "The design, preparation, and evaluation of asymmetric small interfering RNA for specific gene silencing in mammalian cells." Methods Mol Biol. 2013; 942:135-52.

Chiu et al., "siRNA Function in RNAi: A Chemical Modification Analysis," RNA, 9: 1034-1048 (2003).

Doench et al., "siRNAs Can Function as miRNAs," Gene Dev, 17(4): 438-442 (2003).

Doench et al., "Specificity of MicroRNA Target Selection in Translation Repression," Gene Dev, 18: 504-511 (2004).

Elbashir et al.,"Duplexes of 21-nucleotide RN As mediate RNA interference in cultured mammalian cells," Nature, (2001), 411:494-498.

Elbashir et al., "Functional anatomy of siRNAs for mediating efficient RNAi in Drosophila melanogaster embryo lysate," The EMBO Journal, (2001), pp. 6877-6888, vol. 20, No. 23.

Fire, "RNA-triggered gene silencing," Trends in Genetics, (1999), vol. 15, No. 9, pp. 358-363.

Fire et al., "Potent and specific genetic interference by double-stranded RNA in Caenorhabditis elegans," Nature, (1998), pp. 806-811, vol. 391.

Grimm, "Small silencing RNAs: State of the art," Advanced Drug Delivery Reviews, 61: 672-703 (2009).

Hammond et al., "Post-Transcriptional Gene Silencing by Double-Stranded RNA," Nature Reviews Genetics, (2001), vol. 2: 110-119.

Hong et al., "Effect of the guide strand 3'-end structure on the gene-silencing potency of asymmetric siRNA," Biochemical Journal, (2014), 461(3): 427-434.

Hwang, "Development of Cell-Penetrating Asymmetric Interfering RNA Targeting Connective Tissue Growth Factor," Journal of Investigative Dermatology, (2016), 136(11):2305-2313.

Jackson et al., "Expression Profiling Reveals Off-Target Gene Regulation by RNAi," Nat Biotechnol, 21: 635-637 (2003).

Jang et al., "Gene Delivery From Polymer Scaffolds for Tissue Engineering," Expert Rev Med Devic, 1(1): 127-138 (2004).

Jeong et al., "siRNA conjugate delivery systems," Bioconjugate Chem, 20:5-14 (2009).

Jo et al., "Selection and optimization of asymmetric siRNA targeting the human c-MET gene," Mol Cell, 32:(6) 543-548 (2011).

Kim et al., "Synthetic dsRNA Dicer substrates enhance RNAi potency and efficacy," Nature Biotechnology, 23: 222-226 (2005).

Kore et al., "Chemical modification of synthetic RNAi agents and in vivo delivery techniques," Curr Bioactive Compounds, 4:6-14 (2008).

Kubo et al., "Modified 27nt dsRNAs with Dramatically Enhanced Stability in Serum and Long-Term RN Ai Activity," Oligonucleotides, 17:445-464 (2007).

Kulkarni et al., "Evidence of Off-Target Effects Associated with Long dsRNAs in Drosophila melanogaster Cell-Based Assays," Nat Methods, 3: 833-838 (2006).

Li et al., "Inhibition of connective tissue growth factor by siRNA prevents liver fibrosis in rats," The Journal of Gene Medicine, (2006), 8:889-900.

(56) References Cited

OTHER PUBLICATIONS

Lima et al., "Human Dicer Binds Short Single-strand and Double-strand RNA with High Affinity and Interacts with Different Regions of the Nucleic Acids," The Journal of Biological Chemistry (2009), 284:2535-2548.
Luo et al., "Inhibition of Connective Tissue Growth Factor by Small Interfering RNA Prevents Renal Fibrosis in Rats Undergoing Chronic Allograft Nephropathy," Transplantation Proceedings, (2008), 40:2365-2369.
Marques et al., "A structural basis for discriminating between self and nonself double-stranded RNAs in mammalian cells," Nature Biotechnology, 24: 559-565 (2006).
Martinez et al., "Singe-Stranded Antisense siRNAs Guide Target RNA Cleavage in RNAi," Cell, 110: 563-574 (2002).
Opalinska et al., "Nucleic-acid Therapeutics: Basic Principles and Recent Applications," Nature Rev, 1 (7): 503-514 (2002).
Paroo et al., "Challenges for RNAi in vivo," Trends in Biotech, 22(8): 390-394 (2004).
Patel et al., "A Novel Protective Role for the Innate Immunity Toll-Like Receptor 3 (TLR3) in the Retina via Stat3," Mol Cell Neurosci, 63: 38-48 (2014).
Raouane et al., "Lipid conjugated oligonucleotides: a useful strategy for delivery," Bioconjugate Chem, 23:1091-104 (2012).
Rose et al., "Functional Polarity is Introduced by Dicer Processing of Short Substrate RNAs," Nucleic Acids Res, 33: 4140-4156 (2005).
Sano et al., "Effect of asymmetric terminal structures of short RNA duplexes on the RNA interference activity and strand selection," Nucleic Acids Research (2008), 36: 5812-5821.
Sharp et al., "RNA-interference-2001," Genes & Development, (2001), 15:485-490.
Sioud et al., "Cationic liposome-mediated delivery of siRNAs in adult mice," Biochem Biophys Res Commun. Dec. 26, 2003; 312(4):1220-5.
Sisco et al., "Antisense Inhibition of Connective Tissue Growth Factor (CTGF/CCN2) mRNA Limits Hypertrophic Scarring Without Affecting Wound Healing in Vivo," Wound Repair Regen, 16: 661-673 (2008).
Song et al., "The Crystal Structure of the Argonaute2 PAZ Domain Reveals an RNA Binding Motif in RNAi Effector Complexes," Nat Struct Biol, 10(12): 1026-1032 (2003).
Soutschek et al., "Therapeutic Silencing of an Endogenous Gene by Systemic Adminstration of Modified siRNAs," Nature, 432: 173-178 (2004).
Sun et al., "Asymmetric RNA duplexes mediate RNA interference in mammalian cells," Nature Biotechnology, 26: 1379-1382 (2008).
Ui-Tei et al., "Essential Notes Regarding the Design of Functional siRNAs for Efficient Mammalian RNAi," J Biomed Biotechnol, 2006; 2006(4):65052. doi: 10.1155/JBB/2006/65052.
Ui-Tei et al., "Guidelines for the selection of highly effective siRNA sequences for mammalian and chick RNA interference," (2004), Nucleic Acids Research, vol. 32, pp. 936-948.
Vasdudevan et al., "Switching from Repression to Activation: MicroRNAs Can Up-Regulate Translation," Science, 318: 1931-1934 (2007).
Wang et al., "Nucleation, Propagation and Cleavage of Target RNAs in Ago Silencing Complexes," Nature, 461: 754-762 (2009).
Yang et al., "HEN1 recognizes 21-24 nt small RNA duplexes and deposits a methyl group onto the 2' OH of the 3' terminal nucleotide," Nucleic Acids Research, 34: 667-675 (2006).
Yuan et al., "Asymmetric siRNA: New Strategy to Improve Specificity and Reduce Off-Target Gene Expression", Human Gene Therapy 23:521-532 (2013).
Zamore, "RNA interference: listening to the sound of silence," Nature Structural Biology, (2001), 8(9):746-750.
Costa et al., "PDGF-B-mediated downregulation of miR-21: new insights into PDGF signaling in glioblastoma", Human Molecular Genetics, (2012) vol. 21 No. 23, pp. 5118-5130.
Lee et al., "Asymmetric RNA Duplexes as Next Generation RNAi Inducers", Gene Silencing: Theory, Techniques and Applications, (2010), pp. 343-348.
Joshi, et al., "siRNA: novel therapeutics from functional genomics", Biotechnology and enetic Enginnering Reviews (2014) vol. 30, No. 1, pp. 1-30.
Lee et al., "Asymmetric RNA Duplexes as Next Generation RNAi Inducers", Gene Silencing: Theory, Techniques and Applications, (2010), 343-348.

\* cited by examiner

Figure 10

Human ANGPT2 mRNA sequence (NM_001147.2) SEQ ID NO: 457

```
   1 aaagtgattg attcggatac tgacactgta ggatctgggg agagaggaac aaaggaccgt
  61 gaaagctgct ctgtaaaagc tgacacagcc ctcccaagtg agcaggactg ttcttcccac
 121 tgcaatctga cagtttactg catgcctgga gagaacacag cagtaaaaac caggtttgct
 181 actggaaaaa gaggaaagag aagactttca ttgacggacc cagccatggc agcgtagcag
 241 ccctgcgttt tagacggcag cagctcggga ctctggacgt gtgtttgccc tcaagtttgc
 301 taagctgctg gtttattact gaagaaagaa tgtggcagat tgttttcttt actctgagct
 361 gtgatcttgt cttggccgca gcctataaca actttcggaa gagcatggac agcataggaa
 421 agaagcaata tcaggtccag catgggtcct gcagctacac tttcctcctg ccagagatgg
 481 acaactgccg ctcttcctcc agcccctacg tgtccaatgc tgtgcagagg gacgcgccgc
 541 tcgaatacga tgactcggtg cagaggctgc aagtgctgga gaacatcatg gaaaacaaca
 601 ctcagtggct aatgaagctt gagaattata tccaggacaa catgaagaaa gaaatggtag
 661 agatacagca gaatgcagta cagaaccaga cggctgtgat gatagaaata gggacaaacc
 721 tgttgaacca aacagcggag caaacgcgga agttaactga tgtggaagcc aagtattaa
 781 atcagaccac gagacttgaa cttcagctct tggaacactc cctctcgaca aacaaattgg
 841 aaaaacagat tttggaccag accagtgaaa taaacaaatt gcaagataag aacagtttcc
 901 tagaaaagaa ggtgctagct atggaagaca agcacatcat ccaactacag tcaataaaag
 961 aagagaaaga tcagctacag gtgttagtat ccaagcaaaa ttccatcatt gaagaactag
1021 aaaaaaaaat agtgactgcc acggtgaata attcagttct tcagaagcag caacatgatc
1081 tcatggagac agttaataac ttactgacta tgatgtccac atcaaactca gctaaggacc
1141 ccactgttgc taaagaagaa caaatcagct tcagagactg tgctgaagta ttcaaatcag
1201 gacacaccac gaatggcatc tacacgttaa cattccctaa ttctacagaa gagatcaagg
1261 cctactgtga catggaagct ggaggaggcg ggtggacaat tattcagcga cgtgaggatg
1321 gcagcgttga ttttcagagg acttggaaag aatataaagt gggatttggt aaccccttcag
1381 gagaatattg gctgggaaat gagtttgttt cgcaactgac taatcagcaa cgctatgtgc
1441 ttaaaataca ccttaaagac tgggaaggga atgaggctta ctcattgtat gaacatttct
1501 atctctcaag tgaagaactc aattatagga ttcaccttaa aggacttaca gggacagccg
1561 gcaaaataag cagcatcagc caaccaggaa atgatttttag cacaaaggat ggagacaacg
1621 acaaatgtat ttgcaaatgt tcacaaatgc taacaggagg ctggtggttt gatgcatgtg
1681 gtccttccaa cttgaacgga atgtactatc cacagaggca gaacacaaat aagttcaacg
```

Figure 10 (Cont.)

1741 gcattaaatg gtactactgg aaaggctcag gctattcgct caaggccaca accatgatga 1801 tccgaccagc agatttctaa acatcccagt ccacctgagg aactgtctcg aactattttc 1861 aaagacttaa gcccagtgca ctgaaagtca cggctgcgca ctgtgtcctc ttccaccaca 1921 gagggcgtgt gctcggtgct gacgggaccc acatgctcca gattagagcc tgtaaacttt 1981 atcacttaaa cttgcatcac ttaacggacc aaagcaagac cctaaacatc cataattgtg 2041 attagacaga acacctatgc aaagatgaac ccgaggctga gaatcagact gacagtttac 2101 agacgctgct gtcacaacca agaatgttat gtgcaagttt atcagtaaat aactggaaaa 2161 cagaacactt atgttataca atacagatca tcttggaact gcattcttct gagcactgtt 2221 tatacactgt gtaaataccc atatgtcctg aattcaccat cactatcaca attaaaagga 2281 agaaaaaaac tctctaagcc ataaaaagac atattcaggg atattctgag aaggggttac 2341 tagaagttta atatttggaa aaacagttag tgcattttta ctccatctct taggtgcttt 2401 aaattttat ttcaaaaaca gcgtatttac atttatgttg acagcttagt tataagttaa 2461 tgctcaaata cgtatttcaa atttatatgg tagaaacttc cagaatctct gaaattatca 2521 acagaaacgt gccattttag tttatatgca gaccgtacta ttttttctg cctgattgtt 2581 aaatatgaag gtatttttag taattaaata taacttatta ggggatatgc ctatgtttaa 2641 cttttatgat aatatttaca attttataat ttgtttccaa aagacctaat tgtgccttgt 2701 gataaggaaa cttcttactt ttaatgatga ggaaaattat acatttcatt ctatgacaaa 2761 gaaactttac tatcttctca ctattctaaa acagaggtct gttttctttc ctagtaagat 2821 atattttat agaactagac tacaatttaa tttctggttg agaaaagcct tctatttaag 2881 aaatttacaa agctatatgt ctcaagattc acccttaaat ttacttaagg aaaaaaataa 2941 ttgacactag taagttttt tatgtcaatc agcaaactga aaaaaaaaaa agggtttcaa 3001 agtgcaaaaa caaaatctga tgttcataat atatttaaat atttaccaaa aatttgagaa 3061 cacagggctg ggcgcagtgg ctcacaccta aatcccagt acattggtag gcaaggtggg 3121 cagatcacct gaggtcagga gttcaagacc agcctggaca acatggtgaa accctgtctc 3181 tactaaataa tacaaaaatt agccaggcgt gctggcgggc acctgtaatc ccagctactc 3241 gggaggctga ggcagggaga attgcttgca ccagggaggt agaggttgca gtgagccaag 3301 atcgcaccac tgcactccag ccggggcaac agagcaagac tccatctcaa aaaaaaaaa 3361 aaaaaagaa agaaaagaaa atttgagaac acagctttat actcgggact acaaaaccat 3421 aaactcctgg agttttaact ccttttgaaa ttttcatagt acaattaata ctaatgaaca 3481 tttgtgtaaa gctttataat ttaaaggcaa tttctcatat attcttttct gaatcatttg 3541 caaggaagtt cagagtccag tctgtaacta gcatctacta tatgtctgtc ttcaccttac

Figure 10 (Cont.)

3601 agtgttctac cattattttt tctttattcc atttcaaaat ctaatttatt ttaccccaac 3661 ttctccccac cacttgacgt agttttagaa cacacaggtg ttgctacata tttggagtca 3721 atgatggact ctggcaaagt caaggctctg ttttatttcc accaaggtgc acttttccaa 3781 caactattta actagttaag aacctcccta tcttagaact gtatctactt tatatttaag 3841 aaggttttat gaattcaaca acggtatcat ggccttgtat caagttgaaa aacaactgaa 3901 aataagaaaa tttcacagcc tcgaaagaca acaacaagtt tctaggatat ctcaatgaca 3961 agagtgatgg atacttaggt agggaaacgc taatgcagga aaaactggca acaacacaat 4021 ttatatcaat tctctttgta ggcaggtgat aaaaaattca aggacaaatc tcattatgtc 4081 attgtgcatc atatataatc tcttatgagc gagaatgggg ggaatttgtg tttttacttt 4141 acacttcaat tccttacacg gtatttcaaa caaacagttt tgctgagagg agcttttgtc 4201 tctccttaag aaaatgttta taaagctgaa aggaaatcaa acagtaatct taaaaatgaa 4261 aacaaaacaa cccaacaacc tagataacta cagtgatcag ggagcacagt tcaactcctt 4321 gttatgtttt agtcatatgg cctactcaaa cagctaaata acaacaccag tgcagataa 4381 aaatcaccat ttatctttca gctattaatc ttttgaatga ataaactgtg acaaacaaat 4441 taacatttt gaacatgaaa ggcaacttct gcacaatcct gtatccaagc aaactttaaa 4501 ttatccactt aattattact taatcttaaa aaaaattaga acccagaact tttcaatgaa 4561 gcatttgaaa gttgaagtgg aatttaggaa agccataaaa atataaatac tgttatcaca 4621 gcaccagcaa gccataatct ttatacctat cagttctatt tctattaaca gtaaaaacat 4681 taagcaagat ataagactac ctgcccaaga attcagtctt ttttcatttt tgttttctc 4741 agttctgagg atgttaatcg tcaaattttc tttggactgc attcctcact acttttgca 4801 caatggtctc acgttctcac atttgttctc gcgaataaat tgataaaagg tgttaagttc 4861 tgtgaatgtc tttttaatta tgggcataat tgtgcttgac tggataaaaa cttaagtcca 4921 cccttatgtt tataataatt tcttgagaac agcaaactgc atttaccatc gtaaaacaac 4981 atctgactta cgggagctgc agggaagtgg tgagacagtt cgaacggctc ctcagaaatc 5041 cagtgaccca attctaaaga ccatagcacc tgcaagtgac acaacaagca gatttattat 5101 acatttatta gccttagcag gcaataaacc aagaatcact ttgaagacac agcaaaaagt 5161 gatacactcc gcagatctga aatagatgtg ttctcagaca acaaagtccc ttcagaatct 5221 tcatgttgca taaatgttat gaatattaat aaaaagttga ttgagaaaaa Figure 14
(A)
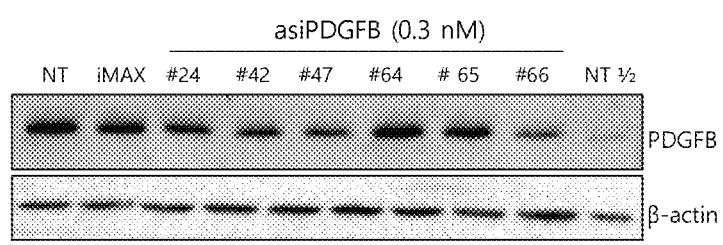
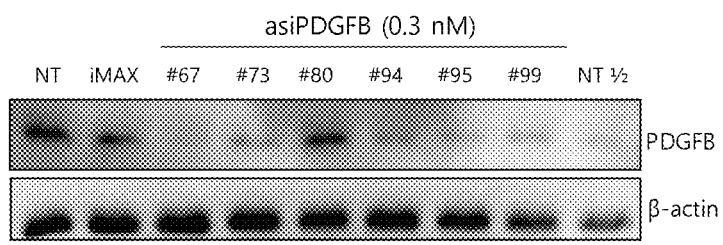
(B)
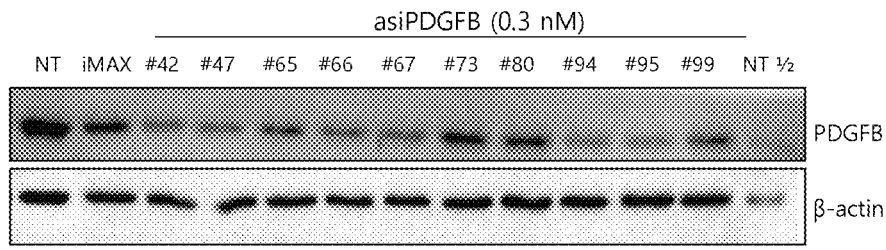

Figure 18

Human PDGFB mRNA sequence. (NM_033016) SEQ ID NO: 458

```
   1 agagagagag agagactgac tgagcaggaa tggtgagatg tttatcatgg gcctcgggga
  61 ccccattccc gaggagcttt atgagatgct gagtgaccac tcgatccgct cctttgatga
 121 tctccaacgc ctgctgcacg gagaccccgg agaggaagat ggggccgagt tggacctgaa
 181 catgacccgc tcccactctg gaggcgagct ggagagcttg gctcgtggaa gaggagcct
 241 gggttccctg accattgctg agccggccat gatcgccgag tgcaagacgc gcaccgaggt
 301 gttcgagatc tcccggcgcc tcatagaccg caccaacgcc aacttcctgg tgtggccgcc
 361 ctgtgtggag gtgcagcgct gctccggctg ctcaacaac cgcaacgtgc agtgccgccc
 421 cacccaggtg cagctgcgac ctgtccaggt gagaaagatc gagattgtgc ggaagaagcc
 481 aatctttaag aaggccacgg tgacgctgga agaccacctg gcatgcaagt gtgagacagt
 541 ggcagctgca cggcctgtga cccgaagccc gggggttcc caggagcagc gagccaaaac
 601 gccccaaact cgggtgacca ttcggacggt gcgagtccgc cggcccccca agggcaagca
 661 ccggaaattc aagcacacgc atgacaagac ggcactgaag gagacccttg agcctaggg
 721 gcatcggcag gagagtgtgt gggcagggtt atttaatatg gtatttgctg tattgcccc
 781 atgggggtcct tggagtgata atattgtttc cctcgtccgt ctgtctcgat gcctgattcg
 841 gacggccaat ggtgcttccc ccacccctcc acgtgtccgt ccaccttcc atcagcgggt
 901 ctcctcccag cggcctccgg cgtcttgccc agcagctcaa gaagaaaag aaggactgaa
 961 ctccatcgcc atcttcttcc cttaactcca agaacttggg ataagagtgt gagagagact
1021 gatggggtcg ctctttgggg gaaacgggct ccttcccctg cacctggcct gggccacacc
1081 tgagcgctgt ggactgtcct gaggagccct gaggacctct cagcatagcc tgcctgatcc
1141 ctgaacccct ggccagctct gaggggaggc acctccaggc aggcaggct gcctcggact
1201 ccatggctaa gaccacagac gggcacacag actggagaaa acccctccca cggtgcccaa
1261 acaccagtca cctcgtctcc ctggtgcctc tgtgcacagt ggcttctttt cgttttcgtt
1321 ttgaagacgt ggactcctct tggtgggtgt ggccagcaca ccaagtggct gggtgccctc
1381 tcaggtgggt tagagatgga gtttgctgtt gaggtggctg tagatggtga cctgggtatc
1441 ccctgcctcc tgccacccct tcctccccac actccactct gattcacctc ttcctctggt
1501 tcctttcatc tctctacctc cacccctgcat tttcctcttg tcctggccct tcagtctgct
1561 ccaccaaggg gctcttgaac cccttattaa ggccccagat gatcccagtc actcctctct
1621 agggcagaag actagaggcc agggcagcaa gggacctgct catcatattc caacccagcc
1681 acgactgcca tgtaaggttg tgcagggtgt gtactgcaca aggacattgt atgcagggag
1741 cactgttcac atcatagata aagctgattt gtatatttat tatgacaatt tctggcagat
1801 gtaggtaaag aggaaaagga tcctttcct aattcacaca aagactcctt gtggactggc
1861 tgtgccctg atgcagcctg tggcttggag tggccaaata ggagggagac tgtggtaggg
1921 gcagggaggc aacactgctg tccacatgac ctccatttcc caaagtcctc tgctccagca
1981 actgcccttc caggtggggt tgggacacct gggagaaggt ctccaaggga gggtgcagcc
2041 ctcttgcccg cacccctccc tgcttgcaca cttccccatc tttgatcctt ctgagctcca
2101 cctctggtgg ctcctcctag gaaaccagct cgtgggctgg aatgggga gagaagggaa
2161 aagatcccca agacccctg gggtgggatc tgagctccca cctcccttcc cacctactgc
2221 actttccccc ttccgccctt ccaaaacctg cttccttcag tttgtaaagt cggtgattat
2281 attttggggg gctttccttt tattttttaa atgtaaaatt tatttatat ccgtatttaa
2341 agttgtaaaa aaaaataacc acaaacaaa accaaatgaa tccgccggag gtctgtctgt
2401 tggcatcgtg cgtgacaatt aacctttctg ccttggcagg atgtgccgac agcttgcggc
2461 gtgttcctct cactctggga gcctcaggcg tgatctcaca cactggcgtg cacatacaca
2521 cacacacaca tacatgctca cacatgcgtg cacatacacg caggcctgca acttggggga
2581 ggcctctgtc tggcgggaag aagagacaca caggctactc tgttggtctt ggtcctggca
2641 cagctcctga cacgtggact tgtgcgtgtc tctggcagtg acgagagatg ggtttctgca
```

TREATMENT OF ANGIOGENESIS-ASSOCIATED DISEASES USING RNA COMPLEXES THAT TARGET ANGPT2 AND PDGFB

RELATED APPLICATIONS

This application claims the benefit of priority to U.S. Provisional Patent Application Ser. No. 62/290,330, filed Feb. 2, 2016, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 10, 2017, is named OPH-00801_SL.txt and is 118,756 bytes in size.

BACKGROUND

Angiogenesis is a term used to describe the growth of new blood vessels. The growth and proliferation of blood vessels plays an important role in many biological processes. One example is tumor development, where the development of blood vessels within the tumor allows the tumor to grow through increased access to oxygen and nutrients, increases tumor survival, and facilitates tumor metastasis. Targeting angiogenesis is a promising route to treat cancer.

Angiogenesis in the eyes usually plays an important role in supply of sufficient oxygen and other necessary nutrients to the eyes and the development of normal tissues. However, when excessive and abnormal blood vessel development is occurred, ocular diseases, such as wet age-related macular degeneration (wet AMD) and diabetic macular edema (DME), can be induced, and in some cases, even blindness may result.

Age-related macular degeneration (AMD) is a disease that results from the degeneration of the retinal pigmented epithelium lining in the eye's macula, which leads to vision loss. The macula is a small area in the retina made up of the light-sensitive tissues lining the back of the eye and plays a critical role in central vision. AMD is one of the leading causes of blindness worldwide. AMD occurs in "wet" and "dry" forms. Wet AMD is the result of abnormal blood vessel growth in the retina. In wet AMD, increased amount of vascular endothelial growth factor (VEGF) contributes to this neovascularization, so therapeutic options include the use of VEGF inhibitors. However, many patients treated with VEGF inhibitors develop geographic atrophy (GA), which is a primary symptom of late dry macular degeneration, within a few years of treatment. Diabetic macular edema (DME) is a disease that resulted from swelling of the retina in diabetes mellitus due to leaking of fluid from blood vessels within the macula. The poor blood circulation in diabetic patients can accelerate the new blood vessel development in the macula, and retinal edema can result from the leakage of blood vessels with think or weak walls. DME is the leading cause of blindness in patients with diabetes, and 10% of the diabetics suffer from macular edema.

SUMMARY

In certain aspects, provided herein are RNA complexes that target ANGPT2 (Angiopoietin 2) or PDGFB (Platelet Derived Growth Factor Beta) and are useful for treating and/or preventing angiogenesis-associated diseases, such as AMD (e.g., wet AMD), DME, and cancer. In certain aspects, provided herein are RNA complexes that inhibit angiogenesis. In certain aspects, provided herein are pharmaceutical compositions comprising such RNA complexes and methods of using such RNA complexes and pharmaceutical compositions.

In certain aspects, provided herein is an RNA complex comprising an antisense strand having sequence complementarity to an ANGPT2 or PDGFB mRNA sequence and a sense strand having sequence complementarity to the antisense strand. In some embodiments, the RNA complex is capable of inhibiting ANGPT2 or PDGFB expression by a cell. In some embodiments, the RNA complex is an asymmetric shorter-duplex small interfering RNA (an asiRNA). In some embodiments, the RNA complex is an RNA complex listed in Table 1, Table 2, Table 3, Table 4, Table 5, or Table 6. In some embodiments, the RNA complex provided herein comprises a chemical modification, wherein the modification facilitates the penetration of a cellular membrane in the absence of a delivery vehicle. In some embodiments, the modification is a 2'-O-methylated nucleoside, a phosphorothioate bond or a hydrophobic moiety. In some embodiments, the chemical modification is a hydrophobic moiety. In some embodiments, the hydrophobic moiety is a cholesterol moiety. In some embodiments, the RNA complex is a modified RNA complex listed in Table 2, Table 3, Table 5, or Table 6. In certain embodiments, the RNA complex is not cytotoxic.

In certain aspects, provided herein is a pharmaceutical composition comprising an RNA complex provided herein and a pharmaceutically acceptable carrier. In certain embodiments, the pharmaceutical composition is formulated for parenteral delivery. In some embodiments, the pharmaceutical composition formulated for oral delivery. In some embodiments, the pharmaceutical composition is formulated for intravenous delivery. In some embodiments, the pharmaceutical composition is formulated for intravitreal delivery. In other embodiments, the pharmaceutical composition is formulated as an eye drop.

In certain aspects, provided herein is a method of inhibiting ANGPT2 or PDGFB expression by a cell, comprising contacting the cell with an RNA complex provided herein. In certain aspects, provided herein is a method of inhibiting gene expression ANGPT2 or PDGFB in a human subject, comprising administering to the subject an RNA complex or pharmaceutical composition provided herein. In certain aspects, provided herein is a method of inhibiting angiogenesis in a human subject, comprising contacting the cell with an RNA complex provided herein. In certain aspects, provided herein is a method of treating a human subject for an angiogenesis-associated disease, such as age-related macular degeneration, diabetic macular edema, or cancer comprising administering to the subject an RNA complex or pharmaceutical composition provided herein.

BRIEF DESCRIPTION OF THE DRAWINGS

FIG. 10 shows the mRNA sequence of human ANGPT2 variant 1. Figure discloses SEQ ID NO: 457.

FIG. 14 shows the inhibition of PDGFB protein expression by 12 exemplary asiRNAs that target PDGFB.

FIG. 18 shows the mRNA sequence of human PDGFB variant 2. Figure discloses SEQ ID NO: 458.

DETAILED DESCRIPTION

General

Figure 1:
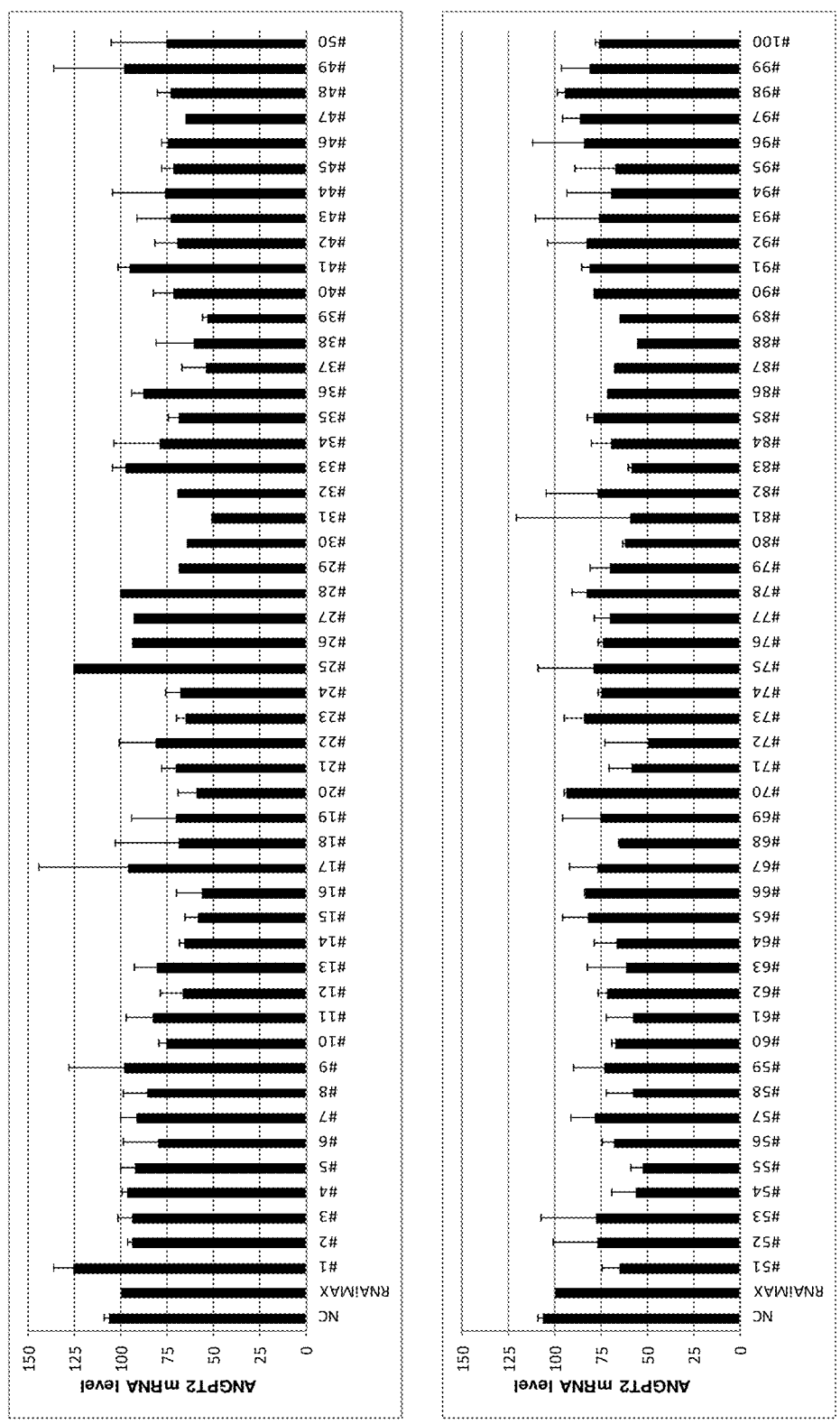
FIG. 1 shows the gene silencing efficiency of 100 exemplary asiRNAs that target ANGPT2. SK-N-SH cells were transfected with 0.1 nM asiRNAs.

In certain aspects, provided herein are asymmetric RNA complexes (e.g., asiRNAs or cp-asiRNAs) that inhibit ANGPT2 or PDGFB and are therefore useful for the treatment of angiogenesis-associated diseases, such as AMD (e.g. wet or dry AMD), DME, and cancer. In some embodiments, the RNA complexes are chemically modified to be capable of penetrating a cell without need for a transfection vehicle. In some embodiments, the RNA complex is an RNA complex listed in Table 1, Table 2, Table 3, Table 4, Table 5, or Table 6. In certain aspects, provided herein are pharmaceutical compositions comprising such RNA complexes and methods of using such RNA complexes and pharmaceutical compositions.

In some embodiments, the RNA complexes described herein are asiRNAs or cp-asiRNAs. As used herein, the term asiRNA refers to double-stranded asymmetric shorter-duplex small interfering RNA molecules that have a 19-21 nt antisense strand and a 13-17 nt sense strand. Additional information on asiRNAs can be found in U.S. Pat. Pub. No. 2012/0238017 and in Chang et al., Mol. Ther. 17:725-732 (2009), each of which is hereby incorporated by reference in its entirety.

In some embodiments, the RNA complexes described herein are delivered to cells using a delivery vehicle, such as liposomes, cationic polymers, cell penetrating peptides (CPPs), protein transduction domains (PTDs), antibodies and/or aptamers. In some embodiments, the RNA complex described herein is chemically modified so as to not require the use of such delivery vehicles to mediate ANGPT2 or PDGFB inhibition in a cell. Such RNA complexes are referred to herein as cell-penetrating asiRNAs (cp-asiRNAs).

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

As used herein, the term "administering" means providing a pharmaceutical agent or composition to a subject, and includes, but is not limited to, administering by a medical professional and self-administering.

As used herein, the term "immunomodulator" refers to a compound or composition that weakens, stimulates, or otherwise modulates the immune system. Examples include, by are not limited to leukotriene receptor agonists, immunosuppressants (e.g., FK-506), or cytokines.

As used herein, the terms "interfering nucleic acid" and "inhibiting nucleic acid" are used interchangeably. Interfering nucleic acids generally include a sequence of cyclic subunits, each bearing a base-pairing moiety, linked by intersubunit linkages that allow the base-pairing moieties to hybridize to a target sequence in a nucleic acid (typically RNA) by Watson-Crick base pairing, to form a nucleic acid: oligomer heteroduplex within the target sequence. Interfering RNA molecules include, but are not limited to, antisense molecules, siRNA molecules, asiRNA molecules, cp-asiRNA molecules, single-stranded siRNA molecules, miRNA molecules and shRNA molecules. Such an interfering nucleic acids can be designed to block or inhibit translation of mRNA or to inhibit natural pre-mRNA splice processing, or induce degradation of targeted mRNAs, and may be said to be "directed to" or "targeted against" a target sequence with which it hybridizes. Interfering nucleic acids may include, for example, peptide nucleic acids (PNAs), locked nucleic acids (LNAs), 2'-O-Methyl oligonucleotides and RNA interference agents (siRNA agents). RNAi molecules generally act by forming a heteroduplex with the target molecule, which is selectively degraded or "knocked down," hence inactivating the target RNA. Under some conditions, an interfering RNA molecule can also inactivate a target transcript by repressing transcript translation and/or inhibiting transcription of the transcript. An interfering nucleic acid is more generally said to be "targeted against" a biologically relevant target, such as a protein, when it is targeted against the nucleic acid of the target in the manner described above.

The terms "polynucleotide", and "nucleic acid" are used interchangeably. They refer to a polymeric form of nucleotides, whether deoxyribonucleotides, ribonucleotides, or analogs thereof, in any combination and of any length. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleobases are interchangeable with T nucleobases.

The phrase "pharmaceutically-acceptable carrier" as used herein means a pharmaceutically-acceptable material, composition or vehicle, such as a liquid or solid filler, diluent, excipient, or solvent encapsulating material.

As used herein, a therapeutic that "prevents" a disorder or condition refers to a compound that, when administered to a statistical sample prior to the onset of the disorder or condition, reduces the occurrence of the disorder or condition in the treated sample relative to an untreated control sample, or delays the onset or reduces the severity of one or more symptoms of the disorder or condition relative to the untreated control sample.

An oligonucleotide "specifically hybridizes" to a target polynucleotide if the oligomer hybridizes to the target under physiological conditions, with a Tm substantially greater than 45° C., or at least 50° C., or at least 60° C.-80° C. or higher. Such hybridization corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

As used herein, the term "subject" means a human or non-human animal selected for treatment or therapy.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

RNA Complexes

In certain aspects, provided herein are RNA complexes that target ANGPT2 and/or PDGFB mRNA and inhibit ANGPT2 and/or PDGFB expression by a cell, respectively. In some embodiments, the cell is a A549 cell. In some embodiments, the cell is a SK-N-SH cell. In some embodiments, the cell is a tumor cell. The nucleic acid sequence of human ANGPT2 and PDGFB mRNA is provided in FIG. 10, and FIG. 18, respectively.

In certain aspects, provided herein is an RNA complex comprising an antisense strand having sequence complementarity to an ANGPT2 and/or PDGFB mRNA sequence (e.g., a human ANGPT2 or PDGFB mRNA sequence) and a sense strand having sequence complementarity to the antisense strand. In some embodiments, the RNA complex is capable of inhibiting ANGPT2 or PDGFB expression by a cell. In some embodiments, the RNA complex is an asymmetric shorter-duplex small interfering RNA (an asiRNA). In some embodiments, the RNA complex is an RNA complex listed in Table 1, Table 2, Table 3, Table 4, Table 5, or Table 6. The RNA complexes described herein can contain RNA bases, non-RNA bases or a mixture of RNA bases and non-RNA bases. For example, certain RNA complexes provided herein can be primarily composed of RNA bases but also contain DNA bases or non-naturally occurring nucleotides.

In some embodiments, the antisense strand is at least 19 nucleotides (nt) in length. In some embodiments, the antisense strand is 19 to 21 nt in length (i.e., 19, 20 or 21 nt in length). In some embodiments, at least 13, 14, 15, 16, 17, 18, 19, 20 or 21 nt of the antisense strand are complementary to the ANGPT2 or PDGFB mRNA sequence. Perfect complementarity is not necessary. In some embodiments, the antisense strand is perfectly complementary to the ANGPT2 or PDGFB mRNA sequence.

In some embodiments, the antisense strand is at least 24 nt in length (e.g., at least 25 nt in length, at least 26 nt in length, at least 27 nt in length, at least 28 nt in length, at least 29 nt in length, at least 30 nt in length or at least 31 nt in length). In some embodiments, the antisense strand is no greater than 124 nt in length (e.g., no greater than 100 nt in length, no greater than 90 nt in length, no greater than 80 nt in length, no greater than 70 nt in length, no greater than 60 nt in length, no greater than 50 nt in length or no greater than 40 nt in length. In some embodiments, the antisense strand is 31 nt in length. In some embodiments, at least 16, 17, 18, 19, 20, 21, 22, 23, 24, 25, 26, 27, 29, 29, 30 or 31 nt of the antisense strand are complementary to the ANGPT2 or PDGFB mRNA sequence. Perfect complementarity is not necessary. In some embodiments, the antisense strand is perfectly complementary to the ANGPT2 or PDGFB mRNA sequence.

In some embodiments, the sense strand is 15 to 17 nt in length (i.e., 15 nt in length, 16 nt in length or 17 nt in length). In some embodiments, at least 15 nt, at least 16 nt or at least 17 nt of the sense strand are complementary to the sequence of the antisense strand. In some embodiments the sense strand is perfectly complementary to the sequence of the antisense strand.

In some embodiments, the antisense strand and the sense strand form a complex in which the 5' end of the antisense strand and the 3' end of the sense strand form a blunt end. In some embodiments, the antisense strand and the sense strand form a complex in which the 5' end of the antisense strand overhangs the 3' end of the sense strand (e.g., by 1, 2, 3, 4 or 5 nt). In some embodiments, the antisense strand and the sense strand form a complex in which the 5' end of the sense strand overhangs the 3' end of the antisense strand (e.g., by 1, 2, 3, 4 or 5 nt).

In some embodiments, the antisense strand and/or the sense strand of the RNA complex has a sense strand sequence and/or an antisense strand sequence selected from the sequences listed in Table 1, Table 2, Table 3, Table 4, Table 5, or Table 6. In some embodiments, the RNA complex provided herein comprises a chemical modification, wherein the modification facilitates the penetration of a cellular membrane in the absence of a delivery vehicle.

In some embodiments, the modification is a 2'-O-methylated nucleoside, a phosphorothioate bond, or a hydrophobic moiety. In some embodiments, the RNA complexes provided herein comprise a hydrophobic moiety. In some embodiments, the hydrophobic moiety can be any chemical structure having hydrophobic character. For example, in some embodiments the hydrophobic moiety is a lipid, a lipophilic peptide and/or a lipophilic protein. In some embodiments, the hydrophobic moiety is a lipid, such as cholesterol, tocopherol, or a long-chain fatty acid having 10 or more carbon atoms (e.g., stearic acid or palmitic acid). In some embodiments, the hydrophobic moiety is cholesterol. In some embodiments, the hydrophobic moiety is a cholesterol moiety. In some embodiments, the RNA complex is a modified RNA complex listed in Table 2, Table 3, Table 5, or Table 6. In certain embodiments, the RNA complex is not cytotoxic.

The RNA complexes described herein can employ a variety of oligonucleotide chemistries. Examples of oligonucleotide chemistries include, without limitation, peptide nucleic acid (PNA), linked nucleic acid (LNA), phosphorothioate, 2'O-Me-modified oligonucleotides, and morpholino chemistries, including combinations of any of the foregoing. In general, PNA chemistries can utilize shorter targeting sequences because of their relatively high target binding strength relative to 2'O-Me oligonucleotides. Phosphorothioate and 2'O-Me-modified chemistries are often combined to generate 2'O-Me-modified oligonucleotides having a phosphorothioate backbone. See, e.g., PCT Publication Nos. WO/2013/112053 and WO/2009/008725, each of which is hereby incorporated by reference in its entirety.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition. The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases.

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE™ has developed its proprietary Bts PNA monomers (Bts; benzothiazole-2-sulfonyl group) and proprietary oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969, 766, 7,211,668, 7,022,851, 7,125,994, 7,145,006 and 7,179, 896. See also U.S. Pat. Nos. 5,539,082; 5,714,331; and 5,719,262 for the preparation of PNAs. Further teaching of PNA compounds can be found in Nielsen et al., *Science*, 254:1497-1500, 1991. Each of the foregoing is incorporated by reference in its entirety.

Interfering nucleic acids may also contain "locked nucleic acid" subunits (LNAs). "LNAs" are a member of a class of modifications called bridged nucleic acid (BNA). BNA is characterized by a covalent linkage that locks the conformation of the ribose ring in a C3-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., *Chemical Communications* (1998) 455; *Tetrahedron* (1998) 54:3607, and *Accounts of Chem. Research* (1999) 32:301); Obika, et al., *Tetrahedron Letters* (1997) 38:8735; (1998) 39:5401, and *Bioorganic Medicinal Chemistry* (2008) 16:9230. Compounds provided herein may incorporate one or more LNAs; in some cases, the compounds may be entirely composed of LNAs. Methods for the synthesis of individual LNA nucleoside subunits and their incorporation into oligonucleotides are described, for example, in U.S. Pat. Nos. 7,572,582, 7,569,575, 7,084,125, 7,060,809, 7,053,207, 7,034,133, 6,794,499, and 6,670,461, each of which is incorporated by reference in its entirety. Typical intersubunit linkers include phosphodiester and phosphorothioate moieties; alternatively, non-phosphorous containing linkers may be employed. One embodiment is an LNA-containing compound where each LNA subunit is separated by a DNA subunit. Certain compounds are composed of alternating LNA and DNA subunits where the intersubunit linker is phosphorothioate.

In certain embodiments, the RNA complex is linked to a cholesterol moiety. In some embodiments, the cholesterol moiety is attached to the 3' terminus of the sense strand. In some embodiments, the cholesterol moiety is attached to the 3' terminus of the antisense strand. In some embodiments, the cholesterol moiety is attached to the 5' terminus of the sense strand. In some embodiments, the cholesterol moiety is attached to the 5' terminus of the antisense strand.

In some embodiments, the RNA complex comprises a 2'-O-methylated nucleoside. 2'-O-methylated nucleosides carry a methyl group at the 2'-OH residue of the ribose molecule. 2'-O-Me-RNAs show the same (or similar) behavior as RNA, but are protected against nuclease degradation. 2'-O-Me-RNAs can also be combined with phosphothioate oligonucleotides (PTOs) for further stabilization. 2'-O-Me-RNAs (phosphodiester or phosphothioate) can be synthesized according to routine techniques in the art (see, e.g., Yoo et al., *Nucleic Acids Res.* 32:2008-16, 2004, which is hereby incorporated by reference).

In some embodiments, the 2'-O-methyl nucleoside is positioned at the 3' terminus of the sense strand. In some embodiments, 3' terminal region of the sense strand comprises a plurality of 2'-O-methylated nucleosides (e.g., 2, 3, 4, 5 or 6 2'-O-methylated nucleosides within 6 nucleosides of the 3' terminus). In some embodiments, the 2'-O-methyl nucleoside is positioned at the 3' terminus of the antisense strand. In some embodiments, 3' terminal region of the antisense strand comprises a plurality of 2'-O-methylated nucleosides (e.g., 2, 3, 4, 5 or 6 2'-O-methylated nucleosides within 6 nucleosides of the 3' terminus). In some embodiments, both the 3' terminal region of the sense strand and the 3' terminal region of the antisense strand comprise a plurality of 2'-O-methylated nucleosides. In some embodiments, the sense strand comprises 2'-O-methylated nucleosides that alternate with unmodified nucleosides. In some embodiments, the sense strand comprises a contiguous sequence of 2, 3, 4, 5, 6, 7 or 8 2'-O-methylated nucleosides that alternate with unmodified nucleosides. In some embodiments, the anti-sense strand comprises 2'-O-methylated nucleosides that alternate with unmodified nucleosides. In some embodiments, the anti-sense strand comprises a contiguous sequence of 2, 3, 4, 5, 6, 7 or 8 2'-O-methylated nucleosides that alternate with unmodified nucleosides.

In some embodiments, the RNA complex comprises a phosphorothioate bond. "Phosphorothioates" (or S-oligos) are a variant of normal DNA in which one of the non-bridging oxygen is replaced by a sulfur. The sulfurization of the internucleotide bond reduces the action of endo- and exonucleases including 5' to 3' and 3' to 5' DNA POL 1 exonuclease, nucleases S1 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1,2-benzodithiol-3-one 1,1-dioxide (BDTD) (see, e.g., Iyer et al., *J. Org. Chem.* 55, 4693-4699, 1990). The latter methods avoid the problem of elemental sulfur's insolubility in most organic solvents and the toxicity of carbon disulfide. The TETD and BDTD methods also yield higher purity phosphorothioates.

In some embodiments, at least 25%, 30%, 35%, 40%, 45%, 50%, 55%, 60%, 65%, 70%, 75%, 80%, 85%, 90% or 95% of the bonds between the ribonucleotides in the sense strand of the RNA complex are phosphorothioate bonds. In some embodiments, all of the bonds between the ribonucleotides in the sense strand of the RNA complex are phosphorothioate bonds.

In some embodiments, at least 25%, 30%, 35%, 40%, 45%, 50%, 55%, 60%, 65%, 70%, 75%, 80%, 85%, 90% or 95% of the bonds between the ribonucleotides in the antisense strand of the RNA complex are phosphorothioate bonds. In some embodiments, all of the bonds between the ribonucleotides in the antisense strand of the RNA complex are phosphorothioate bonds.

The RNA complexes described herein may be contacted with a cell or administered to an organism (e.g., a human). Alternatively, constructs and/or vectors encoding the RNA complexes may be contacted with or introduced into a cell or organism. In certain embodiments, a viral, retroviral, or lentiviral vector is used.

The RNA complexes described herein can be prepared by any appropriate method known in the art. For example, in some embodiments, the RNA complexes described herein are prepared by chemical synthesis or in vitro transcription.

Pharmaceutical Compositions:

In certain aspects, provided herein is a pharmaceutical composition comprising an RNA complex provided herein and a pharmaceutically acceptable carrier. In certain embodiments, the pharmaceutical composition is formulated for delivery to the eye (e.g., as an eye drop or an injectable implant or solution). In some embodiments, the pharmaceutical composition is formulated for intravenous delivery. In some embodiments, the pharmaceutical composition is formulated for intratumoral delivery. In some embodiments, the pharmaceutical composition is administered intratumorally. In some embodiments, the pharmaceutical composition is formulated for oral or parenteral delivery.

In some embodiments, the pharmaceutical composition further comprises a second agent for treatment of AMD or DME. In some embodiments, the second agent is ranibizumab. In some embodiments, the second agent is pegaptanib. In some embodiments, the second agent is aflibercept. In some embodiments, the second agent is bevacizumab.

In some embodiments, the pharmaceutical composition further comprises a second agent for treatment of cancer. In certain embodiments, the second therapeutic agent is a chemotherapeutic agent (e.g., alkylating agents or agents with an alkylating action, such as cyclophosphamide (CTX; e.g., CYTOXANφ), chlorambucil (CHL; e.g., LEUKERAN®), cisplatin (Cis P; e.g., PLATINOL®) busulfan (e.g., MYLERAN®), melphalan, carmustine (BCNU), streptozotocin, triethylenemelamine (TEM), mitomycin C, and the like; anti-metabolites, such as methotrexate (MTX), etoposide (VP16; e.g., VEPESID®), 6-mercaptopurine (6MP), 6-thioguanine (6TG), cytarabine (Ara-C), 5-fluorouracil (5-FU), capecitabine (e.g. XELODA®), dacarbazine (DTIC), and the like; antibiotics, such as actinomycin D, doxorubicin (DXR; e.g., ADRIAMYCIN®), daunorubicin (daunomycin), bleomycin, mithramycin and the like; alkaloids, such as vinca alkaloids such as vincristine (VCR), vinblastine, and the like; and other antitumor agents, such as paclitaxel (e.g., TAXOL®) and pactitaxel derivatives, the cytostatic agents, glucocorticoids such as dexamethasone (DEX; e.g., DECADRON®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: amifostine (e.g., ETHYOL®), dactinomycin, mechlorethamine (nitrogen mustard), streptozocin, cyclophosphamide, lomustine (CCNU), doxorubicin lipo (e.g., DOXIL®), gemcitabine (e.g., GEMZAR®), daunorubicin lipo (e.g., DAUNOXOME®), procarbazine, mitomycin, docetaxel (e.g., TAXOTERE®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil).

In some embodiments, the second therapeutic agent is an immune checkpoint inhibitor. Immune Checkpoint inhibition broadly refers to inhibiting the checkpoints that cancer cells can produce to prevent or downregulate an immune response. Examples of immune checkpoint proteins include, but are not limited to, CTLA4, PD-1, PD-L1, PD-L2, A2AR, B7-H3, B7-H4, BTLA, KIR, LAG3, TIM-3 or VISTA. Immune checkpoint inhibitors can be antibodies or antigen binding fragments thereof that bind to and inhibit an immune checkpoint protein. Examples of immune checkpoint inhibitors include, but are not limited to, nivolumab, pembrolizumab, pidilizumab, AMP-224, AMP-514, STI-A1110, TSR-042, RG-7446, BMS-936559, MEDI-4736, MSB-0020718C, AUR-012 and STI-A1010.

In certain embodiments, the pharmaceutical composition does not comprise a transfection vehicle. In some embodiments, the pharmaceutical composition comprises a delivery vehicle (e.g., liposomes, cationic polymers, cell penetrating peptides (CPPs), protein transduction domains (PTDs), antibodies and/or aptamers). In some embodiments, the composition includes a combination of multiple (e.g., two or more) of the RNA complexes described herein.

Methods of preparing these formulations or compositions include the step of bringing into association an RNA complex described herein with the carrier and, optionally, one or more accessory ingredients. In general, the formulations are prepared by uniformly and intimately bringing into association an agent described herein with liquid carriers.

Therapeutic Methods

In certain aspects, provided herein is a method of inhibiting ANGPT2 or PDGFB expression by a cell, comprising contacting the cell with an RNA complex provided herein. In certain aspects, provided herein is a method of inhibiting angiogenesis in a cell, comprising contacting the cell with an RNA complex provided herein. In some embodiments, the RNA complex is a modified RNA complex and the cell is contacted with the RNA complex in the absence of a transfection vehicle. In some embodiments, the cell is contacted with the RNA complex in the presence of a delivery vehicle (e.g., a liposome, cationic polymer, cell penetrating peptide (CPP), protein transduction domain (PTD), antibody and/or aptamer).

In certain aspects, provided herein is a method of inhibiting angiogenesis in a subject, comprising administering the RNA complex or pharmaceutical composition to provided herein to the subject. In certain aspects, provided herein is a method of treating a human subject for AMD, DME, or cancer comprising administering to the subject an RNA complex or pharmaceutical composition provided herein.

In some embodiments, the subject has cancer. In some embodiments, the cancer comprises a solid tumor. In some embodiments, the RNA complex is administered without a delivery vehicle. In some embodiments, the RNA complex or pharmaceutical composition is administered intratumorally. In some embodiments, the RNA complex or pharmaceutical composition is administered intravenously. In some embodiments, the RNA complex or pharmaceutical composition is administered with a second cancer therapeutic agent. In some embodiments, the second cancer therapeutic agent is a chemotherapeutic agent. In some embodiments, the second cancer therapeutic agent is an immune checkpoint inhibitor.

In some embodiments, the RNA complex is administered to the eye of a subject. In some embodiments, the subject has AMD (e.g. wet or dry AMD). In some embodiments, the subject has DME. In some embodiments, the subject is female. In some embodiments, the subject is male. In certain embodiments, the RNA complex or pharmaceutical composition is administered to the eye of the human subject. In certain embodiments, the RNA complex or pharmaceutical composition is an eye drop.

In certain embodiments, the RNA complex or pharmaceutical composition is administered to the tumor of the human subject. In some embodiments, the RNA complex is administered intratumorally. In certain embodiments, the RNA complex or pharmaceutical composition is administered intravenously.

In some embodiments, the RNA complex or pharmaceutical composition self-administered by the subject. In some aspects, provided herein are methods of treating a cancer by administering to a subject an RNA complex and/or a pharmaceutical composition described herein. In some embodiments, the methods described herein may be used to treat any cancerous or pre-cancerous tumor. In some embodiments, the cancer includes a solid tumor. In some embodiments, the tumor and/or a portion of the tumor is has normal or increased angiogenesis. Cancers that may be treated by methods and compositions provided herein include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometrioid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; mammary paget's disease; acinar cell carcinoma; adenosquamous carcinoma; adenocarcinoma w/squamous metaplasia; malignant thymoma; malignant ovarian stromal tumor; malignant thecoma; malignant granulosa cell tumor; and malignant roblastoma; sertoli cell carcinoma; malignant leydig cell tumor; malignant lipid cell tumor; malignant paraganglioma; malignant extra-mammary paraganglioma; pheochromocytoma; glomangiosarcoma; malignant melanoma; amelanotic melanoma; superficial spreading melanoma; malignant melanoma in giant pigmented nevus; epithelioid cell melanoma; malignant blue nevus; sarcoma; fibrosarcoma; malignant fibrous histiocytoma; myxosarcoma; liposarcoma; leiomyosarcoma; rhabdomyosarcoma; embryonal rhabdomyosarcoma; alveolar rhabdomyosarcoma; stromal sarcoma; malignant mixed tumor; mullerian mixed tumor; nephroblastoma; hepatoblastoma; carcinosarcoma; malignant mesenchymoma; malignant brenner tumor; malignant phyllodes tumor; synovial sarcoma; malignant mesothelioma; dysgerminoma; embryonal carcinoma; malignant teratoma; malignant struma ovarii; choriocarcinoma; malignant mesonephroma; hemangiosarcoma; malignant hemangioendothelioma; kaposi's sarcoma; malignant hemangiopericytoma; lymphangiosarcoma; osteosarcoma; juxtacortical osteosarcoma; chondrosarcoma; malignant chondroblastoma; mesenchymal chondrosarcoma; giant cell tumor of bone; ewing's sarcoma; malignant odontogenic tumor; ameloblastic odontosarcoma; malignant ameloblastoma; ameloblastic fibrosarcoma; malignant pinealoma; chordoma; malignant glioma; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; malignant meningioma; neurofibrosarcoma; malignant neurilemmoma; malignant granular cell tumor; malignant lymphoma; Hodgkin's disease; Hodgkin's lymphoma; paragranuloma; small lymphocytic malignant lymphoma; diffuse large cell malignant lymphoma; follicular malignant lymphoma; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In the present methods, an RNA complex described herein can be administered to the subject, for example, as nucleic acid without delivery vehicle (e.g., for cp-asiRNAs), in combination with a delivery reagent, and/or as a nucleic acid comprising sequences that express the RNA complex described herein. In some embodiments, any nucleic acid delivery method known in the art can be used in the methods described herein. Suitable delivery reagents include, but are not limited to, e.g., the Mirus Transit TKO lipophilic reagent; lipofectin; lipofectamine; cellfectin; polycations (e.g., polylysine), atelocollagen, nanoplexes and liposomes. The use of atelocollagen as a delivery vehicle for nucleic acid molecules is described in Minakuchi et al. *Nucleic*

Acids Res., 32(13):e109 (2004); Hanai et al. *Ann NY Acad Sci.*, 1082:9-17 (2006); and Kawata et al. *Mol Cancer Ther.*, 7(9):2904-12 (2008); each of which is incorporated herein in their entirety. Exemplary interfering nucleic acid delivery systems are provided in U.S. Pat. Nos. 8,283,461, 8,313,772, 8,501,930. 8,426,554, 8,268,798 and 8,324,366, each of which is hereby incorporated by reference in its entirety.

In some embodiments of the methods described herein, liposomes are used to deliver an RNA complex described herein to a subject. Liposomes suitable for use in the methods described herein can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are herein incorporated by reference.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure.

Opsonization-inhibiting moieties for use in preparing the liposomes described herein are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is herein incorporated by reference.

In some embodiments, opsonization inhibiting moieties suitable for modifying liposomes are water-soluble polymers with a number-average molecular weight from about 500 to about 40,000 daltons, or from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. In some embodiments, the opsonization-inhibiting moiety is a PEG, PPG, or derivatives thereof. Liposomes modified with PEG or PEG-derivatives are sometimes called "PEGylated liposomes."

The pharmaceutical compositions disclosed herein may be delivered by any suitable route of administration, including intravenously, intratumorally, intraocularly, orally, and parenterally. In certain embodiments, the pharmaceutical compositions are delivered systemically (e.g., via oral or intravenous administration). In certain other embodiments, the pharmaceutical compositions are delivered locally to the eye through injection (e.g., intravitreally) or through an eye drop.

Actual dosage levels of the RNA complexes in the pharmaceutical compositions may be varied so as to obtain an amount of RNA complex that is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician having ordinary skill in the art can readily determine and prescribe the effective amount of the pharmaceutical composition required. For example, the physician or veterinarian could prescribe and/or administer doses of the agents employed in the pharmaceutical composition at levels lower than that required in order to achieve the desired therapeutic effect and gradually increase the dosage until the desired effect is achieved.

In general, a suitable daily dose of an RNA complex described herein will be that amount of the RNA complex which is the lowest dose effective to produce a therapeutic effect. Such an effective dose will generally depend upon the factors described above.

EXEMPLIFICATION

Example 1: Screening for ANGPT2-Targeting Asymmetric Shorter-Duplex Small Interfering RNAs To identify asymmetric shorter-duplex small interfering RNAs (asiRNAs) that inhibit ANGPT2 with high efficiency, 100 asiRNAs were synthesized and screened. The nucleic acid sequences of screened asiRNAs are provided in Table 1.

TABLE 1

Nucleic acid sequences for exemplary ANGPT2-targeting asiRNA.

| SEQ ID NO: | SEQUENCE |
|---|---|
| 1 | ANGPT2#1(AS): 5' UGUCAGUAUCCGAAUCAAUCA 3' |
| 2 | ANGPT2#1(S): 5' GAUUCGGAUACUGACA 3' |
| 3 | ANGPT2#2(AS): 5' GUGUCAGUAUCCGAAUCAAUC 3' |

TABLE 1-continued

Nucleic acid sequences for exemplary ANGPT2-targeting asiRNA.

| SEQ ID NO: | SEQUENCE |
|---|---|
| 4 | ANGPT2#2(S): 5' AUUCGGAUACUGACAC 3' |
| 5 | ANGPT2#3(AS): 5' AGUGUCAGUAUCCGAAUCAAU 3' |
| 6 | ANGPT2#3(S): 5' UUCGGAUACUGACACU 3' |
| 7 | ANGPT2#4(AS): 5' CAGUGUCAGUAUCCGAAUCAA 3' |
| 8 | ANGPT2#4(S): 5' UCGGAUACUGACACUG 3' |
| 9 | ANGPT2#5(AS): 5' ACAGUGUCAGUAUCCGAAUCA 3' |
| 10 | ANGPT2#5(S): 5' CGGAUACUGACACUGU 3' |
| 11 | ANGPT2#6(AS): 5' UACAGUGUCAGUAUCCGAAUC 3' |
| 12 | ANGPT2#6(S): 5' GGAUACUGACACUGUA 3' |
| 13 | ANGPT2#7(AS): 5' CUACAGUGUCAGUAUCCGAAU 3' |
| 14 | ANGPT2#7(S): 5' GAUACUGACACUGUAG 3' |
| 15 | ANGPT2#8(AS): 5' UACUUGGGCUUCCACAUCAGU 3' |
| 16 | ANGPT2#8(S): 5' UGUGGAAGCCCAAGUA 3' |
| 17 | ANGPT2#9(AS): 5' GUCACAGUAGGCCUUGAUCUC 3' |
| 18 | ANGPT2#9(S): 5' CAAGGCCUACUGUGAC 3' |
| 19 | ANGPT2#10(AS): 5' UGUCACAGUAGGCCUUGAUCU 3' |
| 20 | ANGPT2#10(S): 5' AAGGCCUACUGUGACA 3' |
| 21 | ANGPT2#11(AS): 5' AUGUCACAGUAGGCCUUGAUC 3' |
| 22 | ANGPT2#11(S): 5' AGGCCUACUGUGACAU 3' |
| 23 | ANGPT2#12(AS): 5' CAUGUCACAGUAGGCCUUGAU 3' |
| 24 | ANGPT2#12(S): 5' GGCCUACUGUGACAUG 3' |
| 25 | ANGPT2#13(AS): 5' CCAUGUCACAGUAGGCCUUGA 3' |
| 26 | ANGPT2#13(S): 5' GCCUACUGUGACAUGG 3' |
| 27 | ANGPT2#14(AS): 5' UCCAUGUCACAGUAGGCCUUG 3' |
| 28 | ANGPT2#14(S): 5' CCUACUGUGACAUGGA 3' |
| 29 | ANGPT2#15(AS): 5' CAAGUUGGAAGGACCACAUGC 3' |
| 30 | ANGPT2#15(S): 5' UGGUCCUUCCAACUUG 3' |
| 31 | ANGPT2#16(AS): 5' UCAAGUUGGAAGGACCACAUG 3' |
| 32 | ANGPT2#16(S): 5' GGUCCUUCCAACUUGA 3' |
| 33 | ANGPT2#17(AS): 5' UUCAAGUUGGAAGGACCACAU 3' |
| 34 | ANGPT2#17(S): 5' GUCCUUCCAACUUGAA 3' |
| 35 | ANGPT2#18(AS): 5' CAUGGUUGUGGCCUUGAGCGA 3' |
| 36 | ANGPT2#18(S): 5' CAAGGCCACAACCAUG 3' |
| 37 | ANGPT2#19(AS): 5' UCAUGGUUGUGGCCUUGAGCG 3' |
| 38 | ANGPT2#19(S): 5' AAGGCCACAACCAUGA 3' |
| 39 | ANGPT2#20(AS): 5' AUCAUGGUUGUGGCCUUGAGC 3' |
| 40 | ANGPT2#20(S): 5' AGGCCACAACCAUGAU 3' |
| 41 | ANGPT2#21(AS): 5' CAUCAUGGUUGUGGCCUUGAG 3' |
| 42 | ANGPT2#21(S): 5' GGCCACAACCAUGAUG 3' |
| 43 | ANGPT2#22(AS): 5' UCAUCAUGGUUGUGGCCUUGA 3' |
| 44 | ANGPT2#22(S): 5' GCCACAACCAUGAUGA 3' |
| 45 | ANGPT2#23(AS): 5' AUCAUCAUGGUUGUGGCCUUG 3' |
| 46 | ANGPT2#23(S): 5' CCACAACCAUGAUGAU 3' |
| 47 | ANGPT2#24(AS): 5' GAUCAUCAUGGUUGUGGCCUU 3' |
| 48 | ANGPT2#24(S): 5' CACAACCAUGAUGAUC 3' |
| 49 | ANGPT2#25(AS): 5' GGAUCAUCAUGGUUGUGGCCU 3' |
| 50 | ANGPT2#25(S): 5' ACAACCAUGAUGAUCC 3' |
| 51 | ANGPT2#26(AS): 5' CGGAUCAUCAUGGUUGUGGCC 3' |
| 52 | ANGPT2#26(S): 5' CAACCAUGAUGAUCCG 3' |
| 53 | ANGPT2#27(AS): 5' CUGUUUUCCAGUUAUUUACUG 3' |
| 54 | ANGPT2#27(S): 5' AAUAACUGGAAAACAG 3' |
| 55 | ANGPT2#28(AS): 5' GUGUUCUGUUUUCCAGUUAUU 3' |
| 56 | ANGPT2#28(S): 5' CUGGAAAACAGAACAC 3' |
| 57 | ANGPT2#29(AS): 5' AGUGUUCUGUUUUCCAGUUAU 3' |
| 58 | ANGPT2#29(S): 5' UGGAAAACAGAACACU 3' |
| 59 | ANGPT2#30(AS): 5' AAGUGUUCUGUUUUCCAGUUA 3' |
| 60 | ANGPT2#30(S): 5' GGAAAACAGAACACUU 3' |
| 61 | ANGPT2#31(AS): 5' UAAGUGUUCUGUUUUCCAGUU 3' |
| 62 | ANGPT2#31(S): 5' GAAAACAGAACACUUA 3' |
| 63 | ANGPT2#32(AS): 5' GUCAGUAUCCGAAUCAAUCAC 3' |
| 64 | ANGPT2#32(S): 5' UGAUUCGGAUACUGAC 3' |
| 65 | ANGPT2#33(AS): 5' CCUACAGUGUCAGUAUCCGAA 3' |
| 66 | ANGPT2#33(S): 5' AUACUGACACUGUAGG 3' |
| 67 | ANGPT2#34(AS): 5' UAGGCUGCGGCCAAGACAAGA 3' |
| 68 | ANGPT2#34(S): 5' UCUUGGCCGCAGCCUA 3' |
| 69 | ANGPT2#35(AS): 5' AUUGGACACGUAGGGGCUGGA 3' |
| 70 | ANGPT2#35(S): 5' CCCCUACGUGUCCAAU 3' |
| 71 | ANGPT2#36(AS): 5' UCCCUCUGCACAGCAUGGAC 3' |
| 72 | ANGPT2#36(S): 5' AUGCUGUGCAGAGGGA 3' |
| 73 | ANGPT2#37(AS): 5' GUUCUCCAGCACUUGCAGCCU 3' |
| 74 | ANGPT2#37(S): 5' GCAAGUGCUGGAGAAC 3' |
| 75 | ANGPT2#38(AS): 5' UGUUCUCCAGCACUUGCAGCC 3' |
| 76 | ANGPT2#38(S): 5' CAAGUGCUGGAGAACA 3' |
| 77 | ANGPT2#39(AS): 5' AUGUUCUCCAGCACUUGCAGC 3' |

TABLE 1-continued

Nucleic acid sequences for exemplary ANGPT2-targeting asiRNA.

| SEQ ID NO: | SEQUENCE |
|---|---|
| 78 | ANGPT2#39(S): 5' AAGUGCUGGAGAACAU 3' |
| 79 | ANGPT2#40(AS): 5' UCAUCACAGCCGUCUGGUUCU 3' |
| 80 | ANGPT2#40(S): 5' CAGACGGCUGUGAUGA 3' |
| 81 | ANGPT2#41(AS): 5' AUCAUCACAGCCGUCUGGUUC 3' |
| 82 | ANGPT2#41(S): 5' AGACGGCUGUGAUGAU 3' |
| 83 | ANGPT2#42(AS): 5' UAUCAUCACAGCCGUCUGGUU 3' |
| 84 | ANGPT2#42(S): 5' GACGGCUGUGAUGAUA 3' |
| 85 | ANGPT2#43(AS): 5' CUAUCAUCACAGCCGUCUGGU 3' |
| 86 | ANGPT2#43(S): 5' ACGGCUGUGAUGAUAG 3' |
| 87 | ANGPT2#44(AS): 5' UCUAUCAUCACAGCCGUCUGG 3' |
| 88 | ANGPT2#44(S): 5' CGGCUGUGAUGAUAGA 3' |
| 89 | ANGPT2#45(AS): 5' UUCUAUCAUCACAGCCGUCUG 3' |
| 90 | ANGPT2#45(S): 5' GGCUGUGAUGAUAGAA 3' |
| 91 | ANGPT2#46(AS): 5' UUUCUAUCAUCACAGCCGUCU 3' |
| 92 | ANGPT2#46(S): 5' GCUGUGAUGAUAGAAA 3' |
| 93 | ANGPT2#47(AS): 5' ACUUGGGCUUCCACAUCAGUU 3' |
| 94 | ANGPT2#47(S): 5' AUGUGGAAGCCCAAGU 3' |
| 95 | ANGPT2#48(AS): 5' AUACUUGGGCUUCCACAUCAG 3' |
| 96 | ANGPT2#48(S): 5' GUGGAAGCCCAAGUAU 3' |
| 97 | ANGPT2#49(AS): 5' ACUGGUCUGGUCCAAAAUCUG 3' |
| 98 | ANGPT2#49(S): 5' UUUGGACCAGACCAGU 3' |
| 99 | ANGPT2#50(AS): 5' UUCACUGGUCUGGUCCAAAAU 3' |
| 100 | ANGPT2#50(S): 5' GGACCAGACCAGUGAA 3' |
| 101 | ANGPT2#51(AS): 5' UUUCACUGGUCUGGUCCAAAA 3' |
| 102 | ANGPT2#51(S): 5' GACCAGACCAGUGAAA 3' |
| 103 | ANGPT2#52(AS): 5' AUUUCACUGGUCUGGUCCAAA 3' |
| 104 | ANGPT2#52(S): 5' ACCAGACCAGUGAAAU 3' |
| 105 | ANGPT2#53(AS): 5' UAUUUCACUGGUCUGGUCCAA 3' |
| 106 | ANGPT2#53(S): 5' CCAGACCAGUGAAAUA 3' |
| 107 | ANGPT2#54(AS): 5' UUAUUUCACUGGUCUGGUCCA 3' |
| 108 | ANGPT2#54(S): 5' CAGACCAGUGAAAUAA 3' |
| 109 | ANGPT2#55(AS): 5' UUUAUUUCACUGGUCUGGUCC 3' |
| 110 | ANGPT2#55(S): 5' AGACCAGUGAAAUAAA 3' |
| 111 | ANGPT2#56(AS): 5' GUUUAUUUCACUGGUCUGGUC 3' |
| 112 | ANGPT2#56(S): 5' GACCAGUGAAAUAAAC 3' |
| 113 | ANGPT2#57(AS): 5' UGUUUAUUUCACUGGUCUGGU 3' |
| 114 | ANGPT2#57(S): 5' ACCAGUGAAAUAAACA 3' |
| 115 | ANGPT2#58(AS): 5' UUGUUUAUUUCACUGGUCUGG 3' |
| 116 | ANGPT2#58(S): 5' CCAGUGAAAUAAACAA 3' |
| 117 | ANGPT2#59(AS): 5' UUUGUUUAUUUCACUGGUCUG 3' |
| 118 | ANGPT2#59(S): 5' CAGUGAAAUAAACAAA 3' |
| 119 | ANGPT2#60(AS): 5' AGUAGGCCUUGAUCUCUUCUG 3' |
| 120 | ANGPT2#60(S): 5' GAGAUCAAGGCCUACU 3' |
| 121 | ANGPT2#61(AS): 5' CAGUAGGCCUUGAUCUCUUCU 3' |
| 122 | ANGPT2#61(S): 5' AGAUCAAGGCCUACUG 3' |
| 123 | ANGPT2#62(AS): 5' ACAGUAGGCCUUGAUCUCUUC 3' |
| 124 | ANGPT2#62(S): 5' GAUCAAGGCCUACUGU 3' |
| 125 | ANGPT2#63(AS): 5' CACAGUAGGCCUUGAUCUCUU 3' |
| 126 | ANGPT2#63(S): 5' AUCAAGGCCUACUGUG 3' |
| 127 | ANGPT2#64(AS): 5' UCACAGUAGGCCUUGAUCUCU 3' |
| 128 | ANGPT2#64(S): 5' UCAAGGCCUACUGUGA 3' |
| 129 | ANGPT2#65(AS): 5' UUCCAUGUCACAGUAGGCCUU 3' |
| 130 | ANGPT2#65(S): 5' CUACUGUGACAUGGAA 3' |
| 131 | ANGPT2#66(AS): 5' GCUGAUGCUGCUUAUUUGCC 3' |
| 132 | ANGPT2#66(S): 5' AAUAAGCAGCAUCAGC 3' |
| 133 | ANGPT2#67(AS): 5' UGGCUGAUGCUGCUUAUUUG 3' |
| 134 | ANGPT2#67(S): 5' UAAGCAGCAUCAGCCA 3' |
| 135 | ANGPT2#68(AS): 5' UUGGCUGAUGCUGCUUAUUUU 3' |
| 136 | ANGPT2#68(S): 5' AAGCAGCAUCAGCCAA 3' |
| 137 | ANGPT2#69(AS): 5' UGGUUGGCUGAUGCUGCUUAU 3' |
| 138 | ANGPT2#69(S): 5' CAGCAUCAGCCAACCA 3' |
| 139 | ANGPT2#70(AS): 5' CUGGUUGGCUGAUGCUGCUUA 3' |
| 140 | ANGPT2#70(S): 5' AGCAUCAGCCAACCAG 3' |
| 141 | ANGPT2#71(AS): 5' UUCCUGGUUGGCUGAUGCUGC 3' |
| 142 | ANGPT2#71(S): 5' AUCAGCCAACCAGGAA 3' |
| 143 | ANGPT2#72(AS): 5' AAAAUCAUUCCUGGUUGGCU 3' |
| 144 | ANGPT2#72(S): 5' ACCAGGAAAUGAUUUU 3' |
| 145 | ANGPT2#73(AS): 5' UAAAAUCAUUCCUGGUUGGC 3' |
| 146 | ANGPT2#73(S): 5' CCAGGAAAUGAUUUUA 3' |
| 147 | ANGPT2#74(AS): 5' CUAAAAUCAUUCCUGGUUGG 3' |
| 148 | ANGPT2#74(S): 5' CAGGAAAUGAUUUUAG 3' |
| 149 | ANGPT2#75(AS): 5' GCUAAAAUCAUUCCUGGUUG 3' |
| 150 | ANGPT2#75(S): 5' AGGAAAUGAUUUUAGC 3' |
| 151 | ANGPT2#76(AS): 5' UGCUAAAAUCAUUCCUGGUU 3' |

TABLE 1-continued

Nucleic acid sequences for exemplary ANGPT2-targeting asiRNA.

| SEQ ID NO: | SEQUENCE |
|---|---|
| 152 | ANGPT2#76(S): 5' GGAAAUGAUUUUAGCA 3' |
| 153 | ANGPT2#77(AS): 5' CUUUGUGCUAAAAUCAUUCC 3' |
| 154 | ANGPT2#77(S): 5' UGAUUUUAGCACAAAG 3' |
| 155 | ANGPT2#78(AS): 5' CCUUUGUGCUAAAAUCAUUC 3' |
| 156 | ANGPT2#78(S): 5' GAUUUUAGCACAAAGG 3' |
| 157 | ANGPT2#79(AS): 5' AAGGACCACAUGCAUCAAACC 3' |
| 158 | ANGPT2#79(S): 5' GAUGCAUGUGGUCCUU 3' |
| 159 | ANGPT2#80(AS): 5' GAAGGACCACAUGCAUCAAAC 3' |
| 160 | ANGPT2#80(S): 5' AUGCAUGUGGUCCUUC 3' |
| 161 | ANGPT2#81(AS): 5' UGGAAGGACCACAUGCAUCAA 3' |
| 162 | ANGPT2#81(S): 5' GCAUGUGGUCCUUCCA 3' |
| 163 | ANGPT2#82(AS): 5' UUGGAAGGACCACAUGCAUCA 3' |
| 164 | ANGPT2#82(S): 5' CAUGUGGUCCUUCCAA 3' |
| 165 | ANGPT2#83(AS): 5' GUUGGAAGGACCACAUGCAUC 3' |
| 166 | ANGPT2#83(S): 5' AUGUGGUCCUUCCAAC 3' |
| 167 | ANGPT2#84(AS): 5' AGUUGGAAGGACCACAUGCAU 3' |
| 168 | ANGPT2#84(S): 5' UGUGGUCCUUCCAACU 3' |
| 169 | ANGPT2#85(AS): 5' AAGUUGGAAGGACCACAUGCA 3' |
| 170 | ANGPT2#85(S): 5' GUGGUCCUUCCAACUU 3' |
| 171 | ANGPT2#86(AS): 5' GUUCAAGUUGGAAGGACCACA 3' |
| 172 | ANGPT2#86(S): 5' UCCUUCCAACUUGAAC 3' |
| 173 | ANGPT2#87(AS): 5' UUGUGGCCUUGAGCGAAUAGC 3' |
| 174 | ANGPT2#87(S): 5' UCGCUCAAGGCCACAA 3' |
| 175 | ANGPT2#88(AS): 5' GUUGUGGCCUUGAGCGAAUAG 3' |
| 176 | ANGPT2#88(S): 5' CGCUCAAGGCCACAAC 3' |
| 177 | ANGPT2#89(AS): 5' GGUUGUGGCCUUGAGCGAAUA 3' |
| 178 | ANGPT2#89(S): 5' GCUCAAGGCCACAACC 3' |
| 179 | ANGPT2#90(AS): 5' UGGUUGUGGCCUUGAGCGAAU 3' |
| 180 | ANGPT2#90(S): 5' CUCAAGGCCACAACCA 3' |
| 181 | ANGPT2#91(AS): 5' AUGGUUGUGGCCUUGAGCGAA 3' |
| 182 | ANGPT2#91(S): 5' UCAAGGCCACAACCAU 3' |
| 183 | ANGPT2#92(AS): 5' UCGGAUCAUCAUGGUUGUGGC 3' |
| 184 | ANGPT2#92(S): 5' AACCAUGAUGAUCCGA 3' |
| 185 | ANGPT2#93(AS): 5' AAUCGCUGGUCGGAUCAUCA 3' |
| 186 | ANGPT2#93(S): 5' AUCCGACCAGCAGAUU 3' |
| 187 | ANGPT2#94(AS): 5' AAAUCUGCUGGUCGGAUCAUC 3' |
| 188 | ANGPT2#94(S): 5' UCCGACCAGCAGAUUU 3' |
| 189 | ANGPT2#95(AS): 5' GAAAUCUGCUGGUCGGAUCAU 3' |
| 190 | ANGPT2#95(S): 5' CCGACCAGCAGAUUUC 3' |
| 191 | ANGPT2#96(AS): 5' AGAAAUCUGCUGGUCGGAUCA 3' |
| 192 | ANGPT2#96(S): 5' CGACCAGCAGAUUUCU 3' |
| 193 | ANGPT2#97(AS): 5' UAGAAAUCUGCUGGUCGGAUC 3' |
| 194 | ANGPT2#97(S): 5' GACCAGCAGAUUUCUA 3' |
| 195 | ANGPT2#98(AS): 5' UUAGAAAUCUGCUGGUCGGAU 3' |
| 196 | ANGPT2#98(S): 5' ACCAGCAGAUUUCUAA 3' |
| 197 | ANGPT2#99(AS): 5' UUUAGAAAUCUGCUGGUCGGA 3' |
| 198 | ANGPT2#99(S): 5' CCAGCAGAUUUCUAAA 3' |
| 199 | ANGPT2#100(AS): 5' AUAAGUGUUCUGUUUUCCAGU 3' |
| 200 | ANGPT2#100(S): 5' AAAACAGAACACUUAU 3' |

The asiRNAs listed in Table 1 were incubated at 95° C. for 5 minutes and at 37° C. for 1 hour in 1× siRNA duplex buffer (Bioneer Inc., Korea). Proper strand annealing was confirmed via gel electrophoresis. For the screen, SK-N-SH cells (ATCC) that had been cultured in Minimum Essential medium (Gibco) containing 10% fetal bovine serum (Gibco) and 100 μg/ml penicillin/streptomycin in a 100 mm cell culture dish. One day prior to transfection, 5×10³ SK-N-SH cells were seeded in 96-well plates. The SK-N-SH cells were transfected with 0.1 nM of the asiRNAs using RNAiMAX (Invitrogen) according to the manufacturer's instructions.

The ANGPT2 mRNA levels in the transfected cells were measured 24 hours after transfection using real-time PCR. Specifically, total RNA was extracted and synthesized the cDNA using SuperPrep Cell Lysis & RT Kit for qPCR (TOYOBO), according to the manufacturer's instructions. Real-time PCR was performed using THUNDERBIRD® Probe qPCR Mix (TOYOBO) according to manufacturer's instructions. Amplification of the ANGPT2 was detected using ANGPT2 TaqMan® Probe (Hs01048042_m1). 18S was amplified as an internal control using 18S TaqMan® Probe (Hs03928985_g1).

The level of ANGPT2 inhibition by each of the 100 asiRNAs is provided in FIG. 1. 27 of the asiRNA sequences which have good RNAi efficacy (>30%), asiANGPT2 #15, #16, #18, #19, #20, #23, #24, #31, #37, #38, #39, #44, #50, #54, #55, #58, #61, #63, #71, #72, #80, #81, #83, #87, #93, #94 and #95 were selected for use in follow-up studies.

Example 2: Inhibition of ANGPT2 mRNA Expression Using ANGPT2-Targeting asiRNAs

Twenty-seven of the asiRNA sequences, asiANGPT2 #15, #16, #18, #19, #20, #23, #24, #31, #37, #38, #39, #44, #50, #54, #55, #58, #61, #63, #71, #72, #80, #81, #83, #87, #93, #94 and #95 were tested for their ability to inhibit ANGPT2 expression.

asiRNAs were incubated at 95° C. for 5 minutes and at 37° C. for 1 hour in 1× siRNA duplex buffer (Bioneer). Proper strand annealing was confirmed via gel electrophoresis. For the screen, SK-N-SH cells (ATCC) were cultured in Minimum Essential medium (Gibco) containing 10% fetal bovine serum (Gibco) and 100 µg/ml penicillin/streptomycin in a 100 mm cell culture dish. One day prior to transfection, 2.5×10$^4$ SK-N-SH cells were seeded in 24-well plates. The SK-N-SH cells were transfected with asiRNAs using RNAiMAX (Invitrogen) according to the manufacturer's instructions.

Specifically, total RNA was extracted using RNAiso Plus (TaKaRa), and then 500 ng of the extracted RNA was used for cDNA synthesis using the high-capacity cDNA reverse transcription kit (Applied Biosystems), according to the manufacturer's instructions. Amplification of the ANGPT2 gene was detected using a power SYBR Premix Ex Taq (TaKaRa). GAPDH was amplified as an internal control. The following primer sequences were used:

```
Human GAPDH-forward
                                  (SEQ ID NO: 201)
5'-GAG TCA ACG GAT TTG GTC GT-3'

Human GAPDH-reverse
                                  (SEQ ID NO: 202)
5'-GAC AAG CTT CCC GTT CTC AG-3'

Human ANGPT2-forward
                                  (SEQ ID NO: 203)
5'-GCA AGT GCT GGA GAA CAT CA-3'

Human ANGPT2-reverse
                                  (SEQ ID NO: 204)
5'-CAC AGC CGT CTG GTT CTG TA-3'
```

Figure 2:
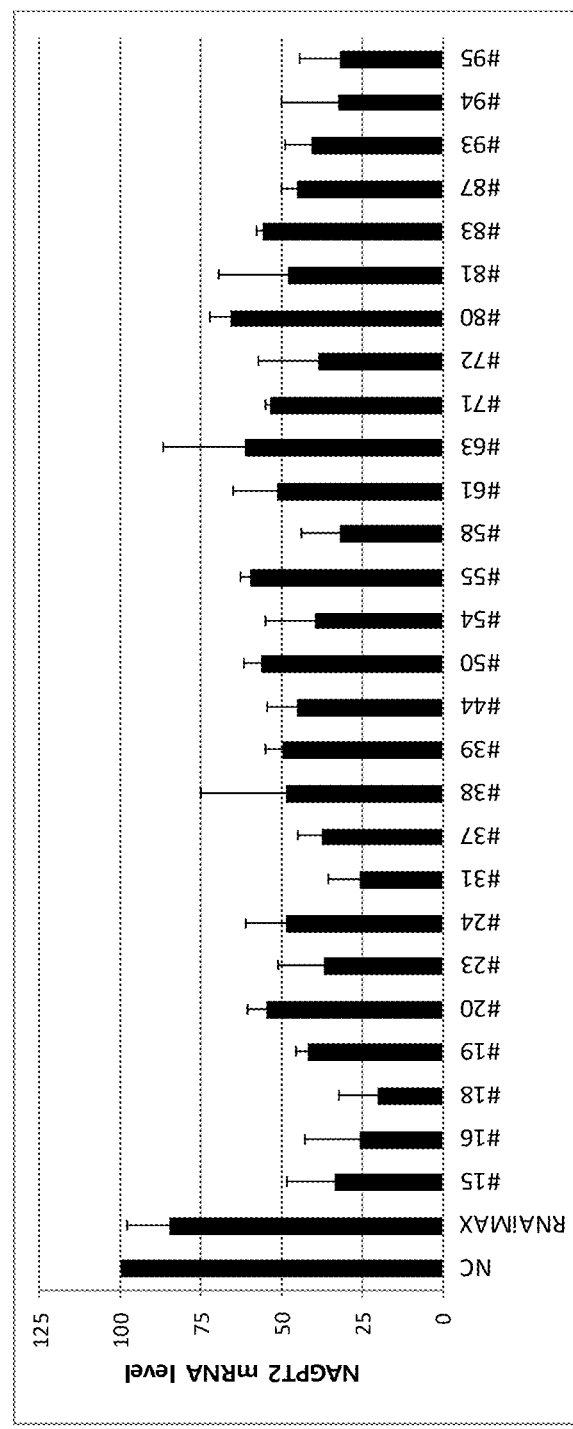
FIG. 2 shows the gene silencing efficiency of 27 exemplary asiRNAs that target ANGPT2.

The level of ANGPT2 inhibition of 27 asiRNAs is provided in FIG. 2.

As shown in FIG. 2, the most efficient 14 asiRNAs; asiANGPT2 #15, #16, #18, #19, #23, #31, #37, #44, #54, #58, #72, #87, #93 and #94 were selected for use in follow-up studies.

Example 3: Inhibition of ANGPT2 mRNA Expression Using ANGPT2-Targeting asiRNAs 14 of the asiRNA sequences, asiANGPT2#15, #16, #18, #19, #23, #31, #37, #44, #54, #58, #72, #87, #93 and #94 were tested for their ability to inhibit ANGPT2 expression by transfection at 1 nM.

The asiRNAs were incubated at 95° C. for 5 minutes and at 37° C. for 1 hour in 1× siRNA duplex buffer (Bioneer). Proper strand annealing was confirmed via gel electrophoresis. For the screen, SK-N-SH cells (ATCC) that had been cultured in Minimum Essential medium (Gibco) containing 10% fetal bovine serum (Gibco) and 100 µg/ml penicillin/ streptomycin in a 100 mm cell culture dish. One day prior to transfection, 2.5×10$^4$ SK-N-SH cells were seeded in 24-well plates. The SK-N-SH cells were transfected with asiRNAs using RNAiMAX (Invitrogen) according to the manufacturer's instructions.

Specifically, total RNA was extracted using RNAiso Plus (TaKaRa), and then 500 ng of the extracted RNA was used for cDNA synthesis using the High-capacity cDNA reverse transcription kit (Applied Biosystems), according to the manufacturer's instructions. Amplification of the ANGPT2 gene was detected using a power SYBR Premix Ex Taq (TaKaRa). GAPDH was an internal control.

Figure 3:
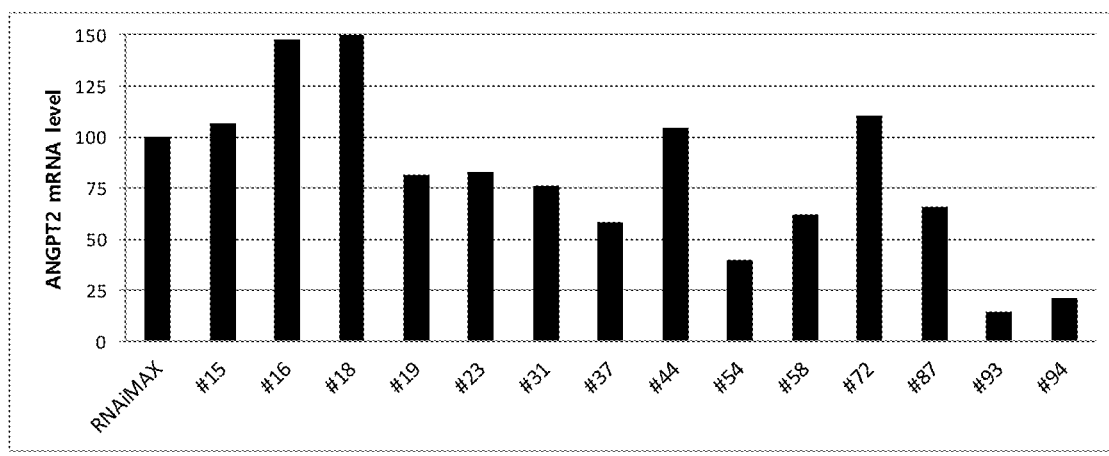
FIG. 3 shows the gene silencing effects of 14 exemplary asiRNAs that target ANGPT2.

The level of ANGPT2 inhibition of 14 asiRNAs is provided in FIG. 3.

Example 4: Inhibition of ANGPT2 Protein Expression Using ANGPT2-Targeting asiRNAs The efficacy of asiANGPT2 for the inhibition of ANGPT2 protein was tested.

asiRNAs were incubated at 95° C. for 5 minutes and at 37° C. for 1 hour in 1× siRNA duplex buffer (Bioneer). Proper strand annealing was confirmed via gel electrophoresis.

SK-N-SH cells (ATCC) that had been cultured in Minimum Essential medium (Gibco) containing 10% fetal bovine serum (Gibco) and 100 µg/ml penicillin/streptomycin in a 100 mm cell culture dish. One day prior to transfection, 2.5×10$^4$ SK-N-SH cells were seeded in 24-well plates. SK-N-SH cells were transfected with 1 nM of the asiRNAs using RNAiMAX (Invitrogen) according to the manufacturer's instructions.

48 hours post asiRNA transfection, the level of ANGPT2 protein expression was determined via western blot. The transfected SK-N-SH cells were lysed with SDS lysis buffer (1% SDS, 100 mM Tris (pH 8.8)). 10 µg of the total protein extracts of SK-N-SH cells were loaded onto a 9% SDS-PAGE gel and electrophoresed at 120 V. After electrophoresis, the proteins were transferred to a PVDF membrane (Bio-rad) previously activated by methanol (Merck) for 1 hour at 300 mA. The membrane was blocked for 1 hour at the room temperature with 3% BSA (Bioworld) and then incubated overnight at 4° C. in 3% BSA containing anti-ANGPT2 antibody (Santa Cruz) and anti-GAPDH antibody (Santa Cruz). The membrane was then washed with 1×TBST for 10 minutes three times and was incubated for 1 hour at the room temperature in 1×TBST with HRP-conjugated secondary antibody. The membrane was washed with 1×TBST for 10 minutes and treated with 1×ECL for 1 minute. ANGPT2 and GAPDH bands were then imaged using a Chemidoc instrument (Bio-rad).

Figure 4:
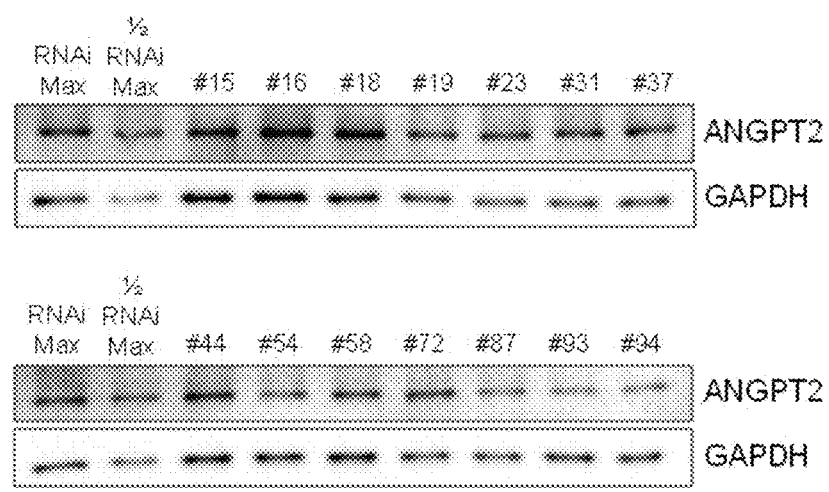
FIG. 4 shows the inhibition of ANGPT2 protein expression by 14 exemplary asiRNAs that target ANGPT2.
Figure 5:
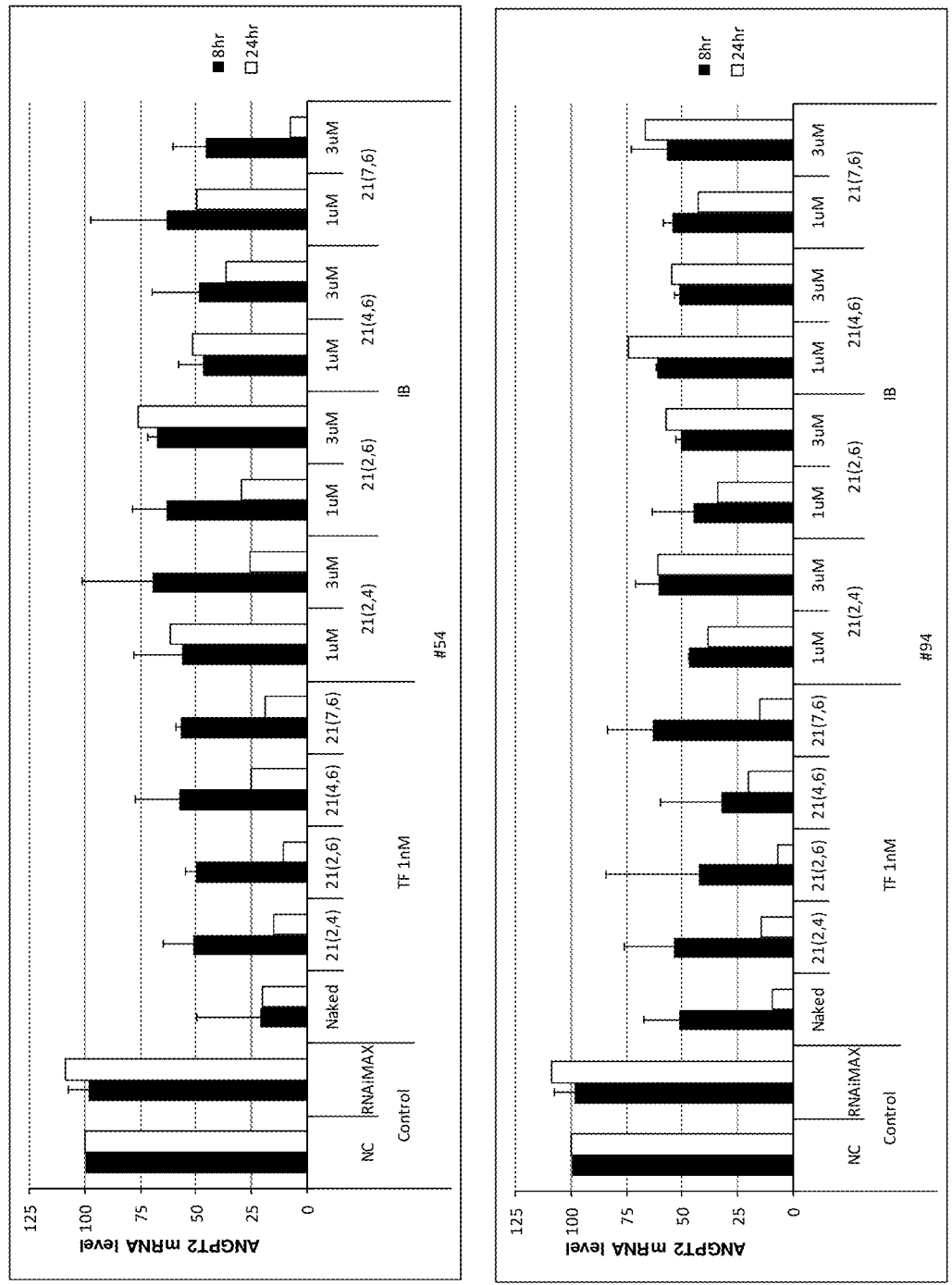
FIG. 5 shows the gene silencing efficiency of exemplary ANGPT2-targeting cell-penetrating asiRNAs (cp-asiRNAs, or cp-asiANGPT2s) to which various chemical modifications have been applied.
Figure 6:
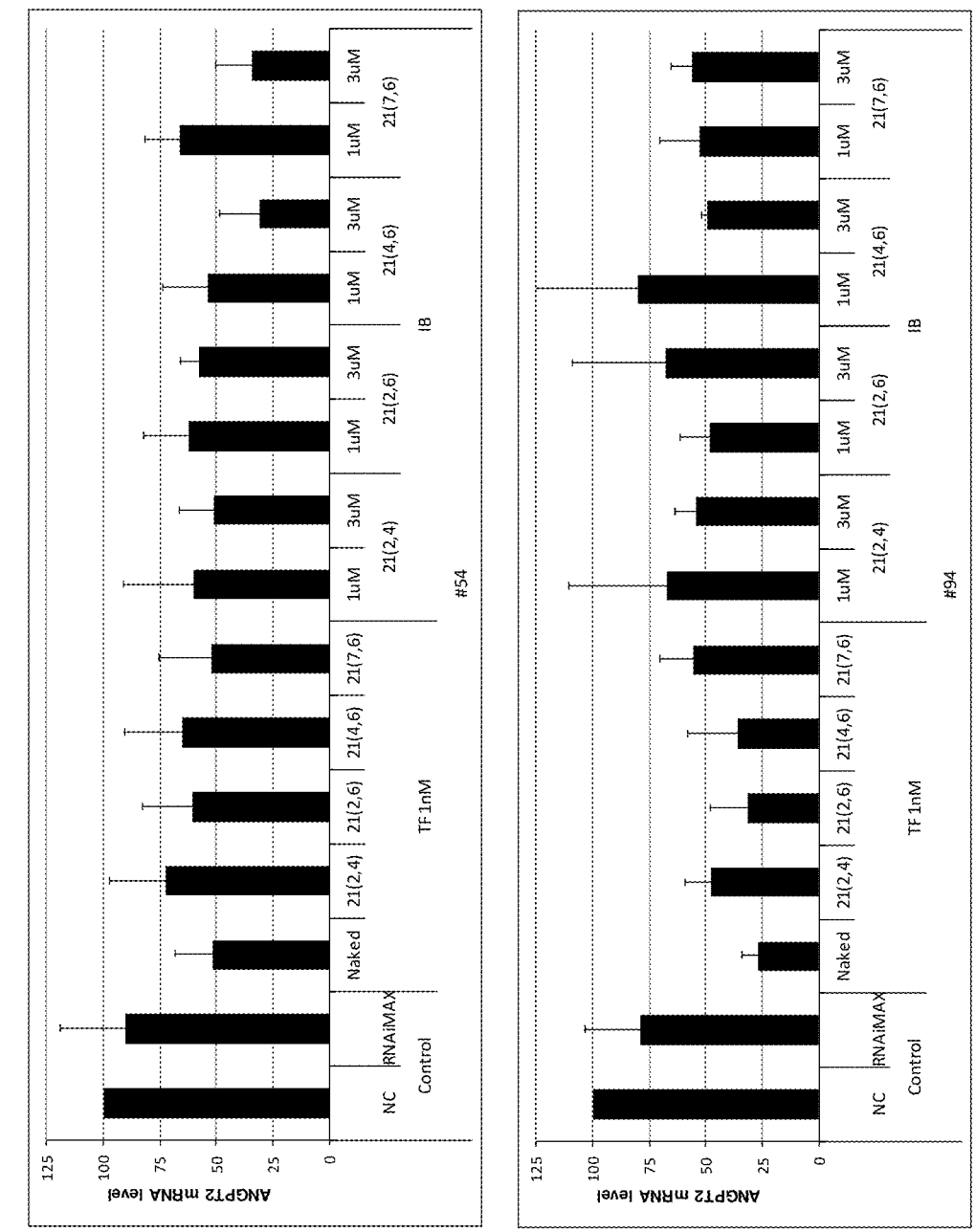
FIG. 6 shows the inhibition of ANGPT2 mRNA expression by exemplary cp-asiRNAs.

The results of the western blot assay are depicted in FIG. 4. As a result, asiANGPT2#54 and asiANGPT2#94 showed higher inhibitory efficiency than other asiANGPT2 strands. These strands were selected for the chemical modification.

Example 5: Chemical Modification of asiRNAs for Self-Delivery

Chemical modifications were applied to selected asiRNAs and cellular delivery of modified asiRNAs was tested in the absence of other delivery reagent. As described below, certain of the modifications improved endocytosis and stability of the asiRNAs. Such cell-penetrating asiRNAs (cp-asiRNAs) are able to be delivered into the cell in the absence of a delivery reagent.

Eight potential cp-asiRNAs (Table 2) were screened for ANGPT2 mRNA inhibition in SK-N-SH cells. SK-N-SH cells were incubated at with sp-asiRNAs at 1 uM and 3 uM without a delivery reagent and ANGPT2 mRNA levels were measured by real-time PCR.

TABLE 2

Modified asiRNA sequences tested for self-delivery and ANGPT2 inhibition.

| SEQ ID NO: | Sequence |
|---|---|
| 205 | cp-asiANGPT2#54-PS3/21(2,4)(S): 5' mCAmGAmCCmAGmUGmAAmAU*mA*A* cholesterol 3' |

TABLE 2-continued

Modified asiRNA sequences tested for
self-delivery and ANGPT2 inhibition.

| SEQ ID NO: | Sequence |
|---|---|
| 206 | cp-asiANGPT2#54-PS3/21(2,4)(AS):<br>5' UUAUUUCACUGGUCmUmGG*U*C*C*A 3' |
| 207 | cp-asiANGPT2#54-PS3/21(2,6)(S):<br>5' mCAmGAmCCmAGmUGmAAmAU*mA*A* cholesterol 3' |
| 208 | cp-asiANGPT2#54-PS3/21(2,6)(AS):<br>5' UUAUUUCACUGGUCmU*mG*G*U*C*C*A 3' |
| 209 | cp-asiANGPT2#54-PS3/21(4,6)(S):<br>5' mCAmGAmCCmAGmUGmAAmAU*mA*A* cholesterol 3' |
| 210 | cp-asiANGPT2#54-PS3/21(4,6)(AS):<br>5' UUAUUUCACUGGUCmU*mG*mG*mU*C*C*A 3' |
| 211 | cp-asiANGPT2#54-PS3/21(7,6)(S):<br>5' mCAmGAmCCmAGmUGmAAmAU*mA*A* cholesterol 3' |
| 212 | cp-asiANGPT2#54-PS3/21(7,6)(AS):<br>5' UUAUUUCACUGGUCmU*mG*mG*mU*mC*mC*mA 3' |
| 213 | cp-asiANGPT2#94-PS3/21(2,4)(S):<br>5' mUCmCGmACmCAmGCmAGmAU*mU*U* cholesterol 3' |
| 214 | cp-asiANGPT2#94-PS3/21(2,4)(AS):<br>5' AAAUCUGCUGGUCGmGmAU*C*A*U*C 3' |
| 215 | cp-asiANGPT2#94-PS3/21(2,6)(S):<br>5' mUCmCGmACmCAmGCmAGmAU*mU*U* cholesterol 3' |
| 216 | cp-asiANGPT2#94-PS3/21(2,6)(AS):<br>5' AAAUCUGCUGGUCGmG*mA*U*C*A*U*C 3' |
| 217 | cp-asiANGPT2#94-PS3/21(4,6)(S):<br>5' mUCmCGmACmCAmGCmAGmAU*mU*U* cholesterol 3' |
| 218 | cp-asiANGPT2#94-PS3/21(4,6)(AS):<br>5' AAAUCUGCUGGUCGmG*mA*mU*mC*A*U*C 3' |
| 219 | cp-asiANGPT2#94-PS3/21(7,6)(S):<br>5' mUCmCGmACmCAmGCmAGmAU*mU*U* cholesterol 3' |
| 220 | cp-asiANGPT2#94-PS3/21(7,6)(AS):<br>5' AAAUCUGCUGGUCGmG*mA*mU*mC*mA*mU*mC 3' | m = 2'-O-Methyl RNA,
* = phosphorothioate bond.

SK-N-SH cells (ATCC) that had been cultured in Minimum Essential medium (Gibco) containing 10% fetal bovine serum (Gibco) and 100 µg/ml penicillin/streptomycin in a 100 mm cell culture dish.

The potential cp-asiRNAs listed in Table 2 were incubated at 95° C. for 5 minutes and at 37° C. for 1 hour in OPTI-MEM buffer (Gibco). Proper strand annealing was confirmed via gel electrophoresis.

One day prior to treatment, $2.5 \times 10^4$ SK-N-SH cells were seeded in 24-well plates. Before treatment, SK-N-SH cells were washed with Minimum Essential medium then cultured in the presence of the potential cp-asiRNAs in OPTI-MEM buffer for 8 and 24 hours, at each point the asiRNA-containing OPTI-MEM media was replaced with a serum-containing media.

The level of ANGPT2 mRNA expression was determined using real-time PCR 48 hours after asiRNA treatment.

Example 6: Inhibition of ANGPT2 mRNA Expression Using ANGPT2-Targeting Cp-asiRNAs Inhibition of ANGPT2 mRNA by cp-asiRNAs was tested. Each potential cp-asiRNA was incubated with SK-N-SH cells at 1 uM and 3 uM without a delivery reagent and ANGPT2 mRNA levels were measured using real-time PCR.

SK-N-SH cells (ATCC) were cultured in Minimum Essential medium (Gibco) containing 10% fetal bovine serum (Gibco) and 100 µg/ml penicillin/streptomycin in a 100 mm cell culture dish.

The cp-asiRNAs were incubated at 95° C. for 5 minutes and at 37° C. for 1 hour in OPTI-MEM buffer (Gibco). Proper strand annealing was confirmed via gel electrophoresis.

One day prior to transfection, $2.5 \times 10^4$ SK-N-SH cells were seeded in 24-well plates. Immediately before treatment, the SK-N-SH cells were washed with Minimum Essential medium (Gibco) then cultured in the presence of the potential cp-asiRNAs in OPTI-MEM buffer for 24 hours, at which point the asiRNA-containing OPTI-MEM media was replaced with a serum-containing media.

The levels of ANGPT2 mRNA expression were determined 48 hours after asiRNA treatment by real-time PCR. Total RNA was extracted using RNAiso Plus (TaKaRa), and then 500 ng of the extracted RNA was used for cDNA synthesis using the High-capacity cDNA reverse transcription kit (Applied Biosystems), according to the manufacturer's instructions. Amplification of the ANGPT2 gene was detected using a power SYBR Premix Ex Taq (TaKaRa). GAPDH was amplified as an internal control.

Example 7: Inhibition of ANGPT2 Protein Expression Using ANGPT2-Targeting cp-asiRNAs Inhibition of ANGPT2 protein by cp-asiRNAs was tested. Each potential cp-asiRNA was incubated with SK-N-SH cells at 1 uM and 3 uM without a delivery reagent. SK-N-SH cells (ATCC) that had been cultured in Minimum Essential medium (Gibco) containing 10% fetal bovine serum (Gibco) and 100 µg/ml penicillin/streptomycin in a 100 mm cell culture dish.

The cp-asiRNAs were incubated at 95° C. for 5 minutes and at 37° C. for 1 hour in OPTI-MEM buffer (Gibco). Proper strand annealing was confirmed via gel electrophoresis.

One day prior to transfection, $2.5 \times 10^4$ SK-N-SH cells were seeded in 24-well plates. Immediately before treatment, the SK-N-SH cells were washed with Minimum Essential medium (Gibco) then cultured in the presence of cp-asiRNAs in OPTI-MEM buffer for 24 hours, at which point the asiRNA-containing OPTI-MEM media was replaced with a serum-containing media.

The levels of ANGPT2 protein expression were determined via western blot 48 hours after of asiRNA treatment. Briefly, the treated SK-N-SH cells were lysed with SDS lysis buffer (1% SDS, 100 mM Tris (pH 8.8)). 10 µg of the total protein extracts were loaded onto a 9% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 3% BSA (Bioworld) and then incubated overnight at 4°

C. in 3% BSA containing anti-ANGPT2 antibody (Santa Cruz) and anti-GAPDH (Santa Cruz). The membrane was then washed with 1×TBST for 10 minutes three times and was incubated for 1 hour at the room temperature in 1×TBST with HRP-conjugated secondary antibody. The membrane was washed with 1×TBST for 10 minutes and treated with 1×ECL for 1 minute. The ANGPT2 and GAPDH bands were then imaged using a Chemidoc instrument (Bio-rad).

Figure 7:
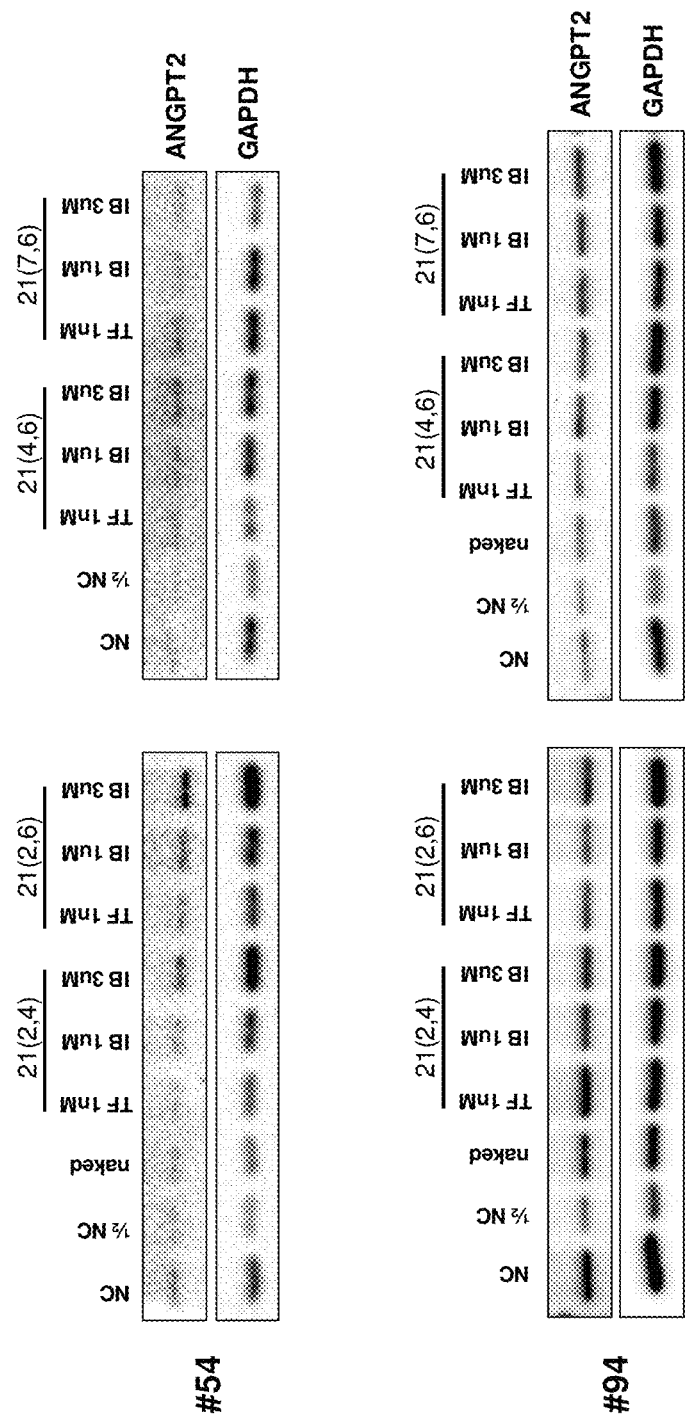
FIG. 7 shows the inhibition of ANGPT2 protein expression by exemplary cp-asiRNAs.

The results of the western blot assay are depicted in FIG. 7. As the result, cp-asiANGPT2#54 containing eight 2'-O-Methylation and 3 phosphorothioate bond on sense strand and two 2'-O-Methylation and 4 phosphorothioate bond on antisense strand, potential cp-asiANGPT2#94 containing eight 2'-O-Methylation and 3 phosphorothioate bond on sense strand and two 2'-O-Methylation and 6 phosphorothioate bond on antisense strand exhibited the highest levels of ANGPT2 inhibition.

Example 8: Inhibition of ANGPT2 mRNA Expression Using Additional ANGPT2-Targeting cp-asiRNAs A variety of potential cp-asiANGPT2 structures having different strand lengths and number of 2'-O-methylation modifications and phosphorothioate bond were synthesized and tested for their ability to inhibit ANGPT2 expression (Table 3).

TABLE 3

Additional cp-asiRNA sequences.

| SEQ ID NO: | Sequence |
|---|---|
| 221 | cp-asiANGPT2#54-PS3/19(2,4)(S):<br>5' mCAmGAmCCmAGmUGmAAmAU*mA*A*cholesterol 3' |
| 222 | cp-asiANGPT2#54-PS3/19(2,4)(AS):<br>5' UUAUUUCACUGGUCmU*mG*G*U*C 3' |
| 223 | cp-asiANGPT2#54-PS4/21(2,4)(S):<br>5' mCAmGAmCCmAGmUGmAAmA*U*mA*A*cholesterol 3' |
| 224 | cp-asiANGPT2#54-PS4/21(2,4)(AS):<br>5' UUAUUUCACUGGUCmUmGG*U*C*C*A 3' |
| 225 | cp-asiANGPT2#54-PS4/19(2,4)(S):<br>5' mCAmGAmCCmAGmUGmAAmA*U*mA*A*cholesterol 3' |
| 226 | cp-asiANGPT2#54-PS4/19(2,4)(AS):<br>5' UUAUUUCACUGGUCmU*mG*G*U*C 3' |
| 227 | cp-asiANGPT2#94-PS3/19(2,6)(S):<br>5' mUCmCGmACmCAmGCmAGmAU*mU*U*cholesterol 3' |
| 228 | cp-asiANGPT2#94-PS3/19(2,6)(AS):<br>5' AAAUCUGCUGGUCGmG*mA*U*C*A*U*C 3' | m = 2'-O-Methyl RNA,
* = phosphorothioate bond.

The ability of 1 uM and 3 uM of each cp-asiRNAs listed in Table 3 to inhibit ANGPT2 mRNA in SK-N-SH cells was tested.

SK-N-SH cells (ATCC) that had been cultured in Minimum Essential medium (Gibco) containing 10% fetal bovine serum (Gibco) and 100 μg/ml penicillin/streptomycin in a 100 mm cell culture dish. cp-asiRNAs listed in Table 3 were incubated at 95° C. for 5 minutes and at 37° C. for 1 hour in OPTI-MEM buffer (Gibco). Proper strand annealing was confirmed via gel electrophoresis.

One day prior to transfection, $2.5 \times 10^4$ SK-N-SH cells were seeded in 24-well plates. Before treatment, the SK-N-SH cells were washed with Minimum Essential medium (Gibco) then cultured in the presence of the potential cp-asiRNAs in OPTI-MEM buffer for 24 hours, at which point the asiRNA-containing OPTI-MEM media was replaced with a serum-containing media.

The levels of ANGPT2 mRNA expression were determined 48 hours after asiRNA treatment.

Figure 8:
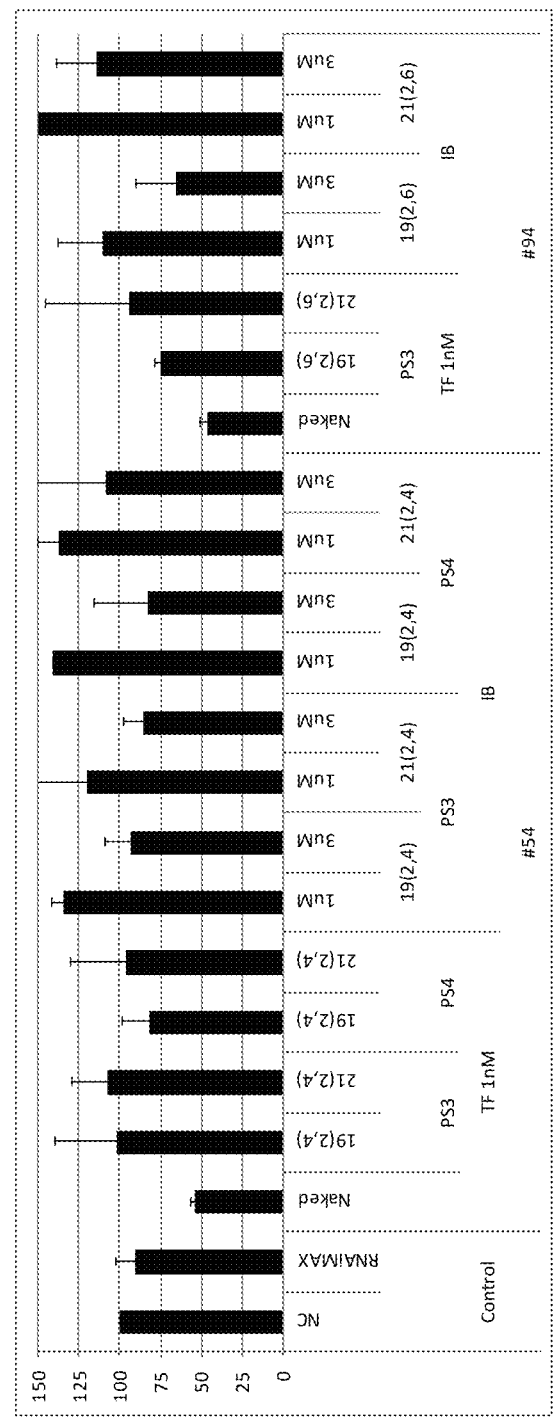
FIG. 8 shows the gene silencing efficiency of 6 cp-asiRNAs with different antisense strand lengths (19 or 21 nucleotides).

As shown in FIG. 8, cp-asiANGPT2#54 containing eight 2'-O-Methylation and 4phosphorothioate bond on sense strand and two 2'-O-Methylation and 4 phosphorothioate bond on antisense strand, potential cp-asiANGPT2#94 containing eight 2'-O-Methylation and 3 phosphorothioate bond on sense strand and two 2'-O-Methylation and 6 phosphorothioate bond on antisense strand exhibited higher efficiency in the ANGPT2 inhibition ability than other cp-asiANGPT2s.

Example 9: Inhibition of ANGPT2 Protein Using Additional ANGPT2-Targeting cp-asiRNAs cp-asiRNA was incubated with SK-N-SH cells at 1 uM and 3 uM without a delivery reagent and ANGPT2 protein levels were measured by western blot. SK-N-SH cells (ATCC) that had been cultured in Minimum Essential medium (Gibco) containing 10% fetal bovine serum (Gibco) and 100 μg/ml penicillin/streptomycin in a 100 mm cell culture dish.

The cp-asiRNAs were incubated at 95° C. for 5 minutes and at 37° C. for 1 hour in OPTI-MEM buffer (Gibco). Proper strand annealing was confirmed via gel electrophoresis.

One day prior to transfection, $2.5 \times 10^4$ SK-N-SH cells were seeded in 24-well plates. Immediately before treatment, the SK-N-SH cells were washed with Minimum Essential medium (Gibco) then cultured in the presence of the potential cp-asiRNAs in OPTI-MEM buffer for 24 hours, at which point the asiRNA-containing OPTI-MEM media was replaced with a serum-containing media.

The levels of ANGPT2 protein expression were determined via western blot 48 hours after asiRNA treatment. Treated SK-N-SH cells were lysed with SDS lysis buffer (1% SDS, 100 mM Tris (pH 8.8)). 10 μg of the total protein extracts were loaded onto a 9% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 3% BSA (Bioworld) and then incubated overnight at 4° C. in 3% BSA containing anti-ANGPT2 antibody (Santa Cruz) and anti-GAPDH antibody (Santa Cruz). The membrane was then washed with 1×TBST for 10 minutes three times and was incubated for 1 hour at the room temperature in 1×TBST with HRP-conjugated secondary antibody. The membrane was washed with 1×TBST for 10 minutes and treated with 1×ECL for 1 minute. The ANGPT2 and GAPDH bands were then imaged using a Chemidoc instrument (Bio-rad).

Figure 9:
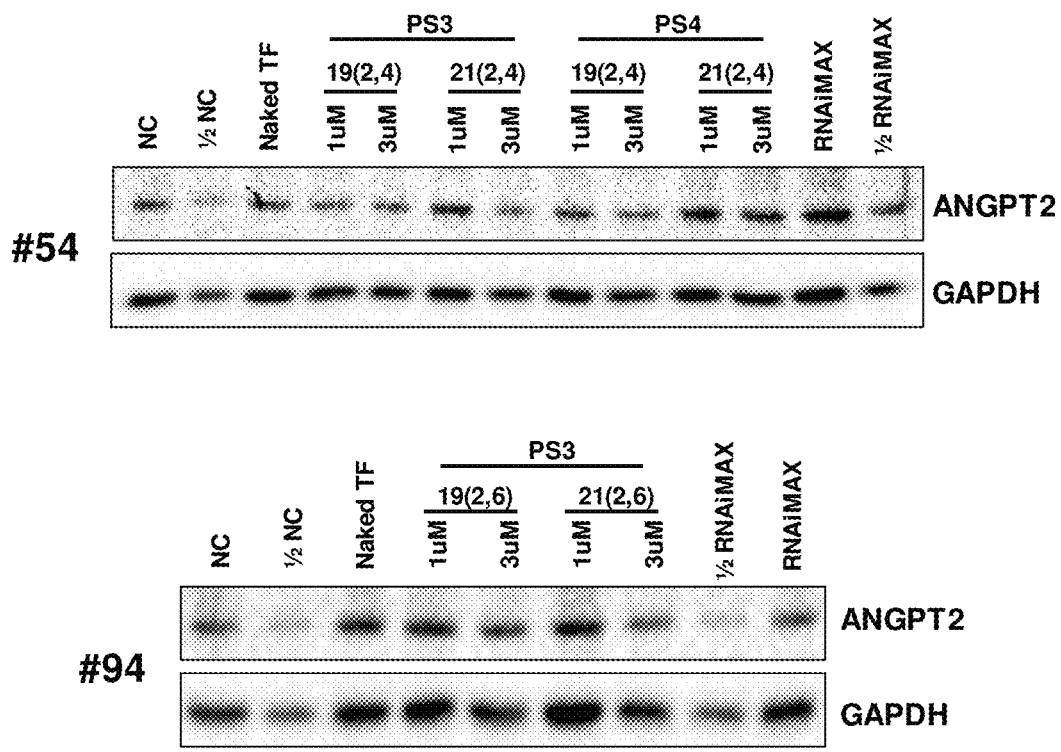
FIG. 9 shows the inhibition of ANGPT2 protein expression by 6 exemplary cp-asiRNAs.

The results of the western blot assay are depicted in FIG. 9. As a result, cp-asiANGPT2#54-PS4/19(2,4) exhibited the highest levels of ANGPT2 inhibition.

Example 10: Screening for PDGFB-Specific Asymmetric Shorter-Duplex Small Interfering RNAs To identify asymmetric shorter-duplex small interfering RNAs (asiRNAs) that inhibit PDGFB with high efficiency, 100 asiRNAs were synthesized and screened. The nucleic acid sequences of the screened asiRNAs are provided in Table 4.

TABLE 4

Nucleic acid sequences for exemplary PDGFB-targeting asiRNA.

| SEQ ID NO: | SEQUENCE (5' to 3') |
|---|---|
| 229 | asiPDGFB(1)S: GUUUGCACCUCUCCCU |
| 230 | asiPDGFB(1)AS: AGGGAGAGGUGCAAACUCCCG |
| 231 | asiPDGFB(2)S: UUUGCACCUCUCCCUG |
| 232 | asiPDGFB(2)AS: CAGGGAGAGGUGCAAACUCCC |
| 233 | asiPDGFB(3)S: UUGCACCUCUCCCUGC |
| 234 | asiPDGFB(3)AS: GCAGGGAGAGGUGCAAACUCC |
| 235 | asiPDGFB(4)S: AGCCAACUUUGGAAAA |
| 236 | asiPDGFB(4)AS: UUUUCCAAAGUUGGCUUUGCA |
| 237 | asiPDGFB(5)S: GCCAACUUUGGAAAAA |
| 238 | asiPDGFB(5)AS: UUUUUCCAAAGUUGGCUUUGC |
| 239 | asiPDGFB(6)S: CCAACUUUGGAAAAAG |
| 240 | asiPDGFB(6)AS: CUUUUUCCAAAGUUGGCUUUG |
| 241 | asiPDGFB(7)S: CAACUUUGGAAAAAGU |
| 242 | asiPDGFB(7)AS: ACUUUUUCCAAAGUUGGCUUU |
| 243 | asiPDGFB(8)S: AACUUUGGAAAAAGUU |
| 244 | asiPDGFB(8)AS: AACUUUUUCCAAAGUUGGCUU |
| 245 | asiPDGFB(9)S: ACUUUGGAAAAAGUUU |
| 246 | asiPDGFB(9)AS: AAACUUUUUCCAAAGUUGGCU |
| 247 | asiPDGFB(10)S: CUUUGGAAAAAGUUUU |
| 248 | asiPDGFB(10)AS: AAAACUUUUUCCAAAGUUGGC |
| 249 | asiPDGFB(11)S: AAAUGUUGCAAAAAAG |
| 250 | asiPDGFB(11)AS: CUUUUUUGCAACAUUUUCUGG |
| 251 | asiPDGFB(12)S: AAUGUUGCAAAAAAGC |
| 252 | asiPDGFB(12)AS: GCUUUUUUGCAACAUUUUCUG |
| 253 | asiPDGFB(13)S: UGCAAAAAAGCUAAGC |
| 254 | asiPDGFB(13)AS: GCUUAGCUUUUUUGCAACAUU |
| 255 | asiPDGFB(14)S: GCAAAAAAGCUAAGCC |
| 256 | asiPDGFB(14)AS: GGCUUAGCUUUUUUGCAACAU |
| 257 | asiPDGFB(15)S: GUGAAGACGAACCAUC |
| 258 | asiPDGFB(15)AS: GAUGGUUCGUCUUCACUCGCC |
| 259 | asiPDGFB(16)S: UGAAGACGAACCAUCG |
| 260 | asiPDGFB(16)AS: CGAUGGUUCGUCUUCACUCGC |
| 261 | asiPDGFB(17)S: GUGUUCCUUUUCCUCU |
| 262 | asiPDGFB(17)AS: AGAGGAAAAGGAACACGGCAG |
| 263 | asiPDGFB(18)S: GUCGGCAUGAAUCGCU |

TABLE 4-continued

Nucleic acid sequences for exemplary PDGFB-targeting asiRNA.

| SEQ ID NO: | SEQUENCE (5' to 3') |
|---|---|
| 264 | asiPDGFB(18)AS: AGCGAUUCAUGCCGACUCCGG |
| 265 | asiPDGFB(19)S: UCGGCAUGAAUCGCUG |
| 266 | asiPDGFB(19)AS: CAGCGAUUCAUGCCGACUCCG |
| 267 | asiPDGFB(20)S: GGCAUGAAUCGCUGCU |
| 268 | asiPDGFB(20)AS: AGCAGCGAUUCAUGCCGACUC |
| 269 | asiPDGFB(21)S: GCAUGAAUCGCUGCUG |
| 270 | asiPDGFB(21)AS: CAGCAGCGAUUCAUGCCGACU |
| 271 | asiPDGFB(22)S: CAUGAAUCGCUGCUGG |
| 272 | asiPDGFB(22)AS: CCAGCAGCGAUUCAUGCCGAC |
| 273 | asiPDGFB(23)S: CGCUGCUGGGCGCUCU |
| 274 | asiPDGFB(23)AS: AGAGCGCCCAGCAGCGAUUCA |
| 275 | asiPDGFB(24)S: GCUGCUGGGCGCUCUU |
| 276 | asiPDGFB(24)AS: AAGAGCGCCCAGCAGCGAUUC |
| 277 | asiPDGFB(25)S: CUGCUGGGCGCUCUUC |
| 278 | asiPDGFB(25)AS: GAAGAGCGCCCAGCAGCGAUU |
| 279 | asiPDGFB(26)S: GCUGCUACCUGCGUCU |
| 280 | asiPDGFB(26)AS: AGACGCAGGUAGCAGCAGAGA |
| 281 | asiPDGFB(27)S: CUGCUACCUGCGUCUG |
| 282 | asiPDGFB(27)AS: CAGACGCAGGUAGCAGCAGAG |
| 283 | asiPDGFB(28)S: UGCUACCUGCGUCUGG |
| 284 | asiPDGFB(28)AS: CCAGACGCAGGUAGCAGCAGA |
| 285 | asiPDGFB(29)S: GCUACCUGCGUCUGGU |
| 286 | asiPDGFB(29)AS: ACCAGACGCAGGUAGCAGCAG |
| 287 | asiPDGFB(30)S: CUACCUGCGUCUGGUC |
| 288 | asiPDGFB(30)AS: GACCAGACGCAGGUAGCAGCA |
| 289 | asiPDGFB(31)S: UACCUGCGUCUGGUCA |
| 290 | asiPDGFB(31)AS: UGACCAGACGCAGGUAGCAGC |
| 291 | asiPDGFB(32)S: ACCUGCGUCUGGUCAG |
| 292 | asiPDGFB(32)AS: CUGACCAGACGCAGGUAGCAG |
| 293 | asiPDGFB(33)S: CAACGCCAACUUCCUG |
| 294 | asiPDGFB(33)AS: CAGGAAGUUGGCGUUGGUGCG |
| 295 | asiPDGFB(34)S: AACGCCAACUUCCUGG |
| 296 | asiPDGFB(34)AS: CCAGGAAGUUGGCGUUGGUGC |
| 297 | asiPDGFB(35)S: ACGCCAACUUCCUGGU |
| 298 | asiPDGFB(35)AS: ACCAGGAAGUUGGCGUUGGUG |
| 299 | asiPDGFB(36)S: CGCCAACUUCCUGGUG |
| 300 | asiPDGFB(36)AS: CACCAGGAAGUUGGCGUUGGU |

TABLE 4-continued

Nucleic acid sequences for exemplary PDGFB-targeting asiRNA.

| SEQ ID NO: | SEQUENCE (5' to 3') |
|---|---|
| 301 | asiPDGFB(37)S: GCCAACUUCCUGGUGU |
| 302 | asiPDGFB(37)AS: ACACCAGGAAGUUGGCGUUGG |
| 303 | asiPDGFB(38)S: CCAACUUCCUGGUGUG |
| 304 | asiPDGFB(38)AS: CACACCAGGAAGUUGGCGUUG |
| 305 | asiPDGFB(39)S: CAACUUCCUGGUGUGG |
| 306 | asiPDGFB(39)AS: CCACACCAGGAAGUUGGCGUU |
| 307 | asiPDGFB(40)S: UGACCAUUCGGACGGU |
| 308 | asiPDGFB(40)AS: ACCGUCCGAAUGGUCACCCGA |
| 309 | asiPDGFB(41)S: GGCAGGGUUAUUUAAU |
| 310 | asiPDGFB(41)AS: AUUAAAUAACCCUGCCCACAC |
| 311 | asiPDGFB(42)S: GCAGGGUUAUUUAAUA |
| 312 | asiPDGFB(42)AS: UAUUAAAUAACCCUGCCCACA |
| 313 | asiPDGFB(43)S: CAGGGUUAUUUAAUAU |
| 314 | asiPDGFB(43)AS: AUAUUAAAUAACCCUGCCCAC |
| 315 | asiPDGFB(44)S: AGGGUUAUUUAAUAUG |
| 316 | asiPDGFB(44)AS: CAUAUUAAAUAACCCUGCCCA |
| 317 | asiPDGFB(45)S: GGGUUAUUUAAUAUGG |
| 318 | asiPDGFB(45)AS: CCAUAUUAAAUAACCCUGCCC |
| 319 | asiPDGFB(46)S: GGUUAUUUAAUAUGGU |
| 320 | asiPDGFB(46)AS: ACCAUAUUAAAUAACCCUGCC |
| 321 | asiPDGFB(47)S: GUUAUUUAAUAUGGUA |
| 322 | asiPDGFB(47)AS: UACCAUAUUAAAUAACCCUGC |
| 323 | asiPDGFB(48)S: GUAUUUGCUGUAUUGC |
| 324 | asiPDGFB(48)AS: GCAAUACAGCAAAUACCAUAU |
| 325 | asiPDGFB(49)S: UAUUUGCUGUAUUGCC |
| 326 | asiPDGFB(49)AS: GGCAAUACAGCAAAUACCAUA |
| 327 | asiPDGFB(50)S: AUUUGCUGUAUUGCCC |
| 328 | asiPDGFB(50)AS: GGGCAAUACAGCAAAUACCAU |
| 329 | asiPDGFB(51)S: UUUGCUGUAUUGCCCC |
| 330 | asiPDGFB(51)AS: GGGGCAAUACAGCAAAUACCA |
| 331 | asiPDGFB(52)S: UGCUGUAUUGCCCCCA |
| 332 | asiPDGFB(52)AS: UGGGGGCAAUACAGCAAAUAC |
| 333 | asiPDGFB(53)S: GCUGUAUUGCCCCCAU |
| 334 | asiPDGFB(53)AS: AUGGGGGCAAUACAGCAAAUA |
| 335 | asiPDGFB(54)S: CUGUAUUGCCCCCAUG |
| 336 | asiPDGFB(54)AS: CAUGGGGGCAAUACAGCAAAU |
| 337 | asiPDGFB(55)S: UGUAUUGCCCCCAUGG |
| 338 | asiPDGFB(55)AS: CCAUGGGGGCAAUACAGCAAA |
| 339 | asiPDGFB(56)S: GUAUUGCCCCCAUGGG |
| 340 | asiPDGFB(56)AS: CCCAUGGGGGCAAUACAGCAA |
| 341 | asiPDGFB(57)S: AUUGCCCCCAUGGGGU |
| 342 | asiPDGFB(57)AS: ACCCCAUGGGGGCAAUACAGC |
| 343 | asiPDGFB(58)S: UUGCCCCCAUGGGGUC |
| 344 | asiPDGFB(58)AS: GACCCCAUGGGGGCAAUACAG |
| 345 | asiPDGFB(59)S: UGCCCCCAUGGGGUCC |
| 346 | asiPDGFB(59)AS: GGACCCCAUGGGGGCAAUACA |
| 347 | asiPDGFB(60)S: GCCCCCAUGGGGUCCU |
| 348 | asiPDGFB(60)AS: AGGACCCCAUGGGGGCAAUAC |
| 349 | asiPDGFB(61)S: CCCCCAUGGGGUCCUU |
| 350 | asiPDGFB(61)AS: AAGGACCCCAUGGGGGCAAUA |
| 351 | asiPDGFB(62)S: CCCCAUGGGGUCCUUG |
| 352 | asiPDGFB(62)AS: CAAGGACCCCAUGGGGGCAAU |
| 353 | asiPDGFB(63)S: GGGGUCCUUGGAGUGA |
| 354 | asiPDGFB(63)AS: UCACUCCAAGGACCCCAUGGG |
| 355 | asiPDGFB(64)S: GGGUCCUUGGAGUGAU |
| 356 | asiPDGFB(64)AS: AUCACUCCAAGGACCCCAUGG |
| 357 | asiPDGFB(65)S: GGUCCUUGGAGUGAUA |
| 358 | asiPDGFB(65)AS: UAUCACUCCAAGGACCCCAUG |
| 359 | asiPDGFB(66)S: GUCCUUGGAGUGAUAA |
| 360 | asiPDGFB(66)AS: UUAUCACUCCAAGGACCCCAU |
| 361 | asiPDGFB(67)S: UCCUUGGAGUGAUAAU |
| 362 | asiPDGFB(67)AS: AUUAUCACUCCAAGGACCCCA |
| 363 | asiPDGFB(68)S: GUCCGUCUGUCUCGAU |
| 364 | asiPDGFB(68)AS: AUCGAGACAGACGGACGAGGG |
| 365 | asiPDGFB(69)S: UCCGUCUGUCUCGAUG |
| 366 | asiPDGFB(69)AS: CAUCGAGACAGACGGACGAGG |
| 367 | asiPDGFB(70)S: CCGUCUGUCUCGAUGC |
| 368 | asiPDGFB(70)AS: GCAUCGAGACAGACGGACGAG |
| 369 | asiPDGFB(71)S: GUCUGUCUCGAUGCCU |
| 370 | asiPDGFB(71)AS: AGGCAUCGAGACAGACGGACG |
| 371 | asiPDGFB(72)S: UCUGUCUCGAUGCCUG |
| 372 | asiPDGFB(72)AS: CAGGCAUCGAGACAGACGGAC |
| 373 | asiPDGFB(73)S: CUGUCUCGAUGCCUGA |
| 374 | asiPDGFB(73)AS: UCAGGCAUCGAGACAGACGGA |

TABLE 4-continued

Nucleic acid sequences for exemplary PDGFB-targeting asiRNA.

| SEQ ID NO: | SEQUENCE (5' to 3') |
|---|---|
| 375 | asiPDGFB(74)S: UGUCUCGAUGCCUGAU |
| 376 | asiPDGFB(74)AS: AUCAGGCAUCGAGACAGACGG |
| 377 | asiPDGFB(75)S: GUCUCGAUGCCUGAUU |
| 378 | asiPDGFB(75)AS: AAUCAGGCAUCGAGACAGACG |
| 379 | asiPDGFB(76)S: UCUCGAUGCCUGAUUC |
| 380 | asiPDGFB(76)AS: GAAUCAGGCAUCGAGACAGAC |
| 381 | asiPDGFB(77)S: CUCGAUGCCUGAUUCG |
| 382 | asiPDGFB(77)AS: CGAAUCAGGCAUCGAGACAGA |
| 383 | asiPDGFB(78)S: UCGAUGCCUGAUUCGG |
| 384 | asiPDGFB(78)AS: CCGAAUCAGGCAUCGAGACAG |
| 385 | asiPDGFB(79)S: CGAUGCCUGAUUCGGA |
| 386 | asiPDGFB(79)AS: UCCGAAUCAGGCAUCGAGACA |
| 387 | asiPDGFB(80)S: GAUGCCUGAUUCGGAC |
| 388 | asiPDGFB(80)AS: GUCCGAAUCAGGCAUCGAGAC |
| 389 | asiPDGFB(81)S: AUGCCUGAUUCGGACG |
| 390 | asiPDGFB(81)AS: CGUCCGAAUCAGGCAUCGAGA |
| 391 | asiPDGFB(82)S: CUGAUUCGGACGGCCA |
| 392 | asiPDGFB(82)AS: UGGCCGUCCGAAUCAGGCAUC |
| 393 | asiPDGFB(83)S: UGAUUCGGACGGCCAA |
| 394 | asiPDGFB(83)AS: UUGGCCGUCCGAAUCAGGCAU |
| 395 | asiPDGFB(84)S: GAUUCGGACGGCCAAU |
| 396 | asiPDGFB(84)AS: AUUGGCCGUCCGAAUCAGGCA |
| 397 | asiPDGFB(85)S: AUUCGGACGGCCAAUG |
| 398 | asiPDGFB(85)AS: CAUUGGCCGUCCGAAUCAGGC |
| 399 | asiPDGFB(86)S: UUCGGACGGCCAAUGG |
| 400 | asiPDGFB(86)AS: CCAUUGGCCGUCCGAAUCAGG |
| 401 | asiPDGFB(87)S: UCGGACGGCCAAUGGU |
| 402 | asiPDGFB(87)AS: ACCAUUGGCCGUCCGAAUCAG |
| 403 | asiPDGFB(88)S: CGGACGGCCAAUGGUG |
| 404 | asiPDGFB(88)AS: CACCAUUGGCCGUCCGAAUCA |
| 405 | asiPDGFB(89)S: GGACGGCCAAUGGUGC |
| 406 | asiPDGFB(89)AS: GCACCAUUGGCCGUCCGAAUC |
| 407 | asiPDGFB(90)S: GACGGCCAAUGGUGCU |
| 408 | asiPDGFB(90)AS: AGCACCAUUGGCCGUCCGAAU |
| 409 | asiPDGFB(91)S: ACGGCCAAUGGUGCUU |
| 410 | asiPDGFB(91)AS: AAGCACCAUUGGCCGUCCGAA |
| 411 | asiPDGFB(92)S: CGGCCAAUGGUGCUUC |
| 412 | asiPDGFB(92)AS: GAAGCACCAUUGGCCGUCCGA |
| 413 | asiPDGFB(93)S: UCCUUCAGUUUGUAAA |
| 414 | asiPDGFB(93)AS: UUUACAAACUGAAGGAAGCAG |
| 415 | asiPDGFB(94)S: CCUUCAGUUUGUAAAG |
| 416 | asiPDGFB(94)AS: CUUUACAAACUGAAGGAAGCA |
| 417 | asiPDGFB(95)S: CUUCAGUUUGUAAAGU |
| 418 | asiPDGFB(95)AS: ACUUUACAAACUGAAGGAAGC |
| 419 | asiPDGFB(96)S: UUAUAUUUUUGGGGGC |
| 420 | asiPDGFB(96)AS: GCCCCCAAAAAUAUAAUCACC |
| 421 | asiPDGFB(97)S: UAUAUUUUUGGGGGCU |
| 422 | asiPDGFB(97)AS: AGCCCCCAAAAAUAUAAUCAC |
| 423 | asiPDGFB(98)S: AUAUUUUUGGGGGCUU |
| 424 | asiPDGFB(98)AS: AAGCCCCCAAAAAUAUAAUCA |
| 425 | asiPDGFB(99)S: UAUUUUUGGGGGCUUU |
| 426 | asiPDGFB(99)AS: AAAGCCCCCAAAAAUAUAAUC |
| 427 | asiPDGFB(100)S: AUUUUUGGGGGCUUUC |
| 428 | asiPDGFB(100)AS: GAAAGCCCCCAAAAAUAUAAU |

The asiRNAs listed in Table 4 were incubated at 95° C. for 2 minutes and at 37° C. for 1 hour in 1× siRNA duplex buffer (STpharm). Proper strand annealing was confirmed via gel electrophoresis. For the screen, A549 cells (ATCC) were used that had been cultured in Dulbecco's modified Eagle's medium (Gibco) containing 10% fetal bovine serum (Gibco) and 100 μg/ml penicillin/streptomycin in a 100 mm cell culture dish. One day prior to transfection, $5 \times 10^3$ A549 cells were seeded in 96-well plates. The A549 cells were transfected with 0.1 nM of the asiRNAs using RNAiMAX (Invitrogen) according to the manufacturer's instructions.

The PDGFB mRNA levels in the transfected cells were measured 24 hours after transfection using qRT-PCR. Specifically, total RNA was extracted using TOYOBO lysis reagent and then ⅕ volume of the reaction mixture was used for cDNA synthesis using the TOYOBO RT reagent (TOYOBO SuperPrep). The synthesized cDNA was diluted and then quantitative RT-PCR was performed using THUNDERBIRD® Probe qPCR Mix (TOYOBO). Amplification of the target gene was detected using PDGFB TaqMan® Probe (Hs00966522_m1) and 18 S TaqMan® Probe (Hs03928985_g1).

Figure 11:
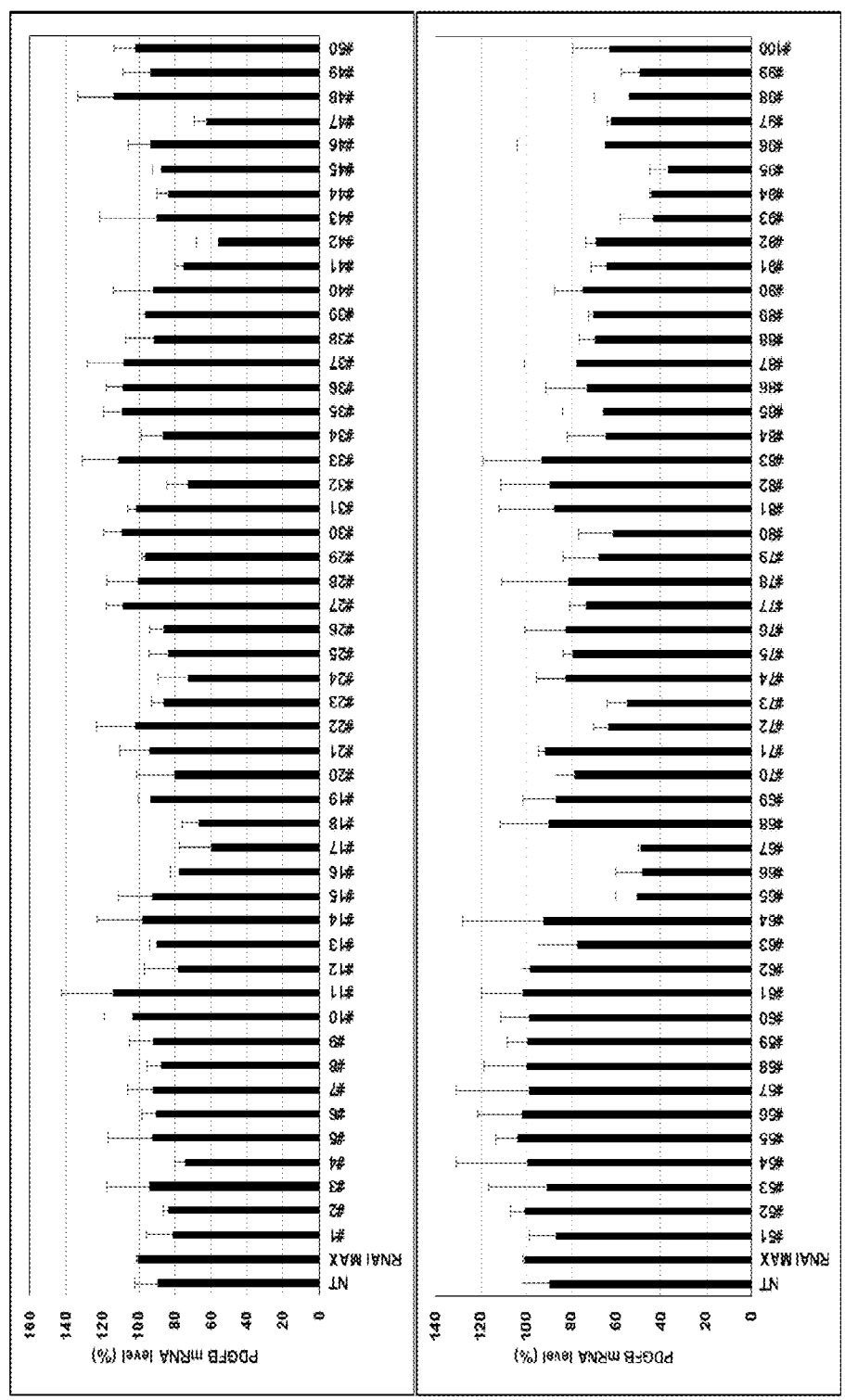
FIG. 11 shows the gene silencing efficiency of 100 exemplary asiRNAs that target PDGFB.

The expression level of PDGFB inhibition by each of the 100 asiRNAs is provided in FIG. 11. Twenty-two of the asiRNA sequences targeting PDGFB mRNA, asiRNA (17), asiRNA (24), asiRNA (42), asiRNA (43), asiRNA (47), asiRNA (53), asiRNA (63), asiRNA (64), asiRNA (65), asiRNA (66), asiRNA (67), asiRNA (72), asiRNA (73), asiRNA (79), asiRNA (80), asiRNA (84), asiRNA (85), asiRNA (92), asiRNA (93), asiRNA (94), asiRNA (95), asiRNA (99) were selected for use in follow-up studies.

Example 11: Inhibition of PDGFB mRNA Expression Using PDGFB-Targeting asiRNAs Twenty-two of the asiRNA sequences targeting PDGFB mRNA, asiRNA (17), asiRNA (24), asiRNA (42), asiRNA (43), asiRNA (47), asiRNA (53), asiRNA (63), asiRNA (64), asiRNA (65), asiRNA (66), asiRNA (67), asiRNA (72), asiRNA (73), asiRNA (79), asiRNA (80), asiRNA (84), asiRNA (85), asiRNA (92), asiRNA (93), asiRNA (94), asiRNA (95), asiRNA (99) were tested for their ability to inhibit PDGFB expression at different concentrations. The asiRNAs were incubated at 95° C. for 2 minutes and at 37° C. for 1 hour in 1× siRNA duplex buffer (STpharm). Proper strand annealing was confirmed via gel electrophoresis. For the screen, A549 cells (ATCC) were used that had been cultured in Dulbecco's modified Eagle's medium (Gibco) containing 10% fetal bovine serum (Gibco) and 100 µg/ml penicillin/streptomycin in a 100 mm cell culture dish. One day prior to transfection, $2.5 \times 10^4$ A549 cells were seeded in 24-well plates. The A549 cells were transfected with asiRNAs using RNAiMAX (Invitrogen) according to the manufacturer's instructions.

The PDGFB mRNA levels in the transfected cells were measured 24 hours after transfection using real-time PCR. Specifically, total RNA was extracted using RNAiso Plus (TaKaRa), and then 500 ng of the extracted RNA was used for cDNA synthesis using the High-capacity cDNA reverse transcription kit (Applied Biosystems), according to the manufacturer's instructions. The synthesized cDNA was diluted and then quantitative real-time PCR was performed using the StepOne real-time PCR system (Applied Biosystems) according to manufacturer's instructions. Amplification of the PDGFB gene was detected using a power SYBR Premix Ex Taq (TaKaRa). GAPDH was amplified as an internal control. The following primer sequences were used:

```
Human GAPDH-forward
                                 (SEQ ID NO: 201)
5'-GAG TCA ACG GAT TTG GTC GT-3'

Human GAPDH-reverse
                                 (SEQ ID NO: 202)
5'-GAC AAG CTT CCC GTT CTC AG-3'

Human PDGFB-forward
                                 (SEQ ID NO: 429)
5'-CAA GGG ACC TGC TCA TCA TAT T-3'

Human PDGFB-reverse
                                 (SEQ ID NO: 430)
5'-TAC CAC AGT CTC CCT CCT ATT T-3'
```

Figure 12:
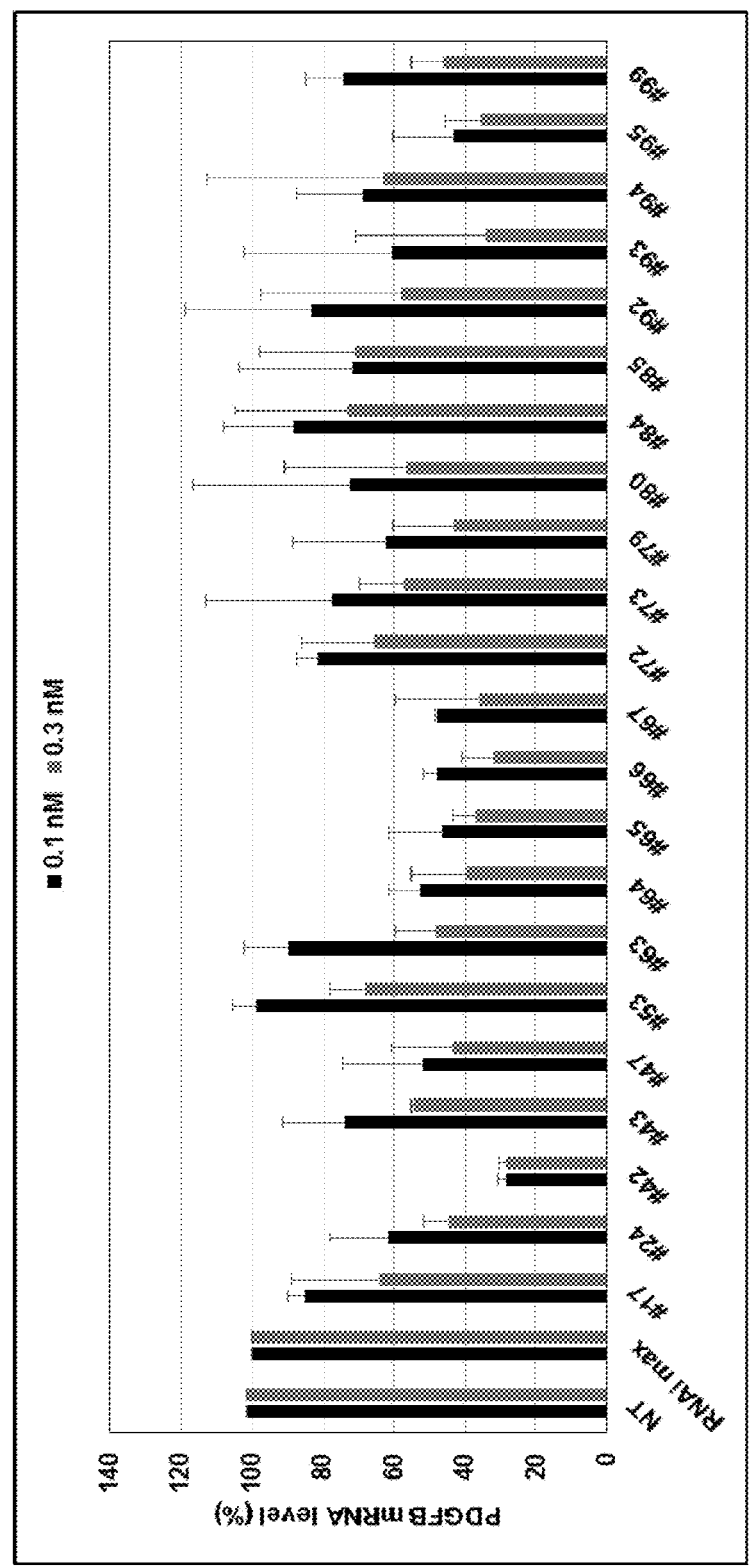
FIG. 12 shows the gene silencing efficiency of 22 exemplary asiRNAs that target PDGFB.

The level of PDGFB inhibition by the different concentrations of the 22 asiRNAs is provided in FIG. 12. 12 of the asiRNA sequences targeting PDGFB mRNA, asiRNA (24), asiRNA (42), asiRNA (47), asiRNA (64), asiRNA (65), asiRNA (66), asiRNA (67), asiRNA (73), asiRNA (80), asiRNA (94), asiRNA (95), asiRNA (99) were selected for use in follow-up studies.

Example 12: Inhibition of PDGFB Protein Expression Using PDGFB-Specific asiRNAs Twelve of the asiRNAs were incubated at 95° C. for 2 minutes and at 37° C. for 1 hour in 1× siRNA duplex buffer (STpharm). Proper strand annealing was confirmed via gel electrophoresis. A549 cells (ATCC) were used that had been cultured in Dulbecco's modified Eagle's medium (Gibco) containing 10% fetal bovine serum (Gibco) and 100 µg/ml penicillin/streptomycin in a 100 mm cell culture dish. One day prior to transfection, $9.0 \times 10^4$ A549 cells were seeded in 6-well plates. A549 cells were transfected with 0.3 nM of the asiRNAs using RNAiMAX (Invitrogen) according to the manufacturer's instructions.

The PDGFB mRNA levels in the transfected cells were measured 48 hours after transfection using real-time PCR and the level of PDGFB protein expression was determined via western blot.

Specifically, total RNA was extracted using RNAiso Plus (TaKaRa), and then 500 ng of the extracted RNA was used for cDNA synthesis using the High-capacity cDNA reverse transcription kit (Applied Biosystems), according to the manufacturer's instructions. The synthesized cDNA was diluted and then quantitative real-time PCR was performed using the StepOne real-time PCR system (Applied Biosystems) according to manufacturer's instructions. Amplification of the PDGFB gene was detected using a power SYBR Premix Ex Taq (TaKaRa). GAPDH was amplified as an internal control. The following primer sequences were used:

```
Human GAPDH-forward
                                 (SEQ ID NO: 201)
5'-GAG TCA ACG GAT TTG GTC GT-3'

Human GAPDH-reverse
                                 (SEQ ID NO: 202)
5'-GAC AAG CTT CCC GTT CTC AG-3'

Human PDGFB-forward
                                 (SEQ ID NO: 429)
5'-CAA GGG ACC TGC TCA TCA TAT T-3'

Human PDGFB-reverse
                                 (SEQ ID NO: 430)
5'-TAC CAC AGT CTC CCT CCT ATT T-3'
```

Figure 13:
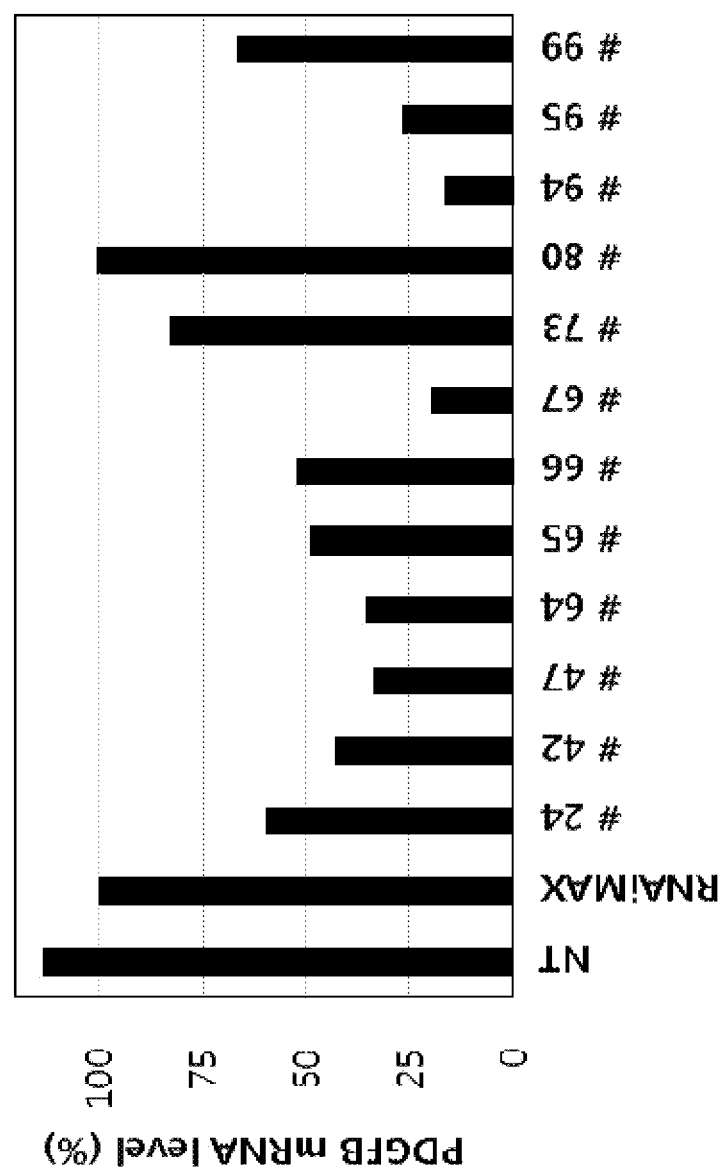
FIG. 13 shows the gene silencing effects of 12 exemplary asiRNAs that target PDGFB.

The mRNA level results are depicted in FIG. 13. 6 of the asiRNA sequences targeting PDGFB mRNA, asiRNA (42), asiRNA (47), asiRNA (64), asiRNA (67), asiRNA (94), asiRNA (95) shows effective gene silencing activities (60%~).

In case of protein level, the transfected A549 cells were lysed with RIPA buffer (GE). 20 µg of the total protein extract of A549 cells were loaded onto a 10% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-PDGFB antibody (Abcam) and anti-β-actin antibody (Santa Cruz). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL for 1 minute. The PDGFB and β-actin bands were then imaged using a Chemidoc instrument (Bio-rad).

The results of the western blot assay are depicted in FIG. 14. In asiPDGFB(42, 47, 66, 67, 94, 95) transfection cell lines of A549 cells, 50% or more of PDGFB protein inhibition were confirmed (FIG. 14).

Taken together, 5 of the asiRNA sequences targeting PDGFB gene, asiRNA (42), asiRNA (47), asiRNA (67), asiRNA (94), asiRNA (95), were selected for use in follow-up studies.

Example 13: S Chemical Modification of asiRNAs for Self-Delivery

Chemical modifications were applied to the asiRNAs selected in Example 3 and the cellular delivery of the modified asiRNAs was tested in the absence of other delivery vehicle. As described below, certain of the modifications improved endocytosis and stability of asiRNAs. Such cell penetrating asiRNAs (cp-asiRNAs) are able to be delivered into the cell in the absence of a delivery vehicle. The expression of PDGFB mRNA by the cells is provided in FIG. 15 and the PDGFB protein levels are provided in FIG. 16, as determined using methods described above.

Potential cp-asiRNAs (Table 5) were screened for Platelet-derived growth factor subunit B (PDGFB) mRNA inhibition in A549 cells. Each potential cp-asiRNA was incubated with A549 cells at 1 μM and 3 μM without a delivery vehicle and PDGFB expression levels were measured by qRT-PCR and western blot study.

TABLE 5

Modified asiRNA sequences tested for self-delivery and PDGFB inhibition (5' to 3').

| SEQ ID NO: | Sequence |
|---|---|
| 431 | asiPDGFB(42)-S:<br>mGCmAGmGGmUUmAUmUUmAA*mU*A*cholesterol |
| 432 | asiPDGFB(42)-(7,4)AS:<br>UAUUAAAUAACCCUmGmCmC*mC*mA*mC*mA |
| 433 | asiPDGFB(42)-(4,4)AS:<br>UAUUAAAUAACCCUmGmCmC*mC*A*C*A |
| 434 | asiPDGFB(42)-(2,4)AS:<br>UAUUAAAUAACCCUmGmCC*C*A*C*A |
| 435 | asiPDGFB(47)-S:<br>mGUmUAmUUmUAmAUmAUmGG*mU*A*cholesterol |
| 436 | asiPDGFB(47)-(7,4)AS:<br>UACCAUAUUAAAUAmAmCmC*mC*mU*mG*mC |
| 437 | asiPDGFB(47)-(4,4)AS:<br>UACCAUAUUAAAUAmAmCmC*mC*U*G*C |
| 438 | asiPDGFB(47)-(2,4)AS:<br>UACCAUAUUAAAUAmAmCC*C*U*G*C |
| 439 | asiPDGFB(67)-S:<br>mUCmCUmUGmGAmGUmGAmUA*mA*U*cholesterol |
| 440 | asiPDGFB(67)-(7,4)AS:<br>AUUAUCACUCCAAGmGmAmC*mC*mC*mC*mA |
| 441 | asiPDGFB(67)-(4,4)AS:<br>AUUAUCACUCCAAGmGmAmC*mC*C*C*A |
| 442 | asiPDGFB(67)-(2,4)AS:<br>AUUAUCACUCCAAGmGmAC*C*C*C*A | m = 2'-O-Methyl RNA.
* = phosphorothioate bond.

A549 cells (ATCC) were cultured in Dulbecco's modified Eagle's medium (DMEM, Gibco) containing 10% fetal bovine serum (FBS, Gibco) and 100 units/ml Penicillin 100 μg/ml Streptomycin in a 100 mm cell culture dish. The potential cp-asiRNAs listed in Table 5 were incubated at 95° C. for 2 minutes and at 37° C. for 1 hour in Opti-MEM (Gibco). Proper strand annealing of the potential cp-asiRNAs was confirmed by gel electrophoresis.

On that day cp-asiRNAs treatment, 9×10⁴ cells were seeded into 6 well plates and then cultured in the presence of the potential cp-asiRNAs in Opti-MEM for 24 hours, at which point the cp-asiRNA-containing Opti-MEM media was replaced with a serum-containing media. Twenty-four hours later, PDGFB mRNA levels in A549 cells were determined using qRT-PCR. Specifically, total RNA was extracted using RNAiPlus® (TaKaRa) and then 500 ng of the reaction mixture was used for cDNA synthesis using the High-capacity cDNA reverse transcription kit (Applied Biosystems). The synthesized cDNA was diluted and then quantitative RT-PCR was performed using power SYBR green PCR master Mix (Applied Biosystems).

After 48 hours of cp-asiRNAs incubation, the level of PDGFB protein expression was determined via western blot. Briefly, the treated A549 cells were lysed with Mammalian Protein Extraction Buffer (GE Healthcare). 20 μg of total protein extract were loaded onto a 10% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-PDGFB antibody (Abcam) and anti-γ-tubulin antibody (Bethyl). The membrane was then washed with TBST for 10 minutes three times and was incubated for 1 hour at the room temperature in 5% skim milk with HRP-conjugated secondary antibody (Santa Cruz). The membrane was washed with TBST for 10 minutes and treated with ECL substrate (Thermo Scientific). Protein bands were then imaged using a Chemidoc instrument (Bio-rad).

Figure 15:
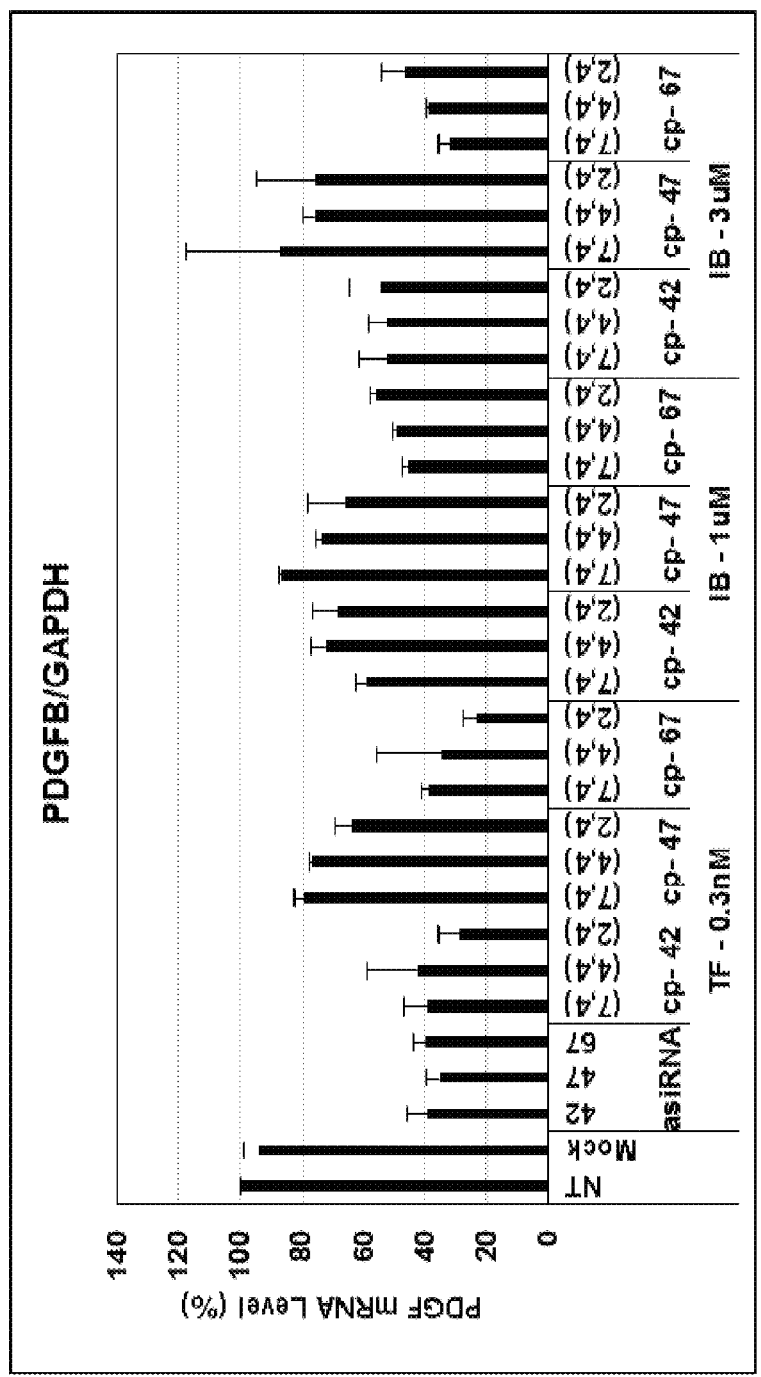
FIG. 15 shows the inhibition of PDGFB mRNA expression by exemplary cp-asiRNAs.
Figure 16:
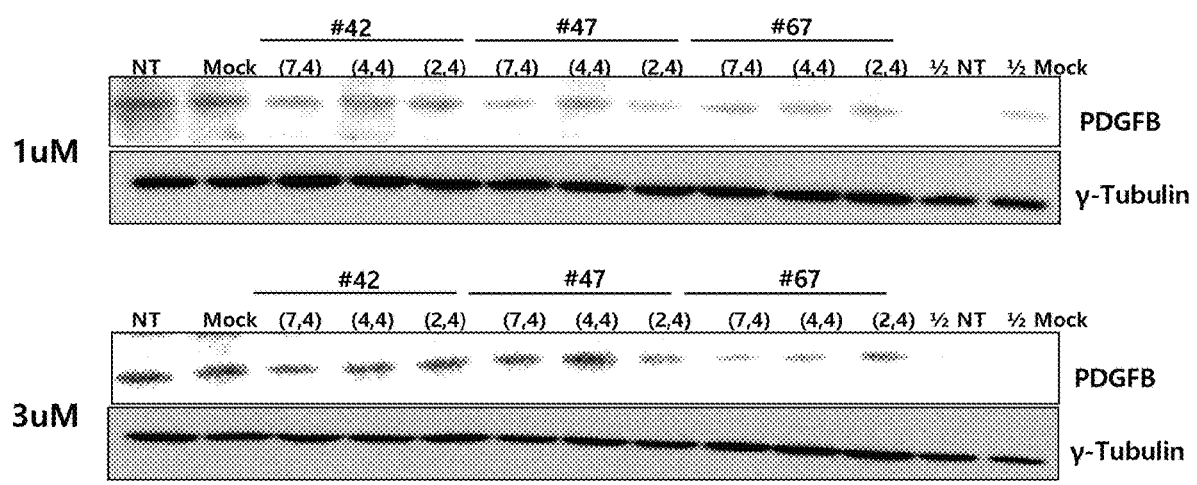
FIG. 16 shows the inhibition of PDGFB protein expression by exemplary cp-asiRNAs.
Figure 17:
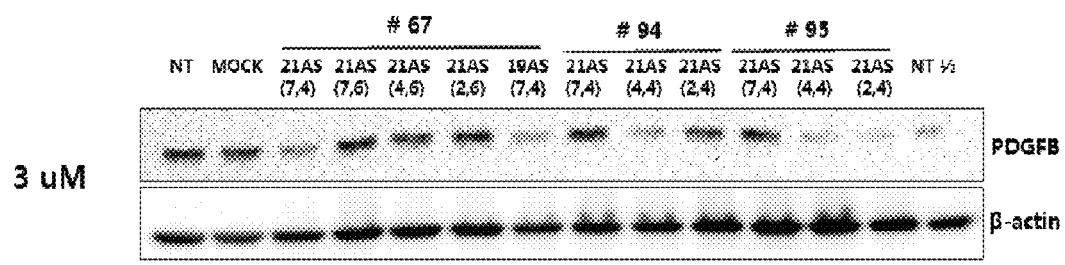
FIG. 17 shows the inhibition of PDGFB protein expression by 11 cp-asiRNAs of different antisense strand lengths (19 or 21 nucleotides) or chemical modification.

The levels of PDGFB inhibition by each of the 9 potential cp-asiRNAs is provided in FIGS. 15 and 16 From among the potential cp-asiRNAs tested, cp-asiPDGFB 67(7, 4) was selected for further study.

Example 14: Additional PDGFB cp-asiRNA Structures

Other potential PDGFB cp-asiRNA structures having different chemically modification or sequence were synthesized and tested for its ability to inhibit PDGFB expression (Table 6).

TABLE 6

Additional cp-asiRNA sequences (5' to 3', m = 2'-O-Methyl RNA.
* = phosphorothioate bond).

| SEQ ID NO: | Sequence |
|---|---|
| 443 | cp-asiPDGFB(67)-S:<br>mUCmCUmUGmGAmGUmGAmUA*mA*U*cholesterol |
| 444 | cp-asiPDGFB(67)21AS-(7,4):<br>AUUAUCACUCCAAGmGmAmC*mC*mC*mC*mA |
| 445 | cp-asiPDGFB(67)21AS-(7,6):<br>AUUAUCACUCCAAGmG*mA*mC*mC*mC*mC*mA |
| 446 | cp-asiPDGFB(67)21AS-(4,6):<br>AUUAUCACUCCAAGmG*mA*mC*mC*C*C*A |
| 447 | cp-asiPDGFB(67)21AS-(2,6):<br>AUUAUCACUCCAAGmG*mA*C*C*C*C*A |
| 448 | cp-asiPDGFB(67)19AS-(7.4):<br>AUUAUCACUCCAmAmGmG*mA*mC*mC*mC |

TABLE 6-continued

Additional cp-asiRNA sequences
(5' to 3', m = 2'-O-Methyl RNA.
* = phosphorothioate bond).

| SEQ ID NO: | Sequence |
|---|---|
| 449 | asiPDGFB(94)-S:<br>mCCmUUmCAmGUmUUmGUmAA*mA*G*cholesterol |
| 450 | asiPDGFB(94)-(7,4)AS:<br>CUUUACAAACUGAAmGmGmA*mA*mG*mC*mA |
| 451 | asiPDGFB(94)-(4,4)AS:<br>CUUUACAAACUGAAmGmGmA*mA*G*C*A |
| 452 | asiPDGFB(94)-(2,4)AS:<br>CUUUACAAACUGAAmGmGA*A*G*C*A |
| 453 | asiPDGFB(95)-S:<br>mCUmUCmAGmUUmUGmUAmAA*mG*U*cholesterol |
| 454 | asiPDGFB(95)-(7,4)AS:<br>ACUUUACAAACUGAmAmGmG*mA*mA*mG*mC |
| 455 | asiPDGFB(95)-(4,4)AS:<br>ACUUUACAAACUGAmAmGmG*mA*A*G*C |
| 456 | asiPDGFB(95)-(2,4)AS:<br>ACUUUACAAACUGAmAmGG*A*A*G*C |

The ability of cp-asiRNAs listed in Table 6 to inhibit PDGFB expression in A549 cells was tested. A549 cells were cultured in Dulbecco's Modified Eagle's Medium (DMEM, Gibco) containing 10% fetal bovine serum (FBS, Gibco) and 100 units/ml Penicillin 100 µg/ml. cp-asiRNAs listed in Table 6 were incubated at 95° C. for 2 minutes and at 37° C. for 1 hour in Opti-MEM (Gibco). Proper strand annealing of the potential cp-asiRNAs was confirmed by gel electrophoresis. On that day cp-asiRNAs treatment, 2.5×10$^4$ cells were seeded 24 well plates then cultured in the presence of the potential cp-asiRNAs in Opti-MEM for 24 hours, at which point the cp-asiRNA-containing Opti-MEM media was replaced with a serum-containing media. Twenty-four hours later, PDGFB expression levels in A549 cells were determined.

The cp-asiRNAs were incubated at 95° C. for 2 minutes and at 37° C. for 1 hour in Opti-MEM (Gibco). Proper strand annealing of the potential cp-asiRNAs was confirmed by gel electrophoresis. A549 cells were cultured in Dulbecco's modified Eagle's medium (DMEM, Gibco) containing 10% fetal bovine serum (FBS, Gibco) and 100 units/ml Penicillin and 100 µg/ml Streptomycin. On the day of treatment, 9×10$^4$A549 cells were seeded in 6-well plates then cultured in the presence of the potential cp-asiRNAs in Opti-MEM. Twenty-four hours later, PDGFB protein levels in A549 cells were determined via western blot. Briefly, the treated A549 cells were lysed with Mammalian protein Extraction Buffer (GE Healthcare). 20 µg of the total protein extract were loaded onto a 10% SDS-PAGE gel and electrophoresed at 120 V. After electrophoresis, the proteins were transferred to PVDF membrane (Bio-rad) previously activated by methanol (Merck) for 1 hour at 300 mA. The membrane was blocked for 1 hour at the room temperature with 5% skim milk (Seoul Milk) and then incubated overnight at 4° C. in 5% skim milk containing anti-PDGFB antibody (Abcam) and anti-γ-tubulin antibody (Bethyl). The membrane was then washed with TBST for 10 minutes three times and was incubated for 1 hour at the room temperature in 5% skim milk with HRP-conjugated secondary antibody (Santa Cruz). The membrane was washed with TBST for 10 minutes and treated with ECL substrate (Thermo Scientific). The Target protein bands were then imaged using a Chemidoc instrument (Bio-Rad).

As seen the FIG. 18, PDGFB expression potential cp-asiPDGFB 67 consist of 21 nucleotide antisense strands and potential cp-asiRNAs consist of 19 nucleotide antisense strands exhibited the similar levels of PDGFB inhibition. And cp-asiPDGFB 94(4,4), cp-asiPDGFB 95(4,4), asiPDGFB 95(2,4) shows effective PDGFB inhibition without delivery vehicle.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An asymmetric small interfering RNA complex formed with an antisense strand of 19 nt to 21 nt of the nucleotide sequence of SEQ ID NO: 418 that is complementary to a PDGFB mRNA sequence, and a sense strand of 16 nt in length and having the nucleotide sequence of SEQ ID NO: 417 that is complementary to the antisense strand, wherein the antisense strand and the sense strand form a complex in which the 5' end of the antisense strand and the 3' end of the sense strand form a blunt end.

2. The RNA complex of claim 1, wherein the RNA complex comprises a chemical modification.

3. The RNA complex of claim 2, wherein the chemical modification is a 2'-O-methylated nucleoside, a phosphorothioate bond or a hydrophobic moiety.

4. The RNA complex of claim 3, wherein the RNA complex comprises a hydrophobic moiety, and the hydrophobic moiety comprises a cholesterol moiety.

5. The RNA complex of claim 2, wherein the RNA complex comprises at least one phosphorothioate bond.

6. The RNA complex of claim 1, wherein the RNA complex is capable of penetrating the cellular membrane of a cell in the absence of a delivery vehicle.

7. A method of inhibiting Platelet Derived Growth Factor Beta (PDGFB) mRNA expression in a subject comprising administering the RNA complex of claim 1 to a subject.

8. The method of claim 7, wherein the method further comprises administering an additional agent to the subject, wherein the additional agent is a cancer therapeutic agent.

9. The method of claim 8, wherein the cancer therapeutic agent is a chemotherapeutic agent.

10. The method of claim 8, wherein the cancer therapeutic agent is an immune checkpoint inhibitor.

11. A pharmaceutical composition comprising an RNA complex of claim 1 and a pharmaceutically acceptable carrier.

12. A method comprising administering the pharmaceutical composition of claim 11 to a tumor or to the eye of a subject.

* * * * *

SEQUENCE LISTING

<160> NUMBER OF SEQ ID NOS: 458

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1
ugucaguauc cgaaucaauc a                    21

<210> SEQ ID NO 2
<211> LENGTH: 16
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 2
gauucggaua cugaca                                                    16

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gugucaguau ccgaaucaau c                                              21

<210> SEQ ID NO 4
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
auucggauac ugacac                                                    16

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
agugucagua uccgaaucaa u                                              21

<210> SEQ ID NO 6
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uucggauacu gacacu                                                    16

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cagugucagu auccgaauca a                                              21

<210> SEQ ID NO 8
<211> LENGTH: 16
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 8
ucggauacug acacug                                                    16

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9 acagucag uauccgaauc a                                                21

<210> SEQ ID NO 10
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
cggauacuga cacugu                                                    16

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
uacaguguca guauccgaau c                                              21

<210> SEQ ID NO 12
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ggauacugac acugua                                                    16

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cuacaguguc aguauccgaa u                                              21

<210> SEQ ID NO 14
<211> LENGTH: 16
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 14
gauacugaca cuguag                                                         16

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
uacuugggcu uccacaucag u                                                   21

<210> SEQ ID NO 16
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uguggaagcc caagua                                                         16

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gucacaguag gccuugaucu c                                                   21

<210> SEQ ID NO 18
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
caaggccuac ugugac                                                         16

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ugucacagua ggccuugauc u                                                   21

<210> SEQ ID NO 20
<211> LENGTH: 16
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 20
aaggccuacu gugaca                                                                                    16

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
augucacagu aggccuugau c                                                                              21

<210> SEQ ID NO 22
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
aggccuacug ugacau                                                                                    16

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
caugucacag uaggccuuga u                                                                              21

<210> SEQ ID NO 24
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ggccuacugu gacaug                                                                                    16

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
ccaugucaca guaggccuug a                                                                              21

<210> SEQ ID NO 26
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 26
gccuacugug acaugg                                                       16

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
uccaugucac aguaggccuu g                                                 21

<210> SEQ ID NO 28
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
ccuacuguga caugga                                                       16

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
caaguuggaa ggaccacaug c                                                 21

<210> SEQ ID NO 30
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ugguccuucc aacuug                                                       16

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ucaaguugga aggaccacau g                                                 21

<210> SEQ ID NO 32
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 32
gguccuucca acuuga                                                    16

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
uucaaguugg aaggaccaca u                                              21

<210> SEQ ID NO 34
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
guccuuccaa cuugaa                                                    16

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
caugguugug gccuugagcg a                                              21

<210> SEQ ID NO 36
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
caaggccaca accaug                                                    16

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ucaugguugu ggccuugagc g                                              21

<210> SEQ ID NO 38
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
```
aaggccacaa ccauga                                                    16

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
aucaugguug uggccuugag c                                              21

<210> SEQ ID NO 40
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
aggccacaac caugau                                                    16

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
caucaugguu guggccuuga g                                              21

<210> SEQ ID NO 42
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ggccacaacc augaug                                                    16

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ucaucauggu uguggccuug a                                              21

<210> SEQ ID NO 44
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gccacaacca ugauga                                                          16

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
aucaucaugg uuguggccuu g                                                    21

<210> SEQ ID NO 46
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ccacaaccau gaugau                                                          16

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
gaucaucaug guuguggccu u                                                    21

<210> SEQ ID NO 48
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
cacaaccaug augauc                                                          16

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ggaucaucau gguuguggcc u                                                    21

<210> SEQ ID NO 50
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
acaaccauga ugaucc                                                          16

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cggaucauca ugguuguggc c                                              21

<210> SEQ ID NO 52
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
caaccaugau gauccg                                                    16

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
cuguuuucca guuauuuacu g                                              21

<210> SEQ ID NO 54
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
aauaacugga aaacag                                                    16

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
guguucuguu uuccaguuau u                                              21

<210> SEQ ID NO 56
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
cuggaaaaca gaacac                                                    16

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
aguguucugu uuccaguua u                                              21

<210> SEQ ID NO 58
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
uggaaaacag aacacu                                                   16

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
aaguguucug uuuccaguu a                                              21

<210> SEQ ID NO 60
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ggaaaacaga acacuu                                                   16

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
uaaguguucu guuuccagu u                                              21

<210> SEQ ID NO 62
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
gaaaacagaa cacuua                                                   16

```
<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
gucaguaucc gaaucaauca c                                                    21

<210> SEQ ID NO 64
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
ugauucggau acugac                                                          16

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
ccuacagugu caguaccga a                                                     21

<210> SEQ ID NO 66
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
auacugacac uguagg                                                          16

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
uaggcugcgg ccaagacaag a                                                    21

<210> SEQ ID NO 68
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ucuuggccgc agccua                                                          16

<210> SEQ ID NO 69
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
auuggacacg uagggcugg a                                              21

<210> SEQ ID NO 70
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
ccccuacgug uccaau                                                   16

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ucccucugca cagcauugga c                                             21

<210> SEQ ID NO 72
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
augcugugca gaggga                                                   16

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
guucuccagc acuugcagcc u                                             21

<210> SEQ ID NO 74
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
gcaagugcug gagaac                                                   16

<210> SEQ ID NO 75
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
uguucuccag cacuugcagc c                                              21

<210> SEQ ID NO 76
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
caagugcugg agaaca                                                    16

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
auguucucca gcacuugcag c                                              21

<210> SEQ ID NO 78
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
aagugcugga gaacau                                                    16

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
ucaucacagc cgucugguuc u                                              21

<210> SEQ ID NO 80
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
cagacggcug ugauga                                                    16

<210> SEQ ID NO 81
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 81
aucaucacag ccgucugguu c                                              21

<210> SEQ ID NO 82
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
agacggcugu gaugau                                                    16

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
uaucaucaca gccgucuggu u                                              21

<210> SEQ ID NO 84
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
gacggcugug augaua                                                    16

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
cuaucaucac agccgucugg u                                              21

<210> SEQ ID NO 86
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
acggcuguga ugauag                                                    16

<210> SEQ ID NO 87
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 87
ucuaucauca cagccgucug g                                                 21

<210> SEQ ID NO 88
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
cggcugugau gauaga                                                       16

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
uucuaucauc acagccgucu g                                                 21

<210> SEQ ID NO 90
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
ggcugugaug auagaa                                                       16

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
uuucuaucau cacagccguc u                                                 21

<210> SEQ ID NO 92
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
gcugugauga uagaaa                                                       16

<210> SEQ ID NO 93
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 93
acuugggcuu ccacaucagu u                                              21

<210> SEQ ID NO 94
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
auguggaagc ccaagu                                                    16

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
auacuugggc uuccacauca g                                              21

<210> SEQ ID NO 96
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
guggaagccc aaguau                                                    16

<210> SEQ ID NO 97
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
acuggucugg uccaaaaucu g                                              21

<210> SEQ ID NO 98
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
uuuggaccag accagu                                                    16

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 99 uucacgguc ugguccaaaa u						21

<210> SEQ ID NO 100
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
ggaccagacc agugaa						16

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
uuucacuggu cugguccaaa a						21

<210> SEQ ID NO 102
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gaccagacca gugaaa						16

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
auuucacugg ucugguccaa a						21

<210> SEQ ID NO 104
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
accagaccag ugaaau						16

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
uauuucacug gucuggucca a        21

<210> SEQ ID NO 106
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
ccagaccagu gaaaua        16

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
uuauuucacu ggucuggucc a        21

<210> SEQ ID NO 108
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
cagaccagug aaauaa        16

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
uuuauuucac uggucugguc c        21

<210> SEQ ID NO 110
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
agaccaguga aauaaa        16

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
guuuauuuca cggucuggu c                                          21

<210> SEQ ID NO 112
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
gaccagugaa auaaac                                               16

<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
uguuuauuuc acuggucugg u                                         21

<210> SEQ ID NO 114
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
accagugaaa uaaaca                                               16

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
uuguuuauuu cacggucug g                                          21

<210> SEQ ID NO 116
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
ccagugaaau aaacaa                                               16

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117

-continued uuuguuuauu ucacuggucu g                                    21

<210> SEQ ID NO 118
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
cagugaaaua aacaaa                                          16

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
aguaggccuu gaucucuucu g                                    21

<210> SEQ ID NO 120
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
gagaucaagg ccuacu                                          16

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
caguaggccu ugaucucuuc u                                    21

<210> SEQ ID NO 122
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
agaucaaggc cuacug                                          16

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
acaguaggcc uugaucucuu c                                              21

<210> SEQ ID NO 124
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gaucaaggcc uacugu                                                    16

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
cacaguaggc cuugaucucu u                                              21

<210> SEQ ID NO 126
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
aucaaggccu acugug                                                    16

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
ucacaguagg ccuugaucuc u                                              21

<210> SEQ ID NO 128
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
ucaaggccua cuguga                                                    16

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
uuccauguca caguaggccu u                                              21

```
<210> SEQ ID NO 130
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
cuacugugac auggaa                                                      16

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
gcugaugcug cuuauuugc c                                                 21

<210> SEQ ID NO 132
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
aauaagcagc aucagc                                                      16

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
uggcugaugc ugcuuauuuu g                                                21

<210> SEQ ID NO 134
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
uaagcagcau cagcca                                                      16

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
uuggcugaug cugcuuauuu u                                                21
```

<210> SEQ ID NO 136
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
aagcagcauc agccaa                                                        16

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
ugguuggcug augcugcuua u                                                  21

<210> SEQ ID NO 138
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
cagcaucagc caacca                                                        16

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
cugguuggcu gaugcugcuu a                                                  21

<210> SEQ ID NO 140
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
agcaucagcc aaccag                                                        16

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
uuccugguug gcugaugcug c                                                  21

```
<210> SEQ ID NO 142
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
aucagccaac caggaa                                                      16

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
aaaaucauuu ccugguuggc u                                                21

<210> SEQ ID NO 144
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
accaggaaau gauuuu                                                      16

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
uaaaaucauu uccugguugg c                                                21

<210> SEQ ID NO 146
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
ccaggaaaug auuuua                                                      16

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
cuaaaaucau uuccugguug g                                                21

<210> SEQ ID NO 148
```

```
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
caggaaauga uuuuag                                                     16

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
gcuaaaauca uuuccugguu g                                               21

<210> SEQ ID NO 150
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
aggaaaugau uuuagc                                                     16

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
ugcuaaaauc auuccuggu u                                                21

<210> SEQ ID NO 152
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
ggaaaugauu uuagca                                                     16

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
cuuugugcua aaaucauuuc c                                               21

<210> SEQ ID NO 154
<211> LENGTH: 16
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
ugauuuuagc acaaag                                                     16

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
ccuuugugcu aaaaucauuu c                                               21

<210> SEQ ID NO 156
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
gauuuuagca caaagg                                                     16

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
aaggaccaca ugcaucaaac c                                               21

<210> SEQ ID NO 158
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
gaugcaugug guccuu                                                     16

<210> SEQ ID NO 159
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
gaaggaccac augcaucaaa c                                               21

<210> SEQ ID NO 160
<211> LENGTH: 16
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 160
augcaugugg uccuuc                                                        16

<210> SEQ ID NO 161
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
uggaaggacc acaugcauca a                                                  21

<210> SEQ ID NO 162
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162 gcauguguc cuucca                                                         16

<210> SEQ ID NO 163
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
uuggaaggac cacaugcauc a                                                  21

<210> SEQ ID NO 164
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
cauguggucc uuccaa                                                        16

<210> SEQ ID NO 165
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
guuggaagga ccacaugcau c                                                  21

<210> SEQ ID NO 166
<211> LENGTH: 16
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 166
augugguccu uccaac                                                         16

<210> SEQ ID NO 167
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
aguuggaagg accacaugca u                                                   21

<210> SEQ ID NO 168
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
ugugguccuu ccaacu                                                         16

<210> SEQ ID NO 169
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
aaguuggaag gaccacaugc a                                                   21

<210> SEQ ID NO 170
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
gugguccuuc caacuu                                                         16

<210> SEQ ID NO 171
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
guucaaguug gaaggaccac a                                                   21

<210> SEQ ID NO 172
<211> LENGTH: 16
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 172
uccuuccaac uugaac                                                        16

<210> SEQ ID NO 173
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
uuguggccuu gagcgaauag c                                                  21

<210> SEQ ID NO 174
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
ucgcucaagg ccacaa                                                        16

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
guuguggccu ugagcgaaua g                                                  21

<210> SEQ ID NO 176
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
cgcucaaggc cacaac                                                        16

<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
gguuguggcc uugagcgaau a                                                  21

<210> SEQ ID NO 178
<211> LENGTH: 16
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 178
gcucaaggcc acaacc                                                     16

<210> SEQ ID NO 179
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
ugguugtggc cuugagcgaa u                                               21

<210> SEQ ID NO 180
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
cucaaggcca caacca                                                     16

<210> SEQ ID NO 181
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
augguugugg ccuugagcga a                                               21

<210> SEQ ID NO 182
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
ucaaggccac aaccau                                                     16

<210> SEQ ID NO 183
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
ucggaucauc augguugugg c                                               21

<210> SEQ ID NO 184
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 184
aaccaugaug auccga                                                     16

<210> SEQ ID NO 185
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
aaucugcugg ucggaucauc a                                               21

<210> SEQ ID NO 186
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
auccgaccag cagauu                                                     16

<210> SEQ ID NO 187
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
aaaucugcug gucggaucau c                                               21

<210> SEQ ID NO 188
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
uccgaccagc agauuu                                                     16

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
gaaaucugcu ggucggauca u                                               21

<210> SEQ ID NO 190
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 190
ccgaccagca gauuuc                                                        16

<210> SEQ ID NO 191
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
agaaaucugc uggucggauc a                                                  21

<210> SEQ ID NO 192
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
cgaccagcag auuucu                                                        16

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
uagaaaucug cuggucggau c                                                  21

<210> SEQ ID NO 194
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
gaccagcaga uuucua                                                        16

<210> SEQ ID NO 195
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
uuagaaaucu gcuggucgga u                                                  21

<210> SEQ ID NO 196
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
accagcagau uucuaa                                                    16

<210> SEQ ID NO 197
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
uuuagaaauc ugcuggucgg a                                              21

<210> SEQ ID NO 198
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
ccagcagauu ucuaaa                                                    16

<210> SEQ ID NO 199
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
auaaguguuc uguuuccag u                                               21

<210> SEQ ID NO 200
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
aaaacagaac acuuau                                                    16

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
gagtcaacgg atttggtcgt                                                20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202

```
gacaagcttc ccgttctcag                                              20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
gcaagtgctg gagaacatca                                              20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
cacagccgtc tggttctgta                                              20

<210> SEQ ID NO 205
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
cagaccagug aaauaa                                                  16

<210> SEQ ID NO 206
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
uuauuucacu ggucuggucc a                                            21

<210> SEQ ID NO 207
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
cagaccagug aaauaa                                                  16

<210> SEQ ID NO 208
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
uuauuucacu ggucuggucc a                                            21
```

<210> SEQ ID NO 209
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
cagaccagug aaauaa                                                    16

<210> SEQ ID NO 210
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
uuauuucacu ggucuggucc a                                              21

<210> SEQ ID NO 211
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
cagaccagug aaauaa                                                    16

<210> SEQ ID NO 212
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
uuauuucacu ggucuggucc a                                              21

<210> SEQ ID NO 213
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
uccgaccagc agauuu                                                    16

<210> SEQ ID NO 214
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
aaaucugcug gucggaucau c                                              21

```
<210> SEQ ID NO 215
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
uccgaccagc agauuu                                                      16

<210> SEQ ID NO 216
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
aaaucugcug gucggaucau c                                                21

<210> SEQ ID NO 217
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
uccgaccagc agauuu                                                      16

<210> SEQ ID NO 218
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
aaaucugcug gucggaucau c                                                21

<210> SEQ ID NO 219
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
uccgaccagc agauuu                                                      16

<210> SEQ ID NO 220
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
aaaucugcug gucggaucau c                                                21
```

<210> SEQ ID NO 221
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
cagaccagug aaauaa                                                       16

<210> SEQ ID NO 222
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
uuauuucacu ggucugguc                                                    19

<210> SEQ ID NO 223
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
cagaccagug aaauaa                                                       16

<210> SEQ ID NO 224
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
uuauuucacu ggucuggucc a                                                 21

<210> SEQ ID NO 225
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
cagaccagug aaauaa                                                       16

<210> SEQ ID NO 226
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
uuauuucacu ggucugguc                                                    19

<210> SEQ ID NO 227

<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
uccgaccagc agauuu                                                   16

<210> SEQ ID NO 228
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
aaaucugcug gucggaucau c                                             21

<210> SEQ ID NO 229
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
guuugcaccu cucccu                                                   16

<210> SEQ ID NO 230
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
agggagaggu gcaaacuccc g                                             21

<210> SEQ ID NO 231
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
uuugcaccuc ucccug                                                   16

<210> SEQ ID NO 232
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
cagggagagg ugcaaacucc c                                             21

<210> SEQ ID NO 233
<211> LENGTH: 16

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
uugcaccucu cccugc                                                          16

<210> SEQ ID NO 234
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
gcagggagag gugcaaacuc c                                                    21

<210> SEQ ID NO 235
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
agccaacuuu ggaaaa                                                          16

<210> SEQ ID NO 236
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
uuuuccaaag uuggcuuugc a                                                    21

<210> SEQ ID NO 237
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
gccaacuuug gaaaaa                                                          16

<210> SEQ ID NO 238
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
uuuuuccaaa guuggcuuug c                                                    21

<210> SEQ ID NO 239
<211> LENGTH: 16
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 239
ccaacuuugg aaaaag                                                   16

<210> SEQ ID NO 240
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
cuuuuuccaa aguuggcuuu g                                             21

<210> SEQ ID NO 241
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
caacuuugga aaagu                                                    16

<210> SEQ ID NO 242
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
acuuuuucca aaguuggcuu u                                             21

<210> SEQ ID NO 243
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
aacuuuggaa aaaguu                                                   16

<210> SEQ ID NO 244
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
aacuuuuucc aaaguuggcu u                                             21

<210> SEQ ID NO 245
<211> LENGTH: 16
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 245
acuuuggaaa aaguuu                                                      16

<210> SEQ ID NO 246
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246 aaacuuuuc caaaguuggc u                                                 21

<210> SEQ ID NO 247
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
cuuuggaaaa aguuuu                                                      16

<210> SEQ ID NO 248
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
aaaacuuuuu ccaaaguugg c                                                21

<210> SEQ ID NO 249
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
aaauguugca aaaaag                                                      16

<210> SEQ ID NO 250
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
cuuuuuugca acauuuucug g                                                21

<210> SEQ ID NO 251
<211> LENGTH: 16
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 251
aauguugcaa aaaagc                                                       16

<210> SEQ ID NO 252
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252 gcuuuuugc aacauuuucu g                                                  21

<210> SEQ ID NO 253
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
ugcaaaaaag cuaagc                                                       16

<210> SEQ ID NO 254
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
gcuuagcuuu uuugcaacau u                                                 21

<210> SEQ ID NO 255
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
gcaaaaaagc uaagcc                                                       16

<210> SEQ ID NO 256
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
ggcuuagcuu uuugcaaca u                                                  21

<210> SEQ ID NO 257
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 257
gugaagacga accauc    16

<210> SEQ ID NO 258
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
gaugguucgu cuucacucgc c    21

<210> SEQ ID NO 259
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
ugaagacgaa ccaucg    16

<210> SEQ ID NO 260
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
cgaugguucg ucuucacucg c    21

<210> SEQ ID NO 261
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
guguuccuuu uccucu    16

<210> SEQ ID NO 262
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
agaggaaaag gaacacggca g    21

<210> SEQ ID NO 263
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
gucggcauga aucgcu                                                              16

<210> SEQ ID NO 264
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
agcgauucau gccgacuccg g                                                        21

<210> SEQ ID NO 265
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
ucggcaugaa ucgcug                                                              16

<210> SEQ ID NO 266
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
cagcgauuca ugccgacucc g                                                        21

<210> SEQ ID NO 267
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
ggcaugaauc gcugcu                                                              16

<210> SEQ ID NO 268
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
agcagcgauu caugccgacu c                                                        21

<210> SEQ ID NO 269
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 269
gcaugaaucg cugcug                                                  16

<210> SEQ ID NO 270
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
cagcagcgau ucaugccgac u                                            21

<210> SEQ ID NO 271
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
caugaaucgc ugcugg                                                  16

<210> SEQ ID NO 272
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
ccagcagcga uucaugccga c                                            21

<210> SEQ ID NO 273
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
cgcugcuggg cgcucu                                                  16

<210> SEQ ID NO 274
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
agagcgccca gcagcgauuc a                                            21

<210> SEQ ID NO 275
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
```

```
gcugcugggc gcucuu                                           16
```

<210> SEQ ID NO 276
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276

```
aagagcgccc agcagcgauu c                                     21
```

<210> SEQ ID NO 277
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277

```
cugcugggcg cucuuc                                           16
```

<210> SEQ ID NO 278
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278

```
gaagagcgcc cagcagcgau u                                     21
```

<210> SEQ ID NO 279
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279

```
gcugcuaccu gcgucu                                           16
```

<210> SEQ ID NO 280
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280

```
agacgcaggu agcagcagag a                                     21
```

<210> SEQ ID NO 281
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
cugcuaccug cgucug                                          16

<210> SEQ ID NO 282
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
cagacgcagg uagcagcaga g                                    21

<210> SEQ ID NO 283
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
ugcuaccugc gucugg                                          16

<210> SEQ ID NO 284
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
ccagacgcag guagcagcag a                                    21

<210> SEQ ID NO 285
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
gcuaccugcg ucuggu                                          16

<210> SEQ ID NO 286
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
accagacgca gguagcagca g                                    21

<210> SEQ ID NO 287
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
cuaccugcgu cugguc                                          16

<210> SEQ ID NO 288
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
gaccagacgc agguagcagc a                                            21

<210> SEQ ID NO 289
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
uaccugcguc ugguca                                                  16

<210> SEQ ID NO 290
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
ugaccagacg cagguagcag c                                            21

<210> SEQ ID NO 291
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
accugcgucu ggucag                                                  16

<210> SEQ ID NO 292
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
cugaccagac gcagguagca g                                            21

<210> SEQ ID NO 293
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
caacgccaac uuccug                                                  16

```
<210> SEQ ID NO 294
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
caggaaguug gcguuggugc g                                              21

<210> SEQ ID NO 295
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
aacgccaacu uccugg                                                    16

<210> SEQ ID NO 296
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
ccaggaaguu ggcguuggug c                                              21

<210> SEQ ID NO 297
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
acgccaacuu ccuggu                                                    16

<210> SEQ ID NO 298
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
accaggaagu uggcguuggu g                                              21

<210> SEQ ID NO 299
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
cgccaacuuc cuggug                                                    16
```

```
<210> SEQ ID NO 300
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
caccaggaag uuggcguugg u                                             21

<210> SEQ ID NO 301
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
gccaacuucc uggugu                                                   16

<210> SEQ ID NO 302
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
acaccaggaa guuggcguug g                                             21

<210> SEQ ID NO 303
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
ccaacuuccu ggugug                                                   16

<210> SEQ ID NO 304
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
cacaccagga aguuggcguu g                                             21

<210> SEQ ID NO 305
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
caacuuccug gugugg                                                   16

<210> SEQ ID NO 306
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
ccacaccagg aaguuggcgu u                                               21

<210> SEQ ID NO 307
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
ugaccauucg gacggu                                                     16

<210> SEQ ID NO 308
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
accguccgaa uggucacccg a                                               21

<210> SEQ ID NO 309
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
ggcaggguua uuuaau                                                     16

<210> SEQ ID NO 310
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
auuaaauaac ccugcccaca c                                               21

<210> SEQ ID NO 311
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
gcaggguuau uuaaua                                                     16

<210> SEQ ID NO 312
<211> LENGTH: 21
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
uauuaaauaa cccugcccac a                                              21

<210> SEQ ID NO 313
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
caggguuauu uaauau                                                    16

<210> SEQ ID NO 314
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
auauuaaaua acccugccca c                                              21

<210> SEQ ID NO 315
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
aggguuauuu aauaug                                                    16

<210> SEQ ID NO 316
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
cauauuaaau aacccugccc a                                              21

<210> SEQ ID NO 317
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
ggguuauuua auaugg                                                    16

<210> SEQ ID NO 318
<211> LENGTH: 21
<212> TYPE: RNA

<213> ORGANISM: Artificial Sequence
<220> FEATURE:
<223> OTHER INFORMATION: Description of Artificial Sequence: Synthetic oligonucleotide

<400> SEQUENCE: 318
ccauauuaaa uacccugcc c                                              21

<210> SEQ ID NO 319
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 319
gguuauuuaa uauggu                                                   16

<210> SEQ ID NO 320
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 320
accauauuaa auaacccugc c                                             21

<210> SEQ ID NO 321
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 321
guuauuuaau auggua                                                   16

<210> SEQ ID NO 322
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 322
uaccauauua aauaacccug c                                             21

<210> SEQ ID NO 323
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 323
guauuugcug uauugc                                                   16

<210> SEQ ID NO 324
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 324
gcaauacagc aaauaccaua u                                              21

<210> SEQ ID NO 325
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
uauuugcugu auugcc                                                    16

<210> SEQ ID NO 326
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
ggcaauacag caaauaccau a                                              21

<210> SEQ ID NO 327
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
auuugcugua uugccc                                                    16

<210> SEQ ID NO 328
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
gggcaauaca gcaaauacca u                                              21

<210> SEQ ID NO 329
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
uuugcuguau ugcccc                                                    16

<210> SEQ ID NO 330
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 330
ggggcaauac agcaaauacc a                                              21

<210> SEQ ID NO 331
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
ugcuguauug ccccca                                                    16

<210> SEQ ID NO 332
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332 uggggggcaau acagcaaaua c                                             21

<210> SEQ ID NO 333
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
gcuguauugc ccccau                                                    16

<210> SEQ ID NO 334
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334 auggggggcaa uacagcaaau a                                             21

<210> SEQ ID NO 335
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
cuguauugcc cccaug                                                    16

<210> SEQ ID NO 336
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 336
caugggggca auacagcaaa u                                              21

<210> SEQ ID NO 337
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
uguauugccc ccaugg                                                    16

<210> SEQ ID NO 338
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338 ccauggggc aauacagcaa a                                               21

<210> SEQ ID NO 339
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
guauugcccc caugggg                                                   16

<210> SEQ ID NO 340
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
cccauggggg caauacagca a                                              21

<210> SEQ ID NO 341
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
auugccccca uggggu                                                    16

<210> SEQ ID NO 342
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 342 accccaugggg ggcaauacag c                                           21

<210> SEQ ID NO 343
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
uugcccccau gggguc                                                  16

<210> SEQ ID NO 344
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
gaccccaugg gggcaauaca g                                            21

<210> SEQ ID NO 345
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
ugcccccaug gggucc                                                  16

<210> SEQ ID NO 346
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
ggaccccaug ggggcaauac a                                            21

<210> SEQ ID NO 347
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
gcccccaugg gguccu                                                  16

<210> SEQ ID NO 348
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 348
aggaccccau gggggcaaua c                                              21

<210> SEQ ID NO 349
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349 cccccaugggg guccuu                                                   16

<210> SEQ ID NO 350
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
aaggacccca uggggggcaau a                                             21

<210> SEQ ID NO 351
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
ccccaugggg uccuug                                                    16

<210> SEQ ID NO 352
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
caaggacccc auggggggcaa u                                             21

<210> SEQ ID NO 353
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353 ggggguccuug gaguga                                                   16

<210> SEQ ID NO 354
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
```
ucacuccaag gaccccaugg g                                              21

<210> SEQ ID NO 355
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
ggguccuugg agugau                                                    16

<210> SEQ ID NO 356
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
aucacuccaa ggaccccaug g                                              21

<210> SEQ ID NO 357
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
gguccuugga gugaua                                                    16

<210> SEQ ID NO 358
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
uaucacucca aggaccccau g                                              21

<210> SEQ ID NO 359
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
guccuuggag ugauaa                                                    16

<210> SEQ ID NO 360
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
uuaucacucc aaggacccca u                             21

<210> SEQ ID NO 361
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
uccuuggagu gauaau                                   16

<210> SEQ ID NO 362
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
auuaucacuc caaggacccc a                             21

<210> SEQ ID NO 363
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
guccgucugu cucgau                                   16

<210> SEQ ID NO 364
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
aucgagacag acggacgagg g                             21

<210> SEQ ID NO 365
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
uccgucuguc ucgaug                                   16

<210> SEQ ID NO 366
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
caucgagaca gacggacgag g                             21

<210> SEQ ID NO 367
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
ccgucugucu cgaugc                                                    16

<210> SEQ ID NO 368
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
gcaucgagac agacggacga g                                              21

<210> SEQ ID NO 369
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
gucugucucg augccu                                                    16

<210> SEQ ID NO 370
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
aggcaucgag acagacggac g                                              21

<210> SEQ ID NO 371
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
ucugucucga ugccug                                                    16

<210> SEQ ID NO 372
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
caggcaucga gacagacgga c                                              21

<210> SEQ ID NO 373
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
cugucucgau gccuga                                                      16

<210> SEQ ID NO 374
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
ucaggcaucg agacagacgg a                                                21

<210> SEQ ID NO 375
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
ugucucgaug ccugau                                                      16

<210> SEQ ID NO 376
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
aucaggcauc gagacagacg g                                                21

<210> SEQ ID NO 377
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
gucucgaugc cugauu                                                      16

<210> SEQ ID NO 378
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
aaucaggcau cgagacagac g                                                21

```
<210> SEQ ID NO 379
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
ucucgaugcc ugauuc                                                      16

<210> SEQ ID NO 380
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
gaaucaggca ucgagacaga c                                                21

<210> SEQ ID NO 381
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
cucgaugccu gauucg                                                      16

<210> SEQ ID NO 382
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
cgaaucaggc aucgagacag a                                                21

<210> SEQ ID NO 383
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
ucgaugccug auucgg                                                      16

<210> SEQ ID NO 384
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
ccgaaucagg caucgagaca g                                                21

<210> SEQ ID NO 385
```

```
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
cgaugccuga uucgga                                                      16

<210> SEQ ID NO 386
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
uccgaaucag gcaucgagac a                                                21

<210> SEQ ID NO 387
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
gaugccugau ucggac                                                      16

<210> SEQ ID NO 388
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
guccgaauca ggcaucgaga c                                                21

<210> SEQ ID NO 389
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
augccugauu cggacg                                                      16

<210> SEQ ID NO 390
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
cguccgaauc aggcaucgag a                                                21

<210> SEQ ID NO 391
<211> LENGTH: 16
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
cugauucgga cggcca                                                    16

<210> SEQ ID NO 392
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
uggccguccg aaucaggcau c                                              21

<210> SEQ ID NO 393
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
ugauucggac ggccaa                                                    16

<210> SEQ ID NO 394
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
uuggccgucc gaaucaggca u                                              21

<210> SEQ ID NO 395
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
gauucggacg gccaau                                                    16

<210> SEQ ID NO 396
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
auuggccguc cgaaucaggc a                                              21

<210> SEQ ID NO 397
<211> LENGTH: 16
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 397
auucggacgg ccaaug                                                    16

<210> SEQ ID NO 398
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
cauuggccgu ccgaaucagg c                                              21

<210> SEQ ID NO 399
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
uucggacggc caaugg                                                    16

<210> SEQ ID NO 400
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
ccauuggccg uccgaaucag g                                              21

<210> SEQ ID NO 401
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
ucggacggcc aauggu                                                    16

<210> SEQ ID NO 402
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
accauuggcc guccgaauca g                                              21

<210> SEQ ID NO 403
<211> LENGTH: 16
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 403
cggacggcca auggug                                                          16

<210> SEQ ID NO 404
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
caccauuggc cguccgaauc a                                                    21

<210> SEQ ID NO 405
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
ggacggccaa uggugc                                                          16

<210> SEQ ID NO 406
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
gcaccauugg ccguccgaau c                                                    21

<210> SEQ ID NO 407
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
gacggccaau ggugcu                                                          16

<210> SEQ ID NO 408
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
agcaccauug gccguccgaa u                                                    21

<210> SEQ ID NO 409
<211> LENGTH: 16
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 409
acggccaaug gugcuu                                                         16

<210> SEQ ID NO 410
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
aagcaccauu ggccguccga a                                                   21

<210> SEQ ID NO 411
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
cggccaaugg ugcuuc                                                         16

<210> SEQ ID NO 412
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
gaagcaccau uggccguccg a                                                   21

<210> SEQ ID NO 413
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
uccuucaguu uguaaa                                                         16

<210> SEQ ID NO 414
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
uuuacaaacu gaaggaagca g                                                   21

<210> SEQ ID NO 415
<211> LENGTH: 16
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 415
ccuucaguuu guaaag                                           16

<210> SEQ ID NO 416
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
cuuuacaaac ugaaggaagc a                                     21

<210> SEQ ID NO 417
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
cuucaguuug uaaagu                                           16

<210> SEQ ID NO 418
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
acuuuacaaa cugaaggaag c                                     21

<210> SEQ ID NO 419
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
uuauauuuuu gggggc                                           16

<210> SEQ ID NO 420
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
gcccccaaaa auauaaucac c                                     21

<210> SEQ ID NO 421
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
uauauuuuug ggggcu                                                              16

<210> SEQ ID NO 422
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
agcccccaaa aauauaauca c                                                        21

<210> SEQ ID NO 423
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
auauuuuugg gggcuu                                                              16

<210> SEQ ID NO 424
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424 aagccccaa aaauauaauc a                                                         21

<210> SEQ ID NO 425
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
uauuuugggg ggcuuu                                                              16

<210> SEQ ID NO 426
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426 aaagcccca aaauauaau c                                                          21

<210> SEQ ID NO 427
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 427
auuuuugggg gcuuuc                                                        16

<210> SEQ ID NO 428
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
gaaagccccc aaaaauauaa u                                                  21

<210> SEQ ID NO 429
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 429
caagggacct gctcatcata tt                                                 22

<210> SEQ ID NO 430
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 430
taccacagtc tccctcctat tt                                                 22

<210> SEQ ID NO 431
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
gcaggguuau uuaaua                                                        16

<210> SEQ ID NO 432
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
uauuaaauaa cccugcccac a                                                  21

<210> SEQ ID NO 433
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
```
uauuaaauaa cccugcccac a                                              21

<210> SEQ ID NO 434
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
uauuaaauaa cccugcccac a                                              21

<210> SEQ ID NO 435
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
guuauuuaau auggua                                                    16

<210> SEQ ID NO 436
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
uaccauauua aauaacccug c                                              21

<210> SEQ ID NO 437
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
uaccauauua aauaacccug c                                              21

<210> SEQ ID NO 438
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
uaccauauua aauaacccug c                                              21

<210> SEQ ID NO 439
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
uccuuggagu gauaau                                              16

<210> SEQ ID NO 440
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
auuaucacuc caaggacccc a                                        21

<210> SEQ ID NO 441
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
auuaucacuc caaggacccc a                                        21

<210> SEQ ID NO 442
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
auuaucacuc caaggacccc a                                        21

<210> SEQ ID NO 443
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
uccuuggagu gauaau                                              16

<210> SEQ ID NO 444
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
auuaucacuc caaggacccc a                                        21

<210> SEQ ID NO 445
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
auuaucacuc caaggacccc a                                        21

<210> SEQ ID NO 446
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
auuaucacuc caaggacccc a                                              21

<210> SEQ ID NO 447
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
auuaucacuc caaggacccc a                                              21

<210> SEQ ID NO 448
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
auuaucacuc caaggaccc                                                 19

<210> SEQ ID NO 449
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
ccuucaguuu guaaag                                                    16

<210> SEQ ID NO 450
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450
cuuuacaaac ugaaggaagc a                                              21

<210> SEQ ID NO 451
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
cuuuacaaac ugaaggaagc a                                              21

<210> SEQ ID NO 452
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
cuuuacaaac ugaaggaagc a                                              21

<210> SEQ ID NO 453
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
cuucaguuug uaaagu                                                    16

<210> SEQ ID NO 454
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
acuuuacaaa cugaaggaag c                                              21

<210> SEQ ID NO 455
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
acuuuacaaa cugaaggaag c                                              21

<210> SEQ ID NO 456
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
acuuuacaaa cugaaggaag c                                              21

<210> SEQ ID NO 457
<211> LENGTH: 5270
<212> TYPE: DNA
<213> ORGANISM: Homo sapiens

<400> SEQUENCE: 457
aaagtgattg attcggatac tgacactgta ggatctgggg agagaggaac aaaggaccgt     60
gaaagctgct ctgtaaaagc tgacacagcc ctcccaagtg agcaggactg ttcttcccac    120
tgcaatctga cagtttactg catgcctgga gagaacacag cagtaaaaac caggtttgct    180

-continued

| | |
|---|---|
| actgaaaaaa gaggaaagag aagactttca ttgacggacc cagccatggc agcgtagcag | 240 |
| ccctgcgttt tagacggcag cagctcggga ctctggacgt gtgtttgccc tcaagtttgc | 300 |
| taagctgctg gtttattact gaagaaagaa tgtggcagat tgttttcttt actctgagct | 360 |
| gtgatcttgt cttggccgca gcctataaca actttcggaa gagcatggac agcataggaa | 420 |
| agaagcaata tcaggtccag catgggtcct gcagctacac tttcctcctg ccagagatgg | 480 |
| acaactgccg ctcttcctcc agccctacg tgtccaatgc tgtgcagagg gacgcgccgc | 540 |
| tcgaatacga tgactcggtg cagaggctgc aagtgctgga gaacatcatg gaaaacaaca | 600 |
| ctcagtggct aatgaagctt gagaattata tccaggacaa catgaagaaa gaatggtag | 660 |
| agatacagca gaatgcagta cagaaccaga cggctgtgat gatagaaata gggacaaacc | 720 |
| tgttgaacca aacagcggag caaacgcgga agttaactga tgtggaagcc caagtattaa | 780 |
| atcagaccac gagacttgaa cttcagctct tggaacactc cctctcgaca aacaaattgg | 840 |
| aaaaacagat tttggaccag accagtgaaa taaacaaatt gcaagataag aacagtttcc | 900 |
| tagaaaagaa ggtgctagct atggaagaca agcacatcat ccaactacag tcaataaaag | 960 |
| aagagaaaga tcagctacag gtgttagtat ccaagcaaaa ttccatcatt gaagaactag | 1020 |
| aaaaaaaaat agtgactgcc acggtgaata attcagttct tcagaagcag caacatgatc | 1080 |
| tcatggagac agttaataac ttactgacta tgatgtccac atcaaactca gctaaggacc | 1140 |
| ccactgttgc taaagaagaa caaatcagct tcagagactg tgctgaagta ttcaaatcag | 1200 |
| gacacaccac gaatggcatc tacacgttaa cattccctaa ttctacagaa gagatcaagg | 1260 |
| cctactgtga catggaagct ggaggaggcg ggtggacaat tattcagcga cgtgaggatg | 1320 |
| gcagcgttga ttttcagagg acttggaaag aatataaagt gggatttggt aacccttcag | 1380 |
| gagaatattg gctgggaaat gagtttgttt cgcaactgac taatcagcaa cgctatgtgc | 1440 |
| ttaaaataca ccttaaagac tgggaaggga atgaggctta ctcattgtat gaacatttct | 1500 |
| atctctcaag tgaagaactc aattatagga ttcaccttaa aggacttaca gggacagccg | 1560 |
| gcaaaataag cagcatcagc caaccaggaa atgatttag cacaaaggat ggagacaacg | 1620 |
| acaaatgtat ttgcaaatgt tcacaaatgc taacaggagg ctggtggttt gatgcatgtg | 1680 |
| gtccttccaa cttgaacgga atgtactatc cacagaggca gaacacaaat aagttcaacg | 1740 |
| gcattaaatg gtactactgg aaaggctcag gctattcgct caaggccaca accatgatga | 1800 |
| tccgaccagc agatttctaa acatcccagt ccacctgagg aactgtctcg aactattttc | 1860 |
| aaagacttaa gcccagtgca ctgaaagtca cggctgcgca ctgtgtcctc ttccaccaca | 1920 |
| gagggcgtgt gctcggtgct gacgggaccc acatgctcca gattagagcc tgtaaacttt | 1980 |
| atcacttaaa cttgcatcac ttaacggacc aaagcaagac cctaaacatc cataattgtg | 2040 |
| attagacaga acacctatgc aaagatgaac ccgaggctga gaatcagact gacagtttac | 2100 |
| agacgctgct gtcacaacca agaatgttat gtgcaagttt atcagtaaat aactggaaaa | 2160 |
| cagaacactt atgttataca atacagatca tcttggaact gcattcttct gagcactgtt | 2220 |
| tatacactgt gtaaataccc atatgtcctg aattcaccat cactatcaca attaaaagga | 2280 |
| agaaaaaaac tctctaagcc ataaaaagac atattcaggg atattctgag aagggggttac | 2340 |
| tagaagttta atatttggaa aaacagttag tgcattttta ctccatctct taggtgcttt | 2400 |
| aaatttttat ttcaaaaaca gcgtatttac atttatgttg acagcttagt tataagttaa | 2460 |
| tgctcaaata cgtatttcaa atttatatgg tagaaacttc cagaatctct gaaattatca | 2520 |
| acagaaacgt gccatttag tttatatgca gaccgtacta tttttttctg cctgattgtt | 2580 |

```
aaatatgaag gtatttttag taattaaata taacttatta ggggatatgc ctatgtttaa    2640
cttttatgat aatatttaca attttataat ttgtttccaa aagacctaat tgtgccttgt    2700
gataaggaaa cttcttactt ttaatgatga ggaaaattat acatttcatt ctatgacaaa    2760
gaaactttac tatcttctca ctattctaaa acagaggtct gttttctttc ctagtaagat    2820
atatttttat agaactagac tacaatttaa tttctggttg agaaaagcct tctatttaag    2880
aaatttacaa agctatatgt ctcaagattc acccttaaat ttacttaagg aaaaaaataa    2940
ttgacactag taagttttt tatgtcaatc agcaaactga aaaaaaaaaa agggtttcaa     3000
agtgcaaaaa caaatctga tgttcataat atatttaaat attaccaaa aatttgagaa      3060 cacagggctg ggcgcagtgg ctcacaccta aatcccagt acattggtag gcaaggtggg     3120
cagatcacct gaggtcagga gttcaagacc agcctggaca catggtgaa acccgtctc     3180 tactaaataa tacaaaaatt agccaggcgt gctggcgggc acctgtaatc ccagctactc    3240
gggaggctga ggcagggaga attgcttgca ccagggaggg agaggttgca gtgagccaag    3300
atcgcaccac tgcactccag ccggggcaac agagcaagac tccatctcaa aaaaaaaaa    3360 aaaaaagaa agaaagaaa atttgagaac acagctttat actcgggact acaaaaccat     3420
aaactcctgg agttttaact cctttttgaaa ttttcatagt acaattaata ctaatgaaca   3480
tttgtgtaaa gctttataat ttaaaggcaa tttctcatat attcttttct gaatcatttg    3540
caaggaagtt cagagtccag tctgtaacta gcatctacta tatgtctgtc ttcaccttac    3600
agtgttctac cattattttt tctttattcc atttcaaaat ctaatttatt ttaccccaac    3660
ttctccccac cacttgacgt agttttagaa cacacaggtg ttgctacata tttggagtca    3720
atgatggact ctggcaaagt caaggctctg ttttatttcc accaaggtgc acttttccaa    3780
caactattta actagttaag aacctcccta tcttagaact gtatctactt tatatttaag    3840
aaggttttat gaattcaaca acggtatcat ggccttgtat caagttgaaa acaactgaa    3900 aataagaaaa tttcacagcc tcgaaagaca acaacaagtt tctaggatat ctcaatgaca    3960
agagtgatgg atacttaggt agggaaacgc taatgcagga aaaactggca acaacacaat   4020
ttatatcaat tctctttgta ggcaggtgat aaaaaattca aggacaaatc tcattatgtc    4080
attgtgcatc atatataatc tcttatgagc gagaatgggg ggaatttgtg tttttacttt    4140
acacttcaat tccttacacg gtatttcaaa caaacagttt tgctgagagg gcttttgtc    4200 tctccttaag aaaatgttta taaagctgaa aggaaatcaa acagtaatct taaaaatgaa    4260
aacaaaacaa cccaacaacc tagataacta cagtgatcag ggagcacagt tcaactcctt    4320
gttatgtttt agtcatatgg cctactcaaa cagctaaata acaacaccag tggcagataa    4380
aaatcaccat ttatctttca gctattaatc ttttgaatga ataaactgtg acaaacaaat    4440
taacattttt gaacatgaaa ggcaacttct gcacaatcct gtatccaagc aaactttaaa    4500
ttatccactt aattattact taatcttaaa aaaaattaga acccagaact tttcaatgaa    4560
gcatttgaaa gttgaagtgg aatttaggaa agccataaaa atataaatac tgttatcaca    4620
gcaccagcaa gccataatct ttataccttat cagttctatt tctattaaca gtaaaaacat    4680
taagcaagat ataagactac ctgcccaaga attcagtctt ttttcatttt tgttttctc     4740 agttctgagg atgttaatcg tcaaattttc tttggactgc attcctcact acttttttgca   4800 caatggtctc acgttctcac atttgttctc gcgaataaat tgataaaagg tgttaagttc    4860
tgtgaatgtc ttttaatta tgggcataat tgtgcttgac tggataaaaa cttaagtcca    4920
```

```
cccttatgtt tataataatt tcttgagaac agcaaactgc atttaccatc gtaaaacaac    4980
atctgactta cgggagctgc agggaagtgg tgagacagtt cgaacggctc ctcagaaatc    5040
cagtgaccca attctaaaga ccatagcacc tgcaagtgac acaacaagca gatttattat    5100
acatttatta gccttagcag gcaataaacc aagaatcact ttgaagacac agcaaaaagt    5160
gatacactcc gcagatctga aatagatgtg ttctcagaca acaaagtccc ttcagaatct    5220
tcatgttgca taaatgttat gaatattaat aaaaagttga ttgagaaaaa                5270

<210> SEQ ID NO 458
<211> LENGTH: 2700
<212> TYPE: DNA
<213> ORGANISM: Homo sapiens

<400> SEQUENCE: 458
agagagagag agagactgac tgagcaggaa tggtgagatg tttatcatgg gcctcgggga      60
ccccattccc gaggagcttt atgagatgct gagtgaccac tcgatccgct cctttgatga     120
tctccaacgc ctgctgcacg gagaccccgg agaggaagat ggggccgagt tggacctgaa     180
catgacccgc tcccactctg gaggcgagct ggagagcttg gctcgtggaa gaaggagcct     240
gggttccctg accattgctg agccggccat gatcgccgag tgcaagacgc gcaccgaggt     300
gttcgagatc tcccggcgcc tcatagaccg caccaacgcc aacttcctgg tgtggccgcc     360
ctgtgtggag gtgcagcgct gctccggctg ctgcaacaac cgcaacgtgc agtgccgccc     420
cacccaggtg cagctgcgac ctgtccaggt gagaaagatc gagattgtgc ggaagaagcc     480
aatctttaag aaggccacgg tgacgctgga agaccacctg gcatgcaagt gtgagacagt     540
ggcagctgca cggcctgtga cccgaagccc gggggggttcc caggagcagc gagccaaaac     600
gccccaaact cgggtgacca ttcggacggt gcgagtccgc cggcccccca agggcaagca     660
ccggaaattc aagcacacgc atgacaagac ggcactgaag gagacccttg agcctagggg     720
gcatcggcag gagagtgtgt gggcagggtt atttaatatg gtatttgctg tattgccccc     780
atggggtcct tggagtgata atattgtttc cctcgtccgt ctgtctcgat gcctgattcg     840
gacggccaat ggtgcttccc ccaccccctcc acgtgtccgt ccaccccttcc atcagcgggt     900 ctcctcccag cggcctccgg cgtcttgccc agcagctcaa gaagaaaaag aaggactgaa     960
ctccatcgcc atcttcttcc cttaactcca agaacttggg ataagagtgt gagagagact    1020
gatggggtcg ctcttttgggg gaaacgggct ccttcccctg cacctggcct gggccacacc    1080
tgagcgctgt ggactgtcct gaggagcccc gaggacctct cagcatagcc tgcctgatcc    1140 ctgaaccccct ggccagctct gaggggaggc acctccaggc aggccaggct gcctcggact    1200
ccatggctaa gaccacagac gggcacacag actggagaaa accctcccca cggtgcccaa    1260
acaccagtca cctcgtctcc ctggtgcctc tgtgcacagt ggcttctttt cgttttcgtt    1320
ttgaagacgt ggactcctct tggtgggtgt ggccagcaca ccaagtggct gggtgccctc    1380
tcaggtgggt tagagatgga gtttgctgtt gaggtggctg tagatggtga cctgggtatc    1440
ccctgcctcc tgccaccccct tcctccccac actccactct gattcacctc ttcctctggt    1500
tcctttcatc tctctacctc caccctgcat tttcctcttg tcctggccct tcagtctgct    1560
ccaccaaggg gctcttgaac cccttattaa ggccccagat gatcccagtc actcctctct    1620
agggcagaag actagaggcc agggcagcaa gggacctgct catcatattc caacccagcc    1680
acgactgcca tgtaaggttg tgcagggtgt gtactgcaca aggacattgt atgcagggag    1740
cactgttcac atcatagata aagctgattt gtatatttat tatgacaatt tctggcagat    1800
```

```
gtaggtaaag aggaaaagga tccttttcct aattcacaca aagactcctt gtggactggc    1860
tgtgcccctg atgcagcctg tggcttggag tggccaaata ggagggagac tgtggtaggg    1920
gcagggaggc aacactgctg tccacatgac ctccatttcc caaagtcctc tgctccagca    1980 actgccttc  caggtgggtg tgggacacct gggagaaggt ctccaaggga gggtgcagcc    2040
ctcttgcccg caccctccc  tgcttgcaca cttccccatc tttgatcctt ctgagctcca    2100
cctctggtgg ctcctcctag gaaaccagct cgtgggctgg gaatggggga gagaagggaa    2160
aagatcccca agacccctg  gggtgggatc tgagctccca cctcccttcc cacctactgc    2220
actttccccc ttcccgcctt ccaaaacctg cttccttcag tttgtaaagt cggtgattat    2280 attttgggg  gctttccttt tatttttaa  atgtaaaatt tatttatatt ccgtatttaa    2340
agttgtaaaa aaaaataacc acaaaacaaa accaaatgaa tccgccggag gtctgtctgt    2400
tggcatcgtg cgtgacaatt aacctttctg ccttggcagg atgtgccgac agcttgcggc    2460
gtgttcctct cactctggga gcctcaggcg tgatctcaca cactggcgtg cacatacaca    2520
cacacacaca tacatgctca cacatgcgtg cacatacacg caggcctgca acttggggga    2580
ggcctctgtc tggcgggaag aagagacaca caggctactc tgttggtctt ggtcctggca    2640
cagctcctga cacgtggact tgtgcgtgtc tctggcagtg acgagagatg ggtttctgca    2700
```